(12) United States Patent
Weeks et al.

(10) Patent No.: US 10,240,188 B2
(45) Date of Patent: Mar. 26, 2019

(54) DETECTION OF CHEMICAL MODIFICATIONS IN NUCLEIC ACIDS

(71) Applicant: The University of North Carolina at Chapel Hill, Chapel Hill, NC (US)

(72) Inventors: Kevin M. Weeks, Carrboro, NC (US); Nathan Siegfried, Chapel Hill, NC (US); Philip Homan, Chapel Hill, NC (US); Steven Busan, Chapel Hill, NC (US); Oleg V. Favorov, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 387 days.

(21) Appl. No.: 15/027,813

(22) PCT Filed: Oct. 7, 2014

(86) PCT No.: PCT/US2014/059489
§ 371 (c)(1),
(2) Date: Apr. 7, 2016

(87) PCT Pub. No.: WO2015/054247
PCT Pub. Date: Apr. 16, 2015

(65) Prior Publication Data
US 2016/0244818 A1    Aug. 25, 2016

Related U.S. Application Data

(60) Provisional application No. 61/887,614, filed on Oct. 7, 2013.

(51) Int. Cl.
*C12Q 1/68*        (2018.01)
*C12Q 1/6827*   (2018.01)
(Continued)

(52) U.S. Cl.
CPC ......... *C12Q 1/6827* (2013.01); *C12N 9/1241* (2013.01); *C12N 15/01* (2013.01); *C12Q 1/6806* (2013.01)

(58) Field of Classification Search
CPC ....................................................... C12Q 1/68
See application file for complete search history.

(56) References Cited

U.S. PATENT DOCUMENTS 6,794,140 B1    9/2004  Goldsborough
8,318,424 B2 *  11/2012  Weeks ................. C12Q 1/6811
                                                        435/6.1

(Continued)

FOREIGN PATENT DOCUMENTS

WO   WO 2007/100637 A2    9/2007
WO   WO 2007/145940 A2    12/2007

(Continued)

OTHER PUBLICATIONS

Steen et al., Fingerprinting noncanonical and tertiary RNA structures by differential SHAPE reactivity, J Am Chem Soc. Aug. 15, 2012;134(32):13160-3. doi: 10.1021/ja304027m. Epub Aug. 1, 2012.*

(Continued)

*Primary Examiner* — Aaron A Priest
(74) *Attorney, Agent, or Firm* — Jenkins, Wilson, Taylor & Hunt, P.A.

(57) ABSTRACT

The presently disclosed subject matter relates to technology and methods for analyzing the structure of nucleic acid molecules, such as RNA molecules. More particularly, the presently disclosed subject matter is directed to methods of compositions for, and computer program products for nucleic acid analysis, such as RNA structure analysis.

14 Claims, 19 Drawing Sheets

Specification includes a Sequence Listing.

(51) Int. Cl.
  *C12N 15/01* (2006.01)
  *C12N 9/12* (2006.01)
  *C12Q 1/6806* (2018.01)

(56) References Cited

U.S. PATENT DOCUMENTS

2010/0035761 A1  2/2010 Weeks et al.
2011/0059446 A1  3/2011 Carrell et al.

FOREIGN PATENT DOCUMENTS

WO  WO 2012/054809 A2  4/2012
WO  WO-2012054809 A2 *  4/2012  ............... C12Q 1/68

OTHER PUBLICATIONS

Alvarez et al., "Long-Range RNA-RNA Interactions Circularize the Dengue Virus Genome," Journal of Virology, vol. 79, No. 11, pp. 6631-6643 (Jun. 2005).
Bailor et al., "Topological constraints: using RNA secondary structure to model 3D conformation, folding pathways, and dynamic adaptation," Structural Biololgy, vol. 21, pp. 296-305 (2011).
Cheng et al., Consistent global structures of complex RNA states through multidimensional chemical mapping, eLife, vol. 4:e07600 pp. 1-38 (2015).
Cordero et al., "Quantitative Dimethyl Sulfate Mapping for Automated RNA Secondary Structure Inference," Biochemistry, vol. 51, pp. 7037-1039 (2012).
Dann et al., "Structure and Mechanism of a Metal-Sensing Regulatory RNA," Cell, vol. 130, pp. 878-892 (Sep. 7, 2007).
Darty et al., "VARNA: Interactive drawing and editing of the RNA secondary structure," Bioinformatics, vol. 25, No. 15, pp. 1974-1975 (2009).
Deigan et al., Accurate SHAPE-directed RNA structure determination, PNAS, vol. 106, No. 1, pp. 97-201 (Jan. 6, 2009).
Dethoff et al., "Functional complexity and regulation through RNA dynamics," Nature, vol. 482, pp. 322-330 (Feb. 16, 2012).
Ding et al., "In vivo genome-wide profiling of RNA secondary structure reveals novel regulatory features," Nature, vol. 505, pp. 696-700 (17 pages) (Jan. 30, 2014).
Fang et al., Probing Xist RNA Structure in Cells Using Targeted Structure-Seq, PLOS Genetics, pp. 1-29 (Dec. 8, 2015).
Hajdin et al., On the significance of an RNA tertiary structure prediction, RNA, vol. 16, pp. 1340-1349 (2010).
Hajdin et al., Accurate SHAPE-directed RNA secondary structure modeling, including pseudoknots, PNAS, vol. 110, No. 14, pp. 5498-5503 (Apr. 2, 2013).
Hector et al., Snapshots of pre-rRNA structural flexibility reveal eukaryotic 40S assembly dynamics at nucleotide resolution, Nucleic Acids Research, vol. 42, No. 19, pp. 12138-12154 (Sep. 8, 2014).
Incarnato et al., "Genome-wide profiling of mouse RNA secondary structures reveals key features of the mammalian transcriptome," Genome Biology, vol. 15, No. 491, pp. 1-13 (2014).
Jin et al., New insights into RNA secondary structure in the alternative splicing of pre-mRNAs, RNA Bilogy, vol. 8, No. 3, pp. 450-457 (2011).
Karabiber et al., QuShape: Rapid, accurate, and best-practices quantification of nucleic acid probing information, resolved by capillary electrophoresis, vol. 19, pp. 63-73 (2013).
Kazantsev et al., Mapping metal-binding sites in the catalytic domain of bacterial RNase P RNA, RNA, vol. 15, pp. 266-276 (2009).
Kertesz et al., "Genome-wide measurement of RNA secondary structure in yeast," Nature, vol. 467, pp. 103-107 (Sep. 2, 2010).
Kielpinski et al., Massive parallel-sequencing-based hydroxyl radical probing of RNA accessibility, Nucleic Acids Research, vol. 42, No. 8, pp. 1-12 (2014).
Kladwang et al., A two-dimensional mutate-and-map strategy for non-coding RNA structure, Nature Chemistry, vol. 3, pp. 954-962 (Dec. 2011).
Kudla et al., Cross-linking, ligation, and sequencing of hybrids reveals RNA-RNA interactions in yeast, PNAS, vol. 108, No. 24, pp. 10010-10015 (Jun. 14, 2011).
Leontis et al., "The building blocks and motifs of RNA architecture," Curr Opin Struct Biol, vol. 16, pp. 279-287 (2006).
Leonard et al., "Principles for Understanding the Accuracy of SHAPE-Directed RNA Structure Modeling," Biochemistry, vol. 52, pp. 588-595 (2013).
Loughrey et al., SHAPE-Seq 2.0: systematic optimization and extension of high-throughput chemical probing of RNA secondary structure with next generation sequencing, Nucleic Acids Research, vol. 42, No. 21, pp. 1-10 (Oct. 10, 2014).
Low et al., "SHAPE-directed RNA secondary structure predic," Methods, vol. 52, pp. 150-158 (2010).
Mauger et al., "The genetic code as expressed through relationships between mRNA structure and protein function," FEBS Letters, vol. 587, pp. 1180-1188 (2013).
Montange et al., "Riboswitches: emerging themes in RNA structure and function", Annu Rev Biophys, vol. 37, pp. 117-133 (2008).
Murphy et al., "GAAA Tetraloop and Conserved Bulge Stabilize Tertiary Structure of a Group I Intron Domain," J. Mol. Biol., vol. 236, pp. 49-63 (1994).
Poulsen et al., SHAPE Selection (SHAPES) enrich for RNA structure signal in SHAPE sequencing-based probing data, RNA, vol. 21, pp. 1042-1052 (2015).
Ramani et al., "High-throughput determination of RNA structure by proximity ligation," Nature Biotechnology, vol. 33, No. 9, pp. 980-985 (Sep. 2015).
Reuter et al., "RNAstructure: software for RNA secondary structure prediction and analysis," vol. 11, No. 129, pp. 1-9 (2010).
Rivas et al., A range of complex probabilistic models for RNA secondary structure prediction that includes the nearest-neighbor model and more, vol. 18, pp. 193-212 (2012).
Rouskin et al., "Genome-wide probing of RNA structure reveals active unfolding of mRNA structures in vivo," Nature, vol. 505, pp. 701-705 (17 pages) (Jan. 30, 2014).
Seetin et al., "Massively Parallel RNA Chemical Mapping with a Reduced Bias MAP-Seq Protocol," Methods in Molecular Biology, vol. 1086, pp. 95-117 (2014).
Serganov et al., "Structural basis for gene regulation by a thiamine pyrophosphate-sensing riboswitch," Nature, vol. 441, pp. 1167-1171 (Jun. 29, 2006).
Sharp, "The Centrality of RNA," Cell, vol. 136, pp. 577-580 (2009).
Shendure et al., "Next-generation DNA sequencing," Nat Biotechnol, vol. 26, No. 10, pp. 1135-1145 (Oct. 2008).
Spitale et al., "Structural imprints in vivo decode RNA regulatory mechanisms," Nature, vol. 519, pp. 486-490 (19 pages) (Mar. 26, 2015).
Steen et al., "Fingerprinting Noncanonical and Tertiary RNA Structures by Differential SHAPE Reactivity," J. Am. Chem. Soc., vol. 134, pp. 13160-13163 (2012).
Sugimoto et al., hiCLIP reveals the in vivo atlas of mRNA secondary structures recognized by Staufen 1, Nature, vol. 519, pp. 491-493 (21 pages) (Mar. 26, 2015).
Szewczak et al., An RNA internal loop acts as a hinge to facilitate ribozyme folding and catalysis, RNA, vol. 3, No. 8, pp. 838-849 (1997).
Talkish et al., Mod-seq: high-throughput sequencing for chemical probing of RNA structure, RNA, vol. 20, pp. 713-720 (2014).
Watters et al., "Characterizing RNA structures in vitro and in vivo with selective 2'-hydroxyl acylation analyzed by primer extension sequencing (SHAPE-Seq)," Methods, vol. 103, pp. 34-48 (2016).
Weeks, "Advances in RNA structure analysis by chemical probing," Structural Biology, vol. 20, pp. 295-304 (2010).
U.S. Appl. No. 60/810,960, filed Jun. 5, 2006, Weeks.
U.S. Appl. No. 60/854,650, filed Oct. 26, 2006, Weeks.
U.S. Appl. No. 60/878,724, filed Jan. 5, 2007, Weeks.

(56) References Cited

OTHER PUBLICATIONS

Amarasinghe et al, "NMR struture of the HIV-1 nucleocapsid protein bound to stem-loop SL2 of the psi-RNA packaging signal. Implications for genome recognition." J. Mol. Biol, vol. 301, pp. 491-511 (2000).
Badorrek et al., "RNA flexibility in the dimerization domain of a gamma retrovirus," Nature Chemical Biology, vol. 1, pp. 104-111 (2005).
Badorrek et al., "Structure of an RNA switch that enforces stringent retroviral genomic RNA dimerization." Proceedings of the National Academy of Sciences USA, vol. 103, pp. 13640-13645 (Sep. 12, 2006).
Badorrek et al, "Architecture of a gamma retroviral genomic RNA dimer," Biochemistry. vol. 45, pp. 12664-12672 (2006).
Barrick et al., "New RNA motifs suggest an expanded scope for riboswitches in bacterial genetic control," Proceedings of the National Academy of Sciences, USA, vol. 101, pp. 6421-6426 (Apr. 27, 2004).
Baudin, et al., "Functional Sites in the 5' Region of Human Immunodeficiency Virus Type 1 RNA Form Defined Structural Domains," J Mol Biol., vol. 229, pp. 382-397 (1993).
Berkhout et al., "Structure and Function of the Human Immunodeficiency Virus Leader RNA," Prog Nucleic Acid Res. Mol Biol., vol. 54, pp. 1-34 (1996).
Berkhout et al., "In Vitro Evidence That the Untranslated Leader of the HIV-1 Genome Is an RNA Checkpoint That Regulates Multiple Functions through Conformational Changes," J Biol Chem., vol. 277, No. 22, pp. 19967-19975 (2002).
Berkowitz, et al., "RNA Packaging," Curr Top Micorbiol Immunol., pp. 177-218 (1996).
Brenowitz et al., "Quantitative DNase Footprint Titration: A Method for Studying Protein-DNA Interactions," Methods Enzymol., vol. 130, pp. 132-181 (1986).
Brion et al., "Hierarchy and Dynamics of RNA Folding," Rev. Biophsy. Biomol. Struct. vol. 26, pp. 113-137 (1997).
Burns et al., "Vesicular stomatitis virus G glycoprotein pseudotyped retroviral vectors: concentration to very high titer and efficient gene transfer into mammalian and nonmammalian cells," Proceedings of the National Academy of Sciences USA, vol. 90, pp. 8033-8037 (Sep. 1993).
Cate et al., "Crystal Structure of a Group I Ribozyme Domain: Principles of RNA Packing," Science, vol. 273, No. 5282, pp. 1-21 (1996).
Cardinaud et al., "Irreversible enzyme inhibitors. CLXXII. Proteolytic enzymes. XVI. Covalent bonding of the sulfonyl fluoride group to serine outside the active-site of .alpha.-chymotrypsin by exo-type active-site directed irreversible inhibitors," J. Med. Chem., vol. 13, pp. 467-470 (1970).
Chamberlin et al., "Mapping Local Nucleotide Flexibility by Selective Acylation of 2'-Amine Substituted RNA," J Am Chem Soc., vol. 122, pp. 216-224 (2000).
Chamberlin et al., "Catalysis of amide synthesis by RNA phosphodiester and hydroxyl groups," Proceedings of the National Academy of Sciences USA, vol. 99, pp. 14688-14693 (Nov. 12, 2002).
Chamberlin et al., "Differential Helix Stabilities and Sites Preorganized for Tertiary Interactions Revealed by Monitoring Local Nucleotide Flexibility in the bI5 Group I Intron RNA," Biochemistry, vol. 42, pp. 901-909 (2003).
Chen et al., "Structure of stem-loop IV of Tetrahymena telomerase RNA," EMBO J., vol. 25, pp. 3156-3166 (2006).
Cheong et al., "Solution structure of an unusually stable RNA hairpin, 5'GGAC(UUCG)GUCC," Nature, vol. 346, pp. 680-682 (1990).
Chetouani et al, "ESSA: An integrated and interactive computer tool for analysing RNA secondary structure," Nucleic Acids Research, vol. 25, No. 17, pp. 3514-3522 (1997).
Communication of European publication number and information on the application of Article 67(3) EPC corresponding to European Patent Application No. 14851691.7 dated Jul. 20, 2016.
Communication of the extended European Search Report corresponding to European Patent Application No. 14851691.7 dated Mar. 2, 2017.
Damgaard et al., "RNA Interactions in the 5' Region of the HIV-1 Genome," J Mol Biol., vol. 336, pp. 369-379 (2004).
Das et al., SAFA: Semi-automated footprinting analysis software for high-throughput quantification of nucleic acid footprinting experiemnts, RNA, vol. 11, pp. 344-354 (2005).
De Belder et al., "Preparation and properties of fluorescein-labelled hyaluronate," Carbohydrate Research, vol. 44, pp. 251-257 (1975).
De Guzman et al., "Structure of the HIV-1 Nucleocapsid Protein Bound to the SL3 Ψ-RNA Recognition Element," Science, vol. 279, pp. 384-388 (1998).
Doshi et al., "Evaluation of the suitability of free-energy minimization using nearest-neighbor energy parameters for RNA secondary structure prediction," BMC Bioinformatics, vol. 5, pp. 1-22 (2004).
Dowell et al., "Evaluation of several lightweight stochastic context-free grammars for RNA secondary structure prediction," BMC Bioinformatics, vol. 5, pp. 1-14 (2004).
Eddy, "How do RNA folding algorithms work?," Nature Biotech., vol. 22, pp. 1457-1458 (2004).
Ehresmann et al., "Probing the structure of RNAs in solution," Nucleic Acids Res. vol. 15, pp. 9109-9128 (1987).
Frankel et al., "HIV-1: fifteen proteins and an RNA," Ann Rev Biochem., vol. 67, pp. 1-25 (1998).
Fu et al., "Characterization of human immunodeficiency virus type 1 dimeric RNA from wild-type and protease-defective virions," J Virol., vol. 68, pp. 5013-5018 (1994).
Genbank AF324493 (HIV-1 vector pNL4-3, complete sequence).
Gherghe et al., "The SL1-SL2 (stem loop) Domain is the Primary Determinant for Stability of the Gamma Retroviral Genomic RNA Dimer," J Biol Chem., vol. 281, pp. 37952-37961 (2006).
Gherghe et al., "Strong correlation between SHAPE chemistry and the generalized NMR order parameter (S2) in RNA," J Am Chem Soc., vol. 130, No. 37, pp. 12244-12245 (Sep. 17, 2008).
Giddings et al., "A software system for data analysis in automated DNA sequencing," Genome Res., vol. 8, pp. 644-665 (1998).
Helm et al., "The presence of modified nucleotides is required for cloverleaf folding of a human mitochondrial tRNA," Nucl. Acids Res., vol. 26, No. 7, pp. 1636-1643 (1998).
Hiratsuka, "New ribose-modified fluorescent analogs of adenine and guanine nucleotides available as substrates for various enzymes," Biochem Biophys Acta., vol. 742, pp. 496-508 (1983).
Hogeweg et al., "Energy directed folding of RNA sequences," Nucleic Acids Res., vol. 12, pp. 67-74 (1984).
Homan et al., "Single-molecule correlated chemical probing of RNA," PNAS, vol. 111, No. 38, pp. 13858-13863 (Sep. 23, 2014).
International Preliminary Report on Patentability for International Application No. PCT/US2007/13226 dated Jan. 30, 2008.
International Search Report for International Application No. PCT/US2007/13226, dated Jan. 30, 2008.
Isel et al., "Structural basis for the specificity of the initiation of HIV-1 reverse transcription," The EMBO Journal, vol. 18, No. 4, pp. 1038-1048 (1999).
John, et al., "Tagging DNA mismatches by selective 2'-amine acylation," Chemistry & Biology, vol. 7, No. 6, pp. 405-410 (2000).
John et al., "van't Hoff enthalpies without baselines," Protein Sci., vol. 9, pp. 1416-1419 (2000).
John et al., "Chemical interrogation of mismatches in DNA-DNA and DNA-RNA duplexes under nonstringent conditions by selective 2'-amine acylation," Biochemistry, vol. 41, pp. 6866-6874 (2002).
John et al., "Mechanics of DNA Flexibility Visualized by Selective 2'-Amine Acylation at Nucleotide Bulges,"J. Mol. Biol., vol. 337, pp. 611-619 (2004).
Jones et al., "Lack of secondary structure characterizes the 5' ends of mammalian mitochondrial mRNAs," RNA, vol. 14, pp. 862-871 (2008).
Knapp, "Enzymatic Approaches to Probing of RNA Secondary and Tertiary Structure," Methods in Enzymology, vol. 180, pp. 192-212 (1989).
Krasilnikov et al., "Crystal structure of the specificity domain of ribonuclease P," Nature, vol. 421, pp, 760-764 (Feb. 13, 2003).

(56) References Cited

OTHER PUBLICATIONS

Laederach et al., "Semi-automated and rapid quantification of nucleic acid footprinting and structure mapping experiments," Nat Protoc., vol. 3, No. 9, pp. 1395-1401 (2008).
Larson et al., "The function of proteins that interact with mRNA," Mol. Cell Biochem., vol. 74, pp. 5-15 (1987).
Lorsch et al., "Reverse transcriptase reads through a 2'-5' linkage and a 2'-thiophospate in a template," Nucleic Acids Research, vol. 23, No. 15, pp. 2811-2814 (1995).
Lucks et al., "Multiplexed RNA structure characterization with selevtive 2'-hydroxyl acylation analyzed by primer extension sequencing (SHAPE-Seq)," PNAS, vol. 108, No. 27, pp. 11063-11068 (Jul. 5, 2011).
Mathews et al., "Expanded improves prediction of RNA secondary structure," J. Mol. Biol., vol. 288, pp. 911-940 (1999).
Mathews et al., "Incorporating chemical modification constraints into a dynamic programming algorithm for prediction of RNA secondary structure," Proceedings of the National Academy of Sciences USA (PNAS), vol. 101, No. 19, pp. 7287-7292 (May 11, 2004).
Mathews et al., "Prediction of RNA secondary structure by free energy minimization," Prediction of Curr. Opin. Struct. Biol., vol. 16, pp. 270-278 (2006).
Matzura et al., "RNAdraw: an integrated program for RNA secondary structure calculation and analysis under 32-bit Microsoft Windows," CABIOS, vol. 12, No. 3, pp. 247-249 (1996).
Merino et al., "View an RNA melt with single nucleotide resolution," 228th ACS National Meeting, Philadelphia, PA, p. 1 (Aug. 22-26, 2004).
Merino et al., "RNA Structure Analysis at Single Nucleotide Resolution by Selective 2'-Hydroxyl Acylation and Primer Extension (SHAPE)," Journal of the American Chemical Society, vol. 127, pp. 4223-4231 (2005).
Milligan et al., "Synthesis of small RNAs using T7 RNA polymerase," Methods Enzymol., vol. 180, pp. 51-62 (1989).
Moorman et al., "New class of serine protease inactivators based on isatoic anhydride," J. Am Chem., vol. 104, pp. 6785-6786 (1982).
Mortimer et al., "A fast-acting reagent for accurate analysis of RNA secondary and tertiary structure by SHAPE chemistry," J. Am. Chem. Soc., vol. 129, pp. 4144-4145 (2007).
Notification Concerning Transmittal of International Preliminary Report on Patentability for International Application No. PCT/US2014/059489 dated Apr. 26, 2016.
Notice of References Cited corresponding to U.S. Appl. No. 12/227,987 dated Mar. 28, 2011.
Notice of References Cited corresponding to U.S. Appl. No. 12/227,987, dated Oct. 13, 2011.
Notification Concerning Transmittal of International Preliminary Report on Patentability for International Application No. PCT/US2014/059486 dated Apr. 26, 2016.
Notification of Transmittal of the International Search Report and the Written Opinion of the International Searching Authority, or the Declaration for International Application No. PCT/US2014/059489 dated Jan. 13, 2015.
Nussinov et al., "Algorithms for loop matchings," J. Appl. Math., vol. 35m, No. 1, pp. 68-82 (1978).
Office Action corresponding to U.S. Appl. No. 12/227,987, dated Oct. 13, 2011.
Office Action corresponding to U.S. Appl. No. 12/227,987 dated Mar. 28, 2011.
Osterburg et al., "Computer support of DNA sequence analysis," Computer Prog. In Biomed., vol. 13, pp. 101-109 (1981).
Paegel, B.M., "High throughput DNA sequencing with a microfabricated 96-lane capillary arra.electrophoresis bioprocessor," Proceedings of the National Academy of Sciences, USA (PNAS), vol. 99, No. 2, pp. 574-579 (Jan. 22, 2002).
Paillart et al., "In vitro evidence for a long range pseudoknot in the 5'-untranslated and matrix coding regions of HIV-1 genomic RNA," J. Biol Chem., vol. 277, No. 8, pp. 5995-6004 (Feb. 22, 2002).
Paillart et al., "Dimerization of retroviral RNA geomes: an inseparable pair," Nature Rev. Microbiol., vol. 2, pp. 461-472 (Jun. 2004).
Paillart et al., "First snapshots of The HIV-1 RNA structure in infected cells and in virions, " J. Biol. Chem., vol. 279, No. 46, pp. 48397-48403 (Nov. 12, 2004).
Peattie et al.. "Chemical probes for higher-order structure in RNA." Proceedings of the National Academy of Sciences, USA, vol. 77, No. 8, pp. 4679-4682 (Aug. 1980).
Perret et al., "Conformation in soltions of yeast tRNA(Aso) transcripts deprived of modified nucleotides," Biochimie, vol. 72, pp. 735-743 (1990).
Puglisi et al., "Conformation of the TAR RNA-arginine complex by NMR spectroscopy," Science, vol. 257, pp. 76-80 (Jul. 3, 1992).
Rein et al., "Nucleic-acid-chaperone activity of retroviral nucleocapsid proteins: significance for viral replication," Trends Biochem Sci., vol. 23, pp. 297-301 (1998).
Rein, "Take Two," Nature Struct. Mol. Biol., vol. 11, No. 11, pp. 1034-1035 (Nov. 2004).
Resnekov et al., "RNA secondary structure in an integral part of the in vitro mechanism of attenuation in simian virus 40," J. Biol Chem., vol. 264, No. 17, pp. 9953-9959 (Jun. 15, 1989).
Rice et al., "RNA secondary structure modeling at consistent high accuracy using differential SHAPE," RNA, vol. 20, No.6, pp. 846-854, and supplemental supporting information (6 pages), (2014).
Robins et al., "Syntheses of Puromycin from Adenosine and 7-Deazapuromycin from Tubercidin, and Biological Comparisons of the 7-Aza/Deaza Pair," Journal of Organic Chemistry. vol. 66, pp. 8204-8210 (2001).
Romby et al., "Comparison of the Tertiary Structure of Yeast tRNAAsp and tRNAPhe in Solution: Chemical Modification Study of the Bases," J. Mol Biol., vol. 195, pp. 193-204 (1987).
Rossio et al., "Inactivation of human immunodeficiency virus type 1 infectivity with preservation of conformational and functional integrity of virion surface proteins," J. Virol., vol. 72, No. 10, pp. 7992-8001 (1998).
Ryvkin et al., "HAMR: high-throughput annotation of modified ribonucleotides," rnajournal.cshlp.org, Cold Spring Harbor Laboratory Press for the RNA Society, RNA 19, pp. 1-9 (Oct. 22, 2013).
Siegfried et al., "RNA motif discovery by SHAPE and mutational profiling (SHAPE-MaP)," Nature Methods, vol. 11, No. 9, pp. 959-965 (Sep. 2014).
Soukup et al., "Relationship between internucleotide linkage geometry and the stability of RNA," RNA, vol. 5, pp. 1308-1325 (1999).
Stearns et al., "Synthesis and characterization of highly sensitive heparin probes for detection of heparin-binding proteins," Analyt. Biochem., vol. 247, pp. 348-356 (1997).
Thomas et al., "Human immunodeficiency virus type 1 nucleocapsid zinc-finger mutations cause defects in reverse transcription and integration," Virology, vol. 353, pp. 41-51 (2006).
Tinoco et al, "RNA structure from A to Z," Cold Spring Harbor Symp. Quant. Biol., pp. 135-146 (1987).
Tinoco et al, "How RNA Folds," J. Mol. Biol., vol. 293, pp. 271-281 (1999).
Tuerk et al., "CUUCGG hairpins: Extraordinarily stable RNA secondary structures associated with various biochemical processes," Proceedings of the National Academy of Sciences USA, vol. 85, pp. 1364-1368 (Mar. 1988).
Vasa et al., "ShapeFinder: a software system for high-throughput quantitative analysis of nucleic acid reactivity information resolved by capillary electrophoresis," RNA, vol. 14, pp. 1979-1990 (2008).
Velikyan et al., "The pKa's of 2-'Hydroxyl Group in Nucleosides and Nucleotides," J. Am. Chem. Soc., vol. 123, pp. 2893-2894 (2001).
Verheyden et al., "Synthesis of some pyrimidine 2'-amino-2'-deoxynucleosides," J. Org. Chem., vol. 36, No. 2, pp. 250-254 (1971).
Wang et al., "Complex ligand-induced conformational changes in tRNA(Asp) revealed by single-nucleotide resolution SHAPE chemistry," Biochemistry, vol. 47, pp. 3454-3461 (2008).
Westhof et al., "Crystallographic refinement of yeast aspartic acid transfer RNA," J. Mol. Biol., vol. 184, pp. 119-145 (1985).

(56) References Cited

OTHER PUBLICATIONS

Westhof et al., "Restrained refinement of two crystalline forms of yeast aspartic acid and phenylalanine transfer RNA crystals," Acta Cryst., vol. A44, pp. 112-123 (1988).
Williams et al., "Amplificaton of complex gene libraries by emulsion PCT," Nature Methods, vol. 3, No. 7, pp. 545-550 (Jul. 2006).
Wilkinson et al., "RNA SHAPE chemistry reveals nonhierarchical interactions dominate equilibrium structural transitions in tRNA(Asp) transcripts," J Am Chem Soc., vol. 127, pp. 4659-4667 (2005).
Wilkinson et al., "Selective 2'-hydroxyl acylation analyzed by primer extension (SHAPE): quantitative RNA structure analysis at single nucleotide resolution," Nature Protocols, vol. 1, No. 3., pp. 1610-1616 (2006).
Wilkenson et al., "High-throughput SHAPE analysis reveals structures in HIV-1 genomic RNA strongly conserved across distinct biological states," PLoS Biol., vol. 6, No. 4, e96, pp. 0883-0899 (Apr. 2008).
Wittberger et al., "Evaluation of uranyl photocleavage as probe to monitor ion binding and flexibility in RNAs," J. Mol. Biol., vol. 300, pp. 339-352 (2000).
Office Action corresponding to European patent application No. 14 851 697.7 dated May 18, 2018.
Office Action corresponding to Japanese patent application No. 2016-521773 dated Jun. 25, 2018.
Office Action corresponding to European patent application No. 14 851 691.7 dated Nov. 21, 2017.

\* cited by examiner

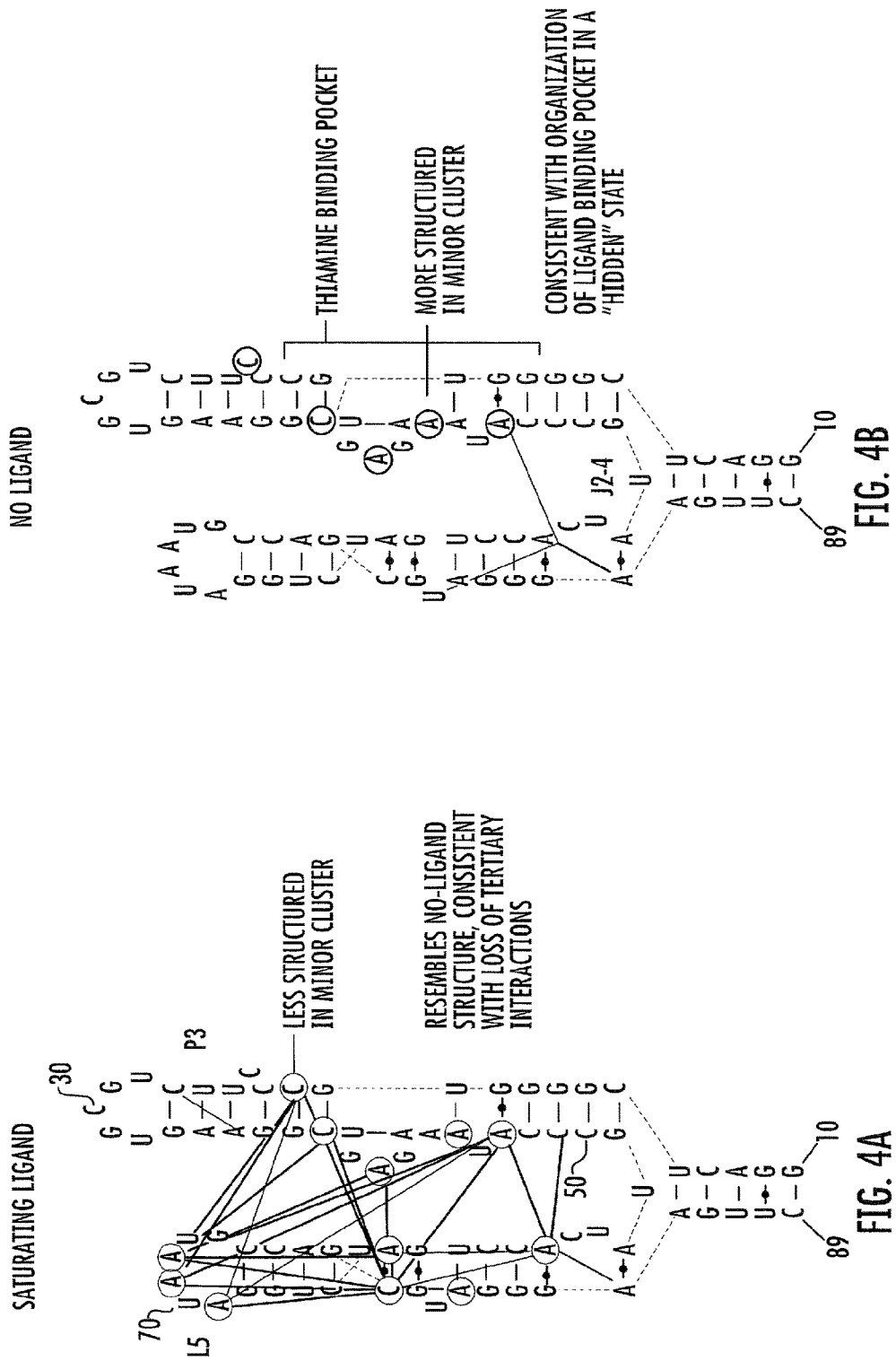

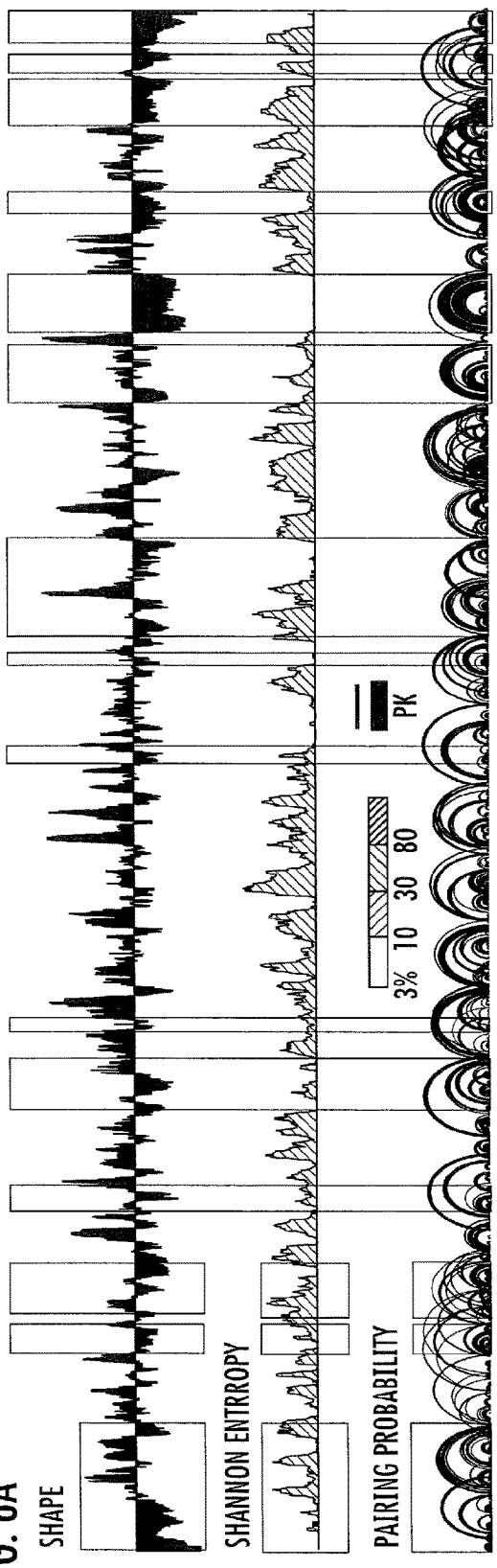
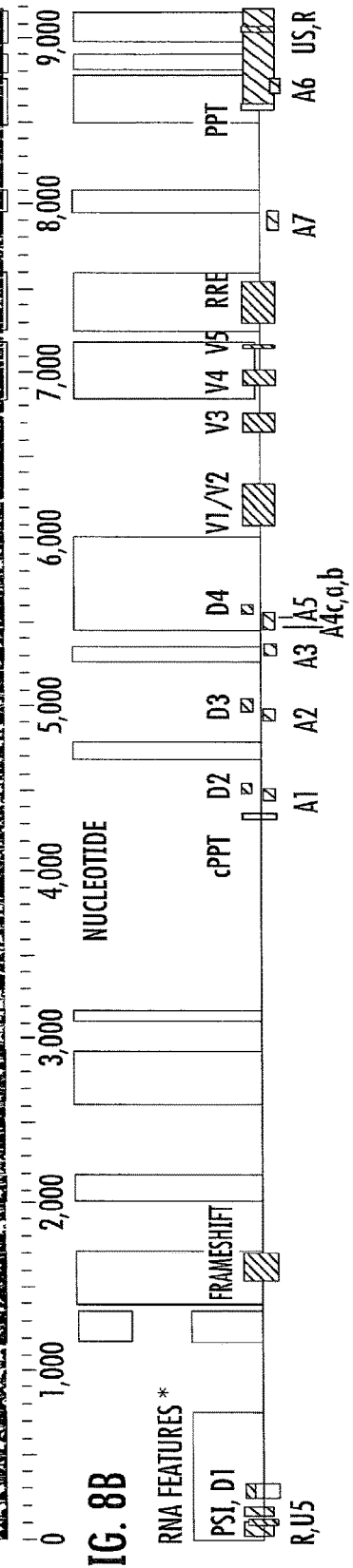
FIG. 8A
FIG. 8B

PRIMER DESIGN FOR RANDOMLY-PRIMED SHAPE-MaP

9-MER

5'-$N_1N_2N_3N_4N_5N_6N_7N_8N_9$-3'  9-MER PRIMERS ARE STANDARD RANDOM NONAMERS

LNA+

5'-$L_1X_2L_3X_4L_5X_6X_7X_8X_9X_{10}$-3'

$L_1, L_3, L_5$ = LOCKED (LNA) A, G OR T $X_2, X_4, X_{6-10}$ = 2,6-DIAMINOPURINE, dG OR dT

LNA+ PRIMERS ARE DESIGNED TO REDUCE SEQUENCING DEPTH SPREAD FOR RNAs WITH REGIONS OF LOW CG-CONTENT
- CYTOSINE IS OMITTED TO DISFAVOR BINDING TO GUANOSINE
- 2,6-DAP IS INCLUDED TO FAVOR BINDING TO URIDINE
- A, G, AND T LNAs FAVOR BINDING TO URIDINE, GUANOSINE, AND ADENINE

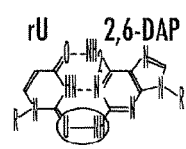

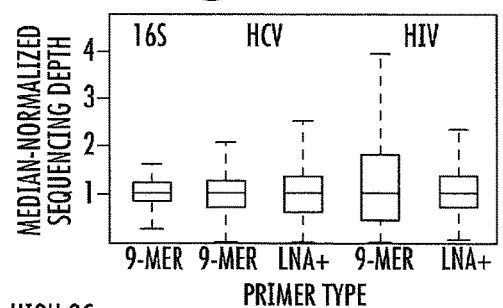

SEQUENCING DEPTH SPREAD IS:
- LOW OVER 16S RIBOSOMAL RNA USING 9-MER PRIMERS
- LOW OVER HCV GENOMIC RNA USING 9-MER PRIMERS, AND IS NOT IMPROVED USING LNA+ PRIMERS
- HIGH OVER HIV-1 GENOMIC RNA USING 9-MER PRIMERS, BUT IS NOTABLY IMPROVED USING LNA+ PRIMERS

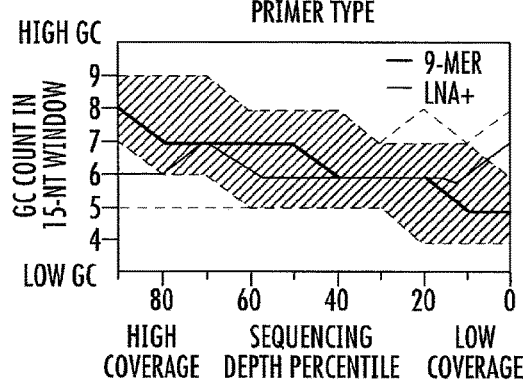

LNA+ PRIMERS SIGNIFICANTLY REDUCED SEQUENCING DEPTH BIAS AGAINST LOW-GC REGIONS IN HIV-1 RNA. MEDIAN GC COUNTS ARE SHOWN AS SOLID LINES AND INTERQUARTILE RANGES AS DASHED LINES

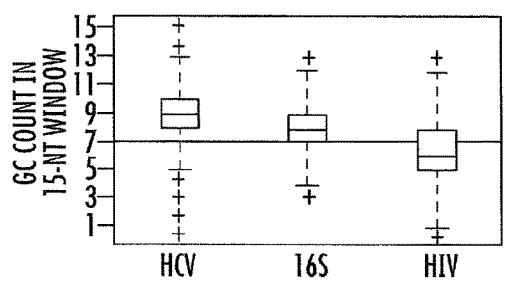

RULE: USE LNA+ PRIMERS FOR RNAs WITH 15-nt WINDOWED MEDIAN GC COUNTS BELOW 7.

FIG. 10

DETECTION OF CHEMICAL MODIFICATIONS IN NUCLEIC ACIDS

RELATED APPLICATIONS

This application is the U.S. National Stage of PCT International Application No. PCT/US2014/059489, filed Oct. 7, 2014; which is based on and claims the benefit of U.S. Provisional Patent Application Ser. No. 61/887,614, filed Oct. 7, 2013; the disclosure of which is incorporated herein by reference in its entirety.

GOVERNMENT INTEREST

The invention was made with government support under NIH Grant Nos. AI068462 and GM064803. The government has certain rights in the invention.

TECHNICAL FIELD

The presently disclosed subject matter relates to technology and methods for analyzing the structure of nucleic acid molecules, such as RNA molecules. More particularly, in some embodiments the presently disclosed subject matter is directed to methods of detecting chemical modifications in nucleic acids, such as RNA, such as chemical modifications that stabilize the fully folded and functional tertiary structure of the nucleic acid, such as RNA.

BACKGROUND

The biological function of nucleic acids, such as RNA, is mediated by their structures. For example, mRNA is generally thought of as a linear molecule which contains the information for directing protein synthesis within the sequence of ribonucleotides. Studies have revealed a number of secondary and tertiary structures in mRNA which are important for its function (Tinoco et al. (1987) *Symp. Quant. Biol.* 52:135). Secondary structural elements in RNA are formed largely by Watson-Crick type interactions between different regions of the same RNA molecule. Important secondary structural elements include intramolecular double stranded regions, hairpin loops, bulges in duplex RNA and internal loops. Tertiary structural elements are formed when secondary structural elements come in contact with each other or with single stranded regions to produce a more complex three dimensional structure.

Very little is known about the precise three dimensional structures of nucleic acids, including in particular RNA. However, there have been a number of research efforts which have shown that RNA structures, including single stranded, secondary and tertiary structures, have important biological functions beyond simply encoding the information to make proteins in linear sequences (Resnekov et al. (1989) *J. Biol. Chem.* 264:9953; Tinoco et al. (1987) *Symp. Quant. Biol.* 52:135; Tuerk et al. (1988) *PNAS USA* 85:1364; and Larson et al. (1987) *Mol. Cell. Biochem.* 74:5). Thus, the development of approaches for the evaluation of the structure of nucleic acid molecules, such as RNA, represents a current and ongoing need in the art.

SUMMARY

In accordance with some embodiments of the presently disclosed subject matter provided are methods for detecting one or more chemical modifications in a nucleic acid. In some embodiments, the method comprises providing a nucleic acid suspected of having a chemical modification; synthesizing a nucleic acid using a polymerase and the provided nucleic acid as a template, wherein the synthesizing occurs under conditions wherein the polymerase reads through a chemical modification in the provided nucleic acid to thereby produce an incorrect nucleotide in the resulting nucleic acid at the site of the chemical modification; and detecting the incorrect nucleotide.

In accordance with some embodiments of the presently disclosed subject matter provided are methods for detecting structural data in a nucleic acid. In some embodiments, the method comprises providing a nucleic acid suspected of having a chemical modification; synthesizing a nucleic acid using a polymerase and the provided nucleic acid as a temple, wherein the synthesizing occurs under conditions wherein the polymerase reads through a chemical modification in the provided nucleic acid to thereby produce an incorrect nucleotide in the resulting nucleic acid at the site of the chemical modification; detecting the incorrect nucleotide; and producing output files comprising structural data for the provided nucleic acid.

In some embodiments of the presently disclosed subject matter, the provided nucleic acid is RNA. In some embodiments, the methods comprise detecting two or more chemical modifications. In some embodiments, the polymerase reads through multiple chemical modifications to produce multiple incorrect nucleotides and the methods comprise detecting each incorrect nucleotide.

In some embodiments, the nucleic acid has been exposed to a reagent that provides a chemical modification or the chemical modification is pre-existing in the nucleic acid. In some embodiments, the pre-existing modification is a 2'-O-methyl group, and/or is created by a cell from which the nucleic acid is derived, such as but not limited to an epigenetic modification and/or the modification is 1-methyl adenosine, 3-methyl cytosine, 6-methyl adenosine, 3-methyl uridine, and/or 2-methyl guanosine.

In some embodiments, the reagent comprises an electrophile. In some embodiments, the electrophile selectively modifies unconstrained nucleotides in the RNA to form a covalent ribose 2'-O-adduct. In some embodiments, the reagent is 1M7, 1M6, NMIA, DMS, or combinations thereof. In some embodiments, the nucleic acid is present in or derived from a biological sample.

In some embodiments, the polymerase is a reverse transcriptase. In some embodiments, the polymerase is a native polymerase or a mutant polymerase. In some embodiments, the synthesized nucleic acid is a cDNA.

In some embodiments, detecting the incorrect nucleotide comprises sequencing the nucleic acid. In some embodiments, the sequence information is aligned with the sequence of the provided nucleic acid. In some embodiments, detecting the incorrect nucleotide comprises employing massively parallel sequencing on the nucleic acid. In some embodiments, the method comprises amplifying the nucleic acid. In some embodiments, the method comprises amplifying the nucleic acid using a site-directed approach using specific primers, whole-genome using random priming, whole-transcriptome using random priming, or combinations thereof.

In some embodiments, the method comprises facilitating the diagnosis or providing a prognosis of a disease or disorder in a subject through the detecting of the one or more chemical modifications. In some embodiments, the method comprises normalizing, comparing, and/or joining different data sets containing nucleic acid structural information, such as but not limited to RNA structural information. In some embodiments, the method comprises the structure comprises a primer binding site, a protein binding site, a small molecule binding site, or a combination thereof. In some embodiments, the method comprises analyzing nucleic acid structure in the presence and absence of a primer, a protein, a small molecule or a combination thereof to identify a primer binding site, a protein binding site, a small molecule binding site, or a combination thereof.

In accordance with some embodiments of the presently disclosed subject matter provided are computer program products comprising computer executable instructions embodied in a computer readable medium in performing steps comprising any method step of any embodiment of the presently disclosed subject matter. In accordance with some embodiments of the presently disclosed subject matter provided are nucleic acid libraries produced by any method of the presently disclosed subject matter.

In accordance with some embodiments of the presently disclosed subject matter provided are kits comprising at least one reagent for carrying out any embodiment of the presently disclosed subject matter; and optionally a container for the same. In some embodiments, the kit comprises instructions for carrying out an embodiment of the presently disclosed subject matter.

In accordance with some embodiments of the presently disclosed subject matter provided are any and all methods, devices, systems, kits, apparatuses, compositions and/or uses shown and/or described expressly or by implication in the information provided herewith, including but not limited to features that may be apparent and/or understood by those of skill in the art upon a review of the instant disclosure.

It is an object of the presently disclosed subject matter to provide methods for nucleic acid structure analysis, including RNA structure analysis.

An object of the presently disclosed subject matter having been stated hereinabove, and which is achieved in whole or in part by the presently disclosed subject matter, other objects will become evident as the description proceeds when taken in connection with the accompanying drawings as best described herein below.

BRIEF DESCRIPTION OF THE DRAWINGS

(FIG. 2A) RNA molecules experience local structural variations and 'breathing' in which regions of an RNA become reactive to a chemical probe in a correlated way. Nucleotides that interact show correlated reactivity. Statistical association analysis is used to detect and quantify the strengths of these interdependencies. (FIG. 2B) RNA molecules can adopt multiple conformations in solution. Spectral clustering analysis based on similarity of nucleotide reactivity patterns can be used to separate data on individual RNA stands into different conformations.

FIGS. 4A-4D. RINGs and clustering analysis of the TPP riboswitch (SEQ ID NO:5) in the presence and absence of TPP ligand. RING analysis in the presence of (FIG. 4A) saturating ligand and (FIG. 4B) absence of ligand. Strong and moderate internucleotide associations are shown. Nucleotides that are less or more structured in the minor, less populated, cluster are emphasized with open and closed spheres, respectively. Spectral clustering analysis in the (FIG. 4C) presence of saturating ligand and (FIG. 4D) absence of ligand. There are two clusters in each state. In the presence of saturating ligand, the major cluster corresponds to the fully folded riboswitch. In the absence of ligand, the major cluster reflects an unstructured state with few internucleotide interactions. The minor cluster in the saturating ligand sample is less structured than the major cluster and is similar to the no-ligand structure. The minor cluster in the no-ligand sample is more highly structured than the major cluster specifically in the region of the thiamine binding pocket (closed circles).

(FIG. 7A) Secondary structure modeling accuracies reported as a function of sensitivity (sens) and positive predictive value (ppv) for calculations performed without experimental constraints (no data), with conventional capillary electrophoresis (CE) data, and with SHAPE-MaP data obtained with the 1M7 reagent or with three-reagent differential (Diff) data. Results are shaded on a scale to reflect low to high modeling accuracy. (FIG. 7B) Relationship between sequencing read depth, hit level, and accuracy of RNA structure modeling. Model accuracy (vertical axis) is shown as the geometric average of the sens and ppv of predicted structures with respect to the accepted model. Boxplots summarize modeling the secondary structure of the 16S ribosomal RNA as a function of simulated SHAPE-MaP read depth. At each depth, 100 folding trajectories were sampled. The line at the center of the box indicates the median value and boxes indicate the interquartile range. Whiskers contain data points that are within 1.5 times the interquartile range and outliers are indicated with (+) marks. Hit level is the total signal above normalized background per transcript nucleotide.

FIGS. 8A-8C: SHAPE-MaP analysis of the HIV-1 NL4-3 genome. (FIG. 8A) SHAPE reactivities, Shannon entropy and pairing probability for the NL4-3 HIV-1 genomic RNA. Reactivities are shown as the centered 55-nt median window, relative to the global median; regions above or below the line are more flexible or constrained than the median, respectively. Arcs representing base pairs are labeled by their respective pairing probabilities. Areas with many overlapping arcs have multiple potential structures. Pseudoknots (PK) are indicated by black arcs. Data shown correspond to a single representative experiment; individual regions, including proposed pseudoknots, were confirmed by independent replicates. (FIG. 8B) RNA regions identified as having biological functions. Brackets enclose well-determined regions and are drawn to emphasize locations of these regions relative to known RNA features in the context of the viral genome. Regions correspond to low SHAPE-low Shannon entropy domains and are extended to include all intersecting helices from the lowest predicted free-energy secondary structure. Shown are 5' and 3' UTRs; splice acceptors and donors, respectively; polypurine tracts; variable domains; and the frameshift and RRE domains. These elements fall within regions with low SHAPE and low Shannon entropy much more frequently than expected by chance (p=0.002). (FIG. 8C) Secondary structure models for regions, identified de novo, with low SHAPE reactivities and low Shannon entropies. Nucleotides are shown by SHAPE reactivity and pseudoknotted structures are labeled.

FIG. 10. Primer design for SHAPE-MaP. Sequences with low or unevenly distributed GC-content benefit from the newly designed LNA-based primers used to analyze HIV-1 sequences in this work.

DETAILED DESCRIPTION

Figure 1:
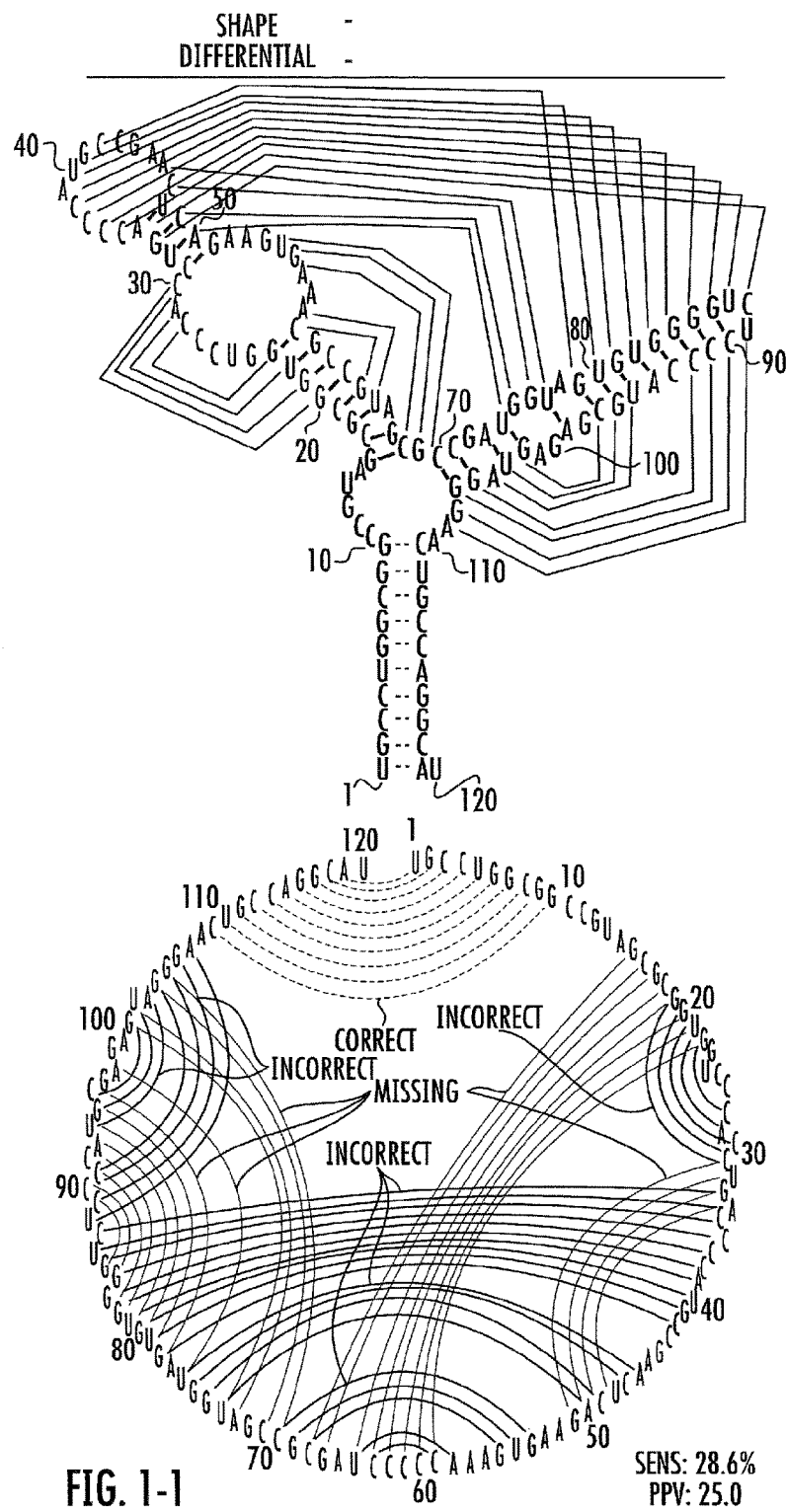
FIG. 1. Representative secondary structure modeling for the 5S rRNA (SEQ ID NO:1) without and with SHAPE data. Base pair predictions are illustrated with lines (denoting correct, incorrect, and missing base pairs, respectively) on conventional secondary structure representations (top) and circle plots (bottom). Nucleotides are colored according to their SHAPE reactivity on a black, light gray, dark gray scale for low, medium, and strong reactivity. Nucleotides showing strong preferential reactivity with NMIA (>0.3 units) are indicated with a delta symbol.
Figures 1, 2:
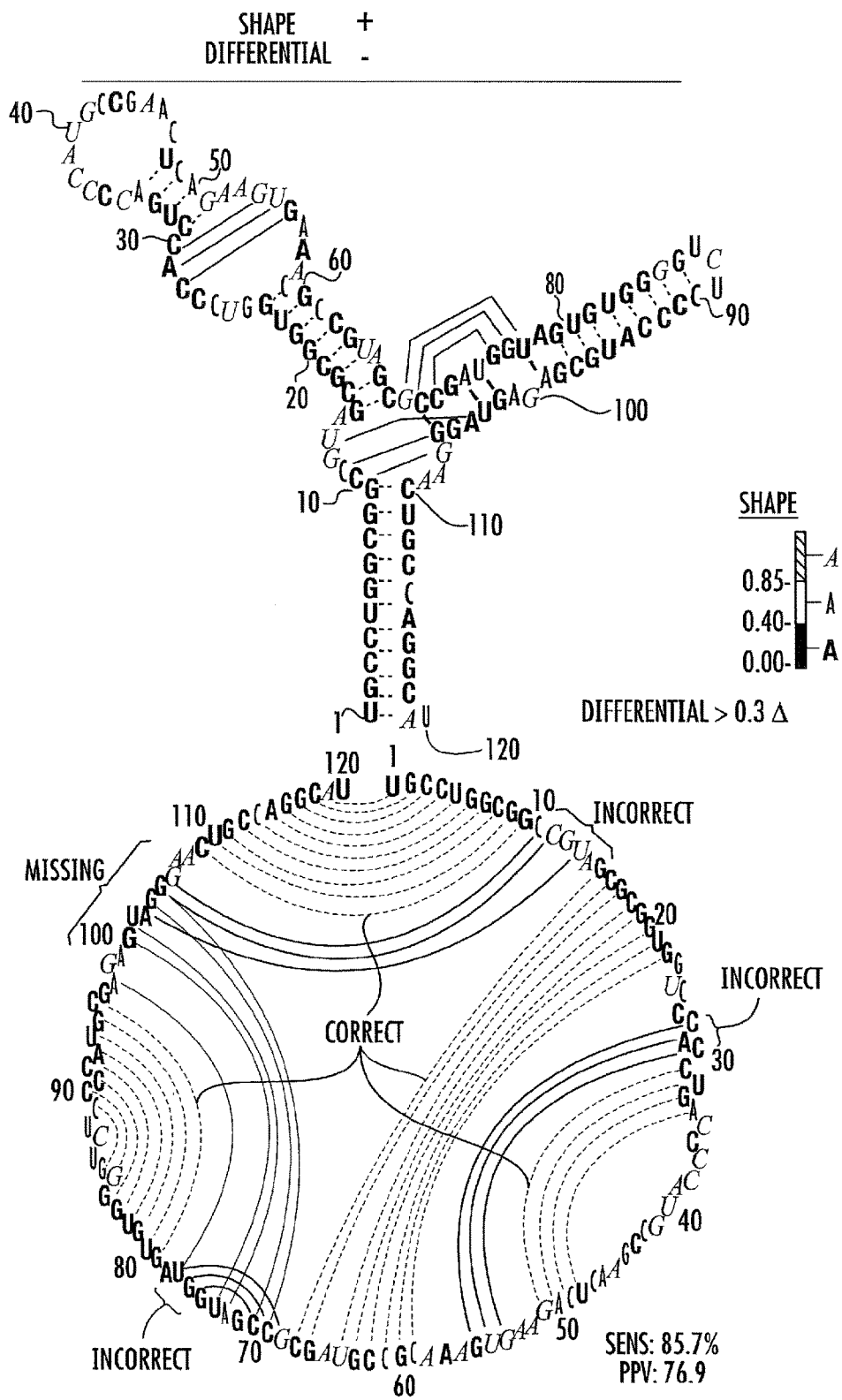
Figures 1, 2, 3:
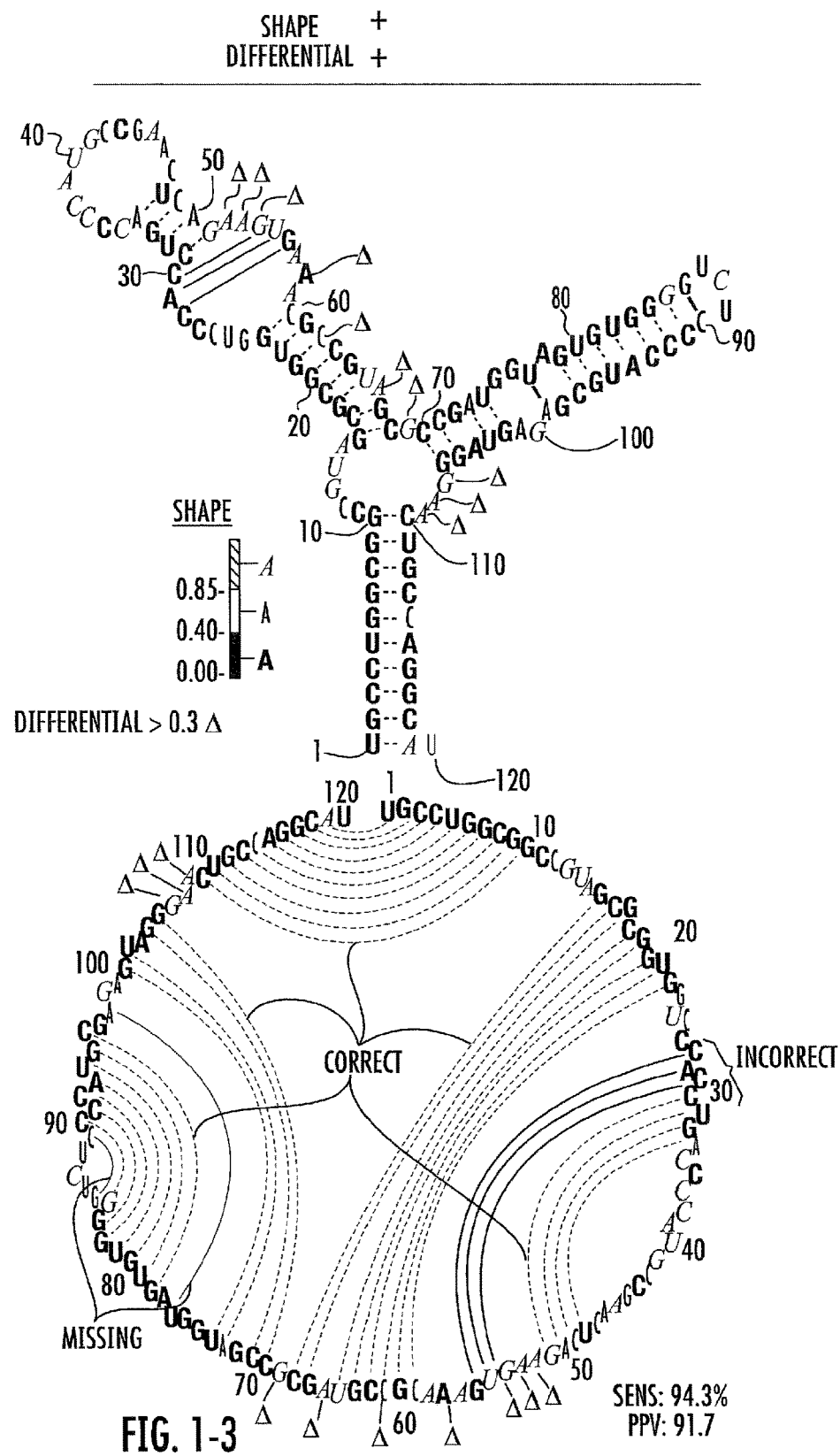

Nucleic acid structure modeling, such as RNA secondary structure modeling, is a challenging problem, and recent successes have raised the standards for accuracy, consistency, and tractability. Large increases in accuracy have been achieved by including data on reactivity toward chemical probes: Incorporation of 1M7 SHAPE reactivity data into an mfold-class algorithm results in median accuracies for base pair prediction that exceed 90%. However, many nucleic acid structures, including RNA structures, are modeled with significantly lower accuracy. Disclosed herein in some embodiments are approaches that incorporate differential reactivities from the NMIA and 1M6 reagents—which detect noncanonical and tertiary interactions—into prediction algorithms results in highly accurate secondary structure models for nucleic acids, such as RNAs, that were previously shown to be difficult to model. For example, for the RNAs, 93% of accepted canonical base pairs were recovered in SHAPE-directed models. Discrepancies between accepted and modeled structures were small and appear to reflect genuine structural differences. Three-reagent SHAPE-directed modeling scales concisely to structurally complex nucleic acids (including RNAs) to resolve the in-solution secondary structure analysis problem for many classes of nucleic acids, including RNA.

Complex nucleic acid structures, such as complex higher-order RNA structures, can play important roles in all facets of gene expression; however, the through-space interaction networks that define tertiary structures and govern sampling of multiple conformations are poorly understood. Disclosed herein in some embodiments are single-molecule nucleic acid structure analysis approaches, such as RNA structure analysis approaches, in which multiple sites of chemical modification are identified in single nucleic acid strands by massively parallel sequencing and then analyzed for correlated and clustered interactions. Thus, in some embodiments, the strategy identifies interaction groups by mutational profiling (RING-MaP) and makes possible multiple expansive applications. For example, disclosed herein in some embodiments is the identification and creation, through space interactions, of 3D models for nucleic acids, such as RNAs, spanning 80-265 nucleotides, and the characterization of broad classes of intramolecular interactions that stabilize nucleic acids, such as RNA. Additionally, disclosed herein in some embodiments are approaches that distinguish distinct conformations in solution ensembles and reveal previously undetected hidden states and large-scale structural reconfigurations that occur in unfolded nucleic acids, such RNAs, relative to native states. RING-MaP single-molecule nucleic acid structure interrogation enables concise and facile analysis of the global architectures and multiple conformations that govern function in nucleic acids, such as RNA.

Also disclosed herein in some embodiments are selective 2'-hydroxyl acylation analyzed by primer extension and mutational profiling (SHAPE-MaP) that makes possible de novo and large-scale identification of functional motifs in nucleic acids, such as RNA. In some embodiments, sites of 2'-hydroxyl acylation by SHAPE are encoded as non-complementary nucleotides during cDNA synthesis, as measured by massively parallel sequencing. For example, SHAPE-MaP-guided modeling identified greater than 90% of accepted base pairs in complex RNAs of known structure, and it was used to define a new model for the HIV-1 RNA genome. The HIV-1 model contains all known structured motifs and previously unknown elements, including experimentally validated pseudoknots. SHAPE-MaP yields accurate and high resolution secondary-structure models, enables analysis of low-abundance nucleic acids (including low abundance RNAs), disentangles sequence polymorphisms in single experiments and will ultimately democratize nucleic acid structure analysis, including RNA structure analysis.

The details of one or more embodiments of the presently disclosed subject matter are set forth in the accompanying description below. Other features, objects, and advantages of the presently disclosed subject matter will be apparent from the detailed description and claims. All publications, patent applications, patents, and other references mentioned herein are incorporated by reference in their entirety. Some of the polynucleotide and polypeptide sequences disclosed herein are cross-referenced to GENBANK® accession numbers. The sequences cross-referenced in the GENBANK® database are expressly incorporated by reference as are equivalent and related sequences present in GENBANK® or other public databases. Also expressly incorporated herein by reference are all annotations present in the GENBANK® database associated with the sequences disclosed herein. In case of conflict, the present specification, including definitions, will control.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

U.S. Pat. No. 8,318,424 is incorporated herein by reference in its entirety. All references cited herein are hereby incorporated by reference in their entirety.

I. Methods, Systems and Kits

Disclosed herein in some embodiments are methods employing next-generation (next-gen) sequencing with highly accurate nucleic acid analysis, such as RNA structure analysis. In some embodiments, provided are SHAPE-MaP methods. An example of such a method includes a method for detecting chemical modifications in RNA by reading through nucleotides containing an adduct and having a reverse transcriptase enzyme or other polymerase incorporate an incorrect (non-complementary) nucleotide at the site of the chemical modification. Another example of such a method includes a method for detecting chemical modifications in nucleic acids, such as RNA, by reading through nucleotides containing an adduct and having a mutant reverse transcriptase enzyme incorporate an incorrect (non-complementary) nucleotide at the site of the chemical modification. Another example of such a method includes a method for detecting chemical modifications to nucleic acids, such as RNA, using massively parallel sequencing. Another example of such as method is a method for detecting any arbitrary chemical modification to nucleic acids, such as RNA, using massively parallel sequencing and read out as sequence changes in the synthesized complementary nucleic acid, such as RNA.

Also disclosed herein is the use of SHAPE-MaP by the reagents 1M7, 1M6 and NMIA (exemplary embodiments set forth in the Examples). Indeed, provided in accordance with the presently disclosed subject matter is the use of SHAPE-MaP by any chemical agent.

Disclosed herein in some embodiments are RING-MaP methods. An example of such a method includes a method for detecting multiple chemical modifications in nucleic acids, such as RNA, by reading through multiple sites using reverse transcriptase or other polymerase to incorporate multiple non-complementary nucleotides, specifically at each site of mutation. An example of such a method includes a method for inferring nucleic acid, such as RNA, structure from detecting multiple chemical modifications in nucleic acids, such as RNA.

Also disclosed herein is the use of RING-MaP by DMS. Indeed, provided in accordance with the presently disclosed subject matter is the use of RING-MaP by any chemical agent.

As used herein and in the claims, the term "incorrect", with respect to incorporation of a nucleotide, refers to incorporating a nucleotide that is non-complementary (by the Watson-Crick rules; A-U, A-T, G-C) to the nucleotide present in the original sequence. It also includes small deletions in the sequence.

The subject matter described herein for RNA chemical modification analysis and/or RNA structure analysis includes kits for carrying out the methods and analysis. The subject matter described herein for RNA chemical modification analysis and/or RNA structure analysis includes diagnostic approaches and methods employing the analysis.

In some embodiments, the chemical modification is pre-existing in the nucleic acid, such as RNA, such as a 2'-O-methyl group. Thus, the chemical modification can be created by any chemical reagent, or can be created by the cell (in the case of an epigenetic modification), and in some embodiments, using native and/or mutant polymerases. Detecting an epigenetic modification can be employed in a diagnostic approach, for example. In some embodiments, the modification is 1-methyl adenosine and/or 3-methyl cytosine (both of which can be detected from DMS modification). Other epigenetic modifications are 6-methyl adenosine, 3-methyl uridine, 2-methyl guanosine, and others as would be apparent to one of ordinary skill in the art upon a review of the instant disclosure.

The subject matter described herein for nucleic acid, such as RNA, chemical modification analysis and/or nucleic acid, such as RNA, structure analysis can be implemented using a computer program product comprising computer executable instructions embodied in a computer-readable medium. Exemplary computer-readable media suitable for implementing the subject matter described herein include chip memory devices, disc memory devices, programmable logic devices, and application specific integrated circuits. In addition, a computer program product that implements the subject matter described herein can be located on a single device or computing platform or can be distributed across multiple devices or computing platforms. Thus, the subject matter described herein can include a set of computer instructions, that when executed by a computer, performs a specific function for nucleic acid, such as RNA, structure analysis.

The nucleic acid, such as RNA, can be present in a biological sample. The reagent-solvent solution is added to a complex biological solution containing nucleic acids, such as RNA. The solution can contain different concentrations and amounts of proteins, cells, viruses, lipids, mono- and polysaccharides, amino acids, nucleotides, DNA, and different salts and metabolites. The concentration of the reagent can be adjusted to achieve the desired degree of modification in the nucleic acids, such as RNA.

The term "aprotic solvent" refers to a solvent molecule which can neither accept nor donate a proton. Typical aprotic solvents include, but are not limited to, acetone, acetonitrile, benzene, butanone, butyronitrile, carbon tetrachloride, chlorobenzene, chloroform, 1,2-dichloroethane, dichloromethane, diethyl ether, dimethylacetamide, N,N-dimethylformamide (DMF), dimethylsulfoxide (DMSO), 1,4-dioxane, ethyl acetate, ethylene glycol dimethyl ether, hexane, N-methylpyrrolidone, pyridine, tetrahydrofuran (THF), and toluene. Certain aprotic solvents are polar solvents. Examples of polar aprotic solvents include, but are not limited to, acetone, acetonitrile, butanone, N,N-dimethylformamide, and dimethylsulfoxide. Certain aprotic solvents are non-polar solvents. Examples of nonpolar, aprotic solvents include, but are not limited to, diethyl ether, aliphatic hydrocarbons, such as hexane, aromatic hydrocarbons, such as benzene and toluene, and symmetrical halogenated hydrocarbons, such as carbon tetrachloride.

Continuing, the nucleic acids, such as RNA, can be modified in the presence of protein or other small and large biological ligands. Solution components that react directly with the electrophile as well as organic co-solvents, including for example formamide and DMSO, can be well tolerated but can require that reagent concentrations be adjusted. Because electrophile reactivity can be strongly dependent on pH, the pH can be maintained at any suitable range, such as but not limited to pH 7.5 to 8.0. The dynamic range that differentiates the most reactive (flexible) and least reactive (constrained) nucleotides typically spans a factor of 20-50.

Continuing, the nucleic acid can also be DNA. Applications could be detecting epigenetic modifications in DNA by use of a polymerase or reverse transcriptase that incorporates an incorrect or non-complementary nucleotide when synthesizing DNA past a chemical modification in the target DNA. Also, included are methods in which the DNA is a synthetic molecules, for example a DNA aptamer. In this embodiment, applying the SHAPE-MaP or RING-MaP method to DNA might be used as a diagnostic to detect a molecule or protein binding to DNA.

II. Shape Electrophiles

As disclosed herein in accordance with some embodiments of the presently disclosed subject matter, SHAPE chemistry takes advantage of the discovery that the nucleophilic reactivity of a ribose 2'-hydroxyl group is gated by local nucleotide flexibility. At nucleotides constrained by base pairing or tertiary interactions, the 3'-phosphodiester anion and other interactions reduce reactivity of the 2'-hydroxyl. In contrast, flexible positions preferentially adopt conformations that react with an electrophile, including but not limited to NMIA, to form a 2'-O-adduct. By way of example, NMIA reacts generically with all four nucleotides and the reagent undergoes a parallel, self-inactivating, hydrolysis reaction. Indeed, the presently disclosed subject matter provides that any molecule that can react with a nucleic acid as described immediately above can be employed in accordance with some embodiments of the presently disclosed subject matter.

Additional SHAPE reagents have been developed. The SHAPE reagents include, but are not limited to, isatoic anhydride derivatives. In some embodiments, the isatoic anhydride derivatives suitable for use with the SHAPE methodology are represented below, wherein X and Y can be any functional group, and the reactive carbon center is circled:

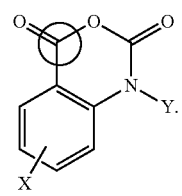

An adduct formed between an isatoic anhydride derivative and a RNA nucleotide can have the structure:

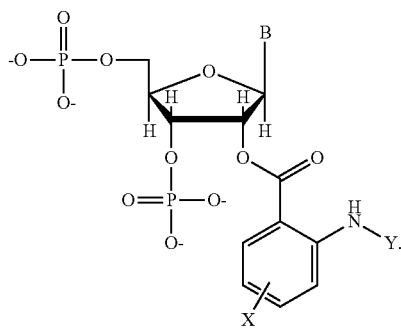

In some embodiments, the isatoic anhydride derivative can be 1-methyl-7-nitroisatoic anhydride (1M7):

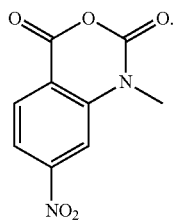 [SMILES: Cn1c(=O)oc(=O)c2ccc([N+](=O)[O-])cc21]

In some embodiments, the X substituent of the isatoic anhydride can be a functional group including, but not limited to, alkyl, substituted alkyl, cycloalkyl, aryl, substituted aryl, heteroaryl, alkoxyl, aryloxyl, aralkyl, aralkoxyl, dialkylamino, nitro, carboxyl, halo, acyl, hydroxyalkyl, aminoalkyl. In some embodiments, Y can be a functional group including, but not limited to, alkyl, substituted alkyl, cycloalkyl, aryl, substituted aryl, heteroaryl, hydroxyalkyl, and aminoalkyl.

A named "X", "Y", or in some cases "R" functional group will generally have the structure that is recognized in the art as corresponding to a group having that name, unless specified otherwise herein. For the purposes of illustration, certain representative named "X", "Y", or in some cases "R" functional groups are defined below. These definitions are intended to supplement and illustrate, not preclude, the definitions that would be apparent to one of ordinary skill in the art upon review of the present disclosure.

In addition to the molecules mentioned above, DMS can also be employed as a SHAPE reagent. Indeed, the presently disclosed subject matter provides that any molecule that can react with RNA or DNA to leave a permanent chemical modification can be employed, in accordance with some embodiments of the presently disclosed subject matter.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and alkenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

A structure represented generally by a formula such as:

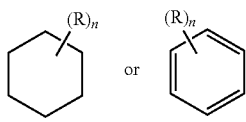

as used herein refers to a ring structure, for example, but not limited to a 3-carbon, a 4-carbon, a 5-carbon, a 6-carbon, and the like, aliphatic and/or aromatic cyclic compound comprising a substituent R group, wherein the R group can be present or absent, and when present, one or more R groups can each be substituted on one or more available carbon atoms of the ring structure. The presence or absence of the R group and number of R groups is determined by the value of the integer n. Each R group, if more than one, is substituted on an available carbon of the ring structure rather than on another R group. For example, the structure:

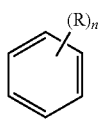

wherein n is an integer from 0 to 2 comprises compound groups including, but not limited to:

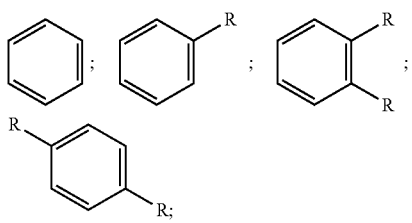

and the like.

In some embodiments, the compounds described by the presently disclosed subject matter contain a linking group. As used herein, the term "linking group" comprises a chemical moiety, such as a furanyl, phenylene, thienyl, and pyrrolyl radical, which is bonded to two or more other chemical moieties, in particular aryl groups, to form a stable structure.

When a named atom of an aromatic ring or a heterocyclic aromatic ring is defined as being "absent," the named atom is replaced by a direct bond. When the linking group or spacer group is defined as being absent, the linking group or spacer group is replaced by a direct bond.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

As used herein, the term "acyl" refers to an organic carboxylic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkoxyl" refers to an alkyl-O— group wherein alkyl is as previously described. The term "alkoxyl" as used herein can refer to, for example, methoxyl, ethoxyl, propoxyl, isopropoxyl, butoxyl, t-butoxyl, and pentoxyl. The term "oxyalkyl" can be used interchangably with "alkoxyl".

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Dialkylamino" refers to an —NRR' group wherein each of R and R' is independently an alkyl group and/or a substituted alkyl group as previously described. Exemplary alkylamino groups include ethylmethylamino, dimethylamino, and diethylamino.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group.

"Alkylcarbamoyl" refers to a R'RN—CO— group wherein one of R and R' is hydrogen and the other of R and R' is alkyl and/or substituted alkyl as previously described.

"Dialkylcarbamoyl" refers to a R'RN—CO— group wherein each of R and R' is independently alkyl and/or substituted alkyl as previously described.

"Acyloxyl" refers to an acyl-O— group wherein acyl is as previously described.

"Acylamino" refers to an acyl-NH— group wherein acyl is as previously described.

The term "amino" refers to the —NH$_2$ group.

The term "carbonyl" refers to the —(C=O)— group.

The term "carboxyl" refers to the —COOH group.

The terms "halo", "halide", or "halogen" as used herein refer to fluoro, chloro, bromo, and iodo groups.

The term "hydroxyl" refers to the —OH group.

The term "hydroxyalkyl" refers to an alkyl group substituted with an —OH group.

The term "aminoalkyl" refers to an alkyl group substituted with an —NH$_2$ group. Thus, an "aminoalkyl" group can be a NH$_2$(CH$_2$)$_n$ group, wherein n is an integer from 1 to 6 (i.e., 1, 2, 3, 4, 5, or 6).

The term "mercapto" refers to the —SH group.

The term "oxo" refers to a compound described previously herein wherein a carbon atom is replaced by an oxygen atom.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

When the term "independently selected" is used, the substituents being referred to (e.g., R groups, such as groups R$_1$ and R$_2$, or groups X and Y), can be identical or different. For example, both X and Y can be substituted alkyls, or X can be hydrogen and Y can be a substituted alkyl, or vice versa, and the like.

III. RNA Folding

The presently disclosed subject matter can be performed with RNA generated by methods including but not limited to in vitro transcription and RNA generated in cells and viruses. In some embodiments, the RNAs can be purified by denaturing gel electrophoresis and renatured to achieve a biologically relevant conformation. Further, any procedure that folds the RNA to a desired conformation at a desired pH (e.g., about pH 8) can be substituted. The RNA can be first heated and snap cooled in a low ionic strength buffer to eliminate multimeric forms. A folding solution can then be added to allow the RNA to achieve an appropriate conformation and to prepare it for structure-sensitive probing with an electrophile. In some embodiments, the RNA can be folded in a single reaction and later separated into (+) and (−) electrophile reactions. In some embodiments, RNA is not natively folded before modification. Modification can take place while the RNA is denatured by heat and/or low salt conditions.

IV. Agent for Polymerization

The agent for polymerization can be any compound or system that functions to accomplish the synthesis of a nucleic acid, including for example, enzymes. The polymerase can be a native polymerase and/or a mutant polymerase. Suitable enzymes for this purpose include, but are not limited to, E. coli DNA polymerase I, Klenow fragment of E. coli DNA polymerase, polymerase muteins, reverse transcriptase, other enzymes, including heat-stable enzymes, such as murine or avian reverse transcriptase enzymes.

The newly synthesized strand and its complementary nucleic acid strand can form a double-stranded molecule under hybridizing conditions described herein and this hybrid is used in subsequent steps of the method.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

SHAPE-MP Protocol

General Overview
1. A. SHAPE modification
   B. EtOH ppt/G25 or 50/RNEasy
2. A. Reverse transcription (3 hours, no Mg$^{2+}$, 6 mM Mn$^{2+}$) (OK to leave overnight)
   B. G25/50 spin column
3. A. 1$^{st}$ step PCR using GSP primers—only a few cycles (3)
   B. PCR clean up (PureLink™ PCR Micro clean up) (OK to freeze after, in sealed PCR plate)
4. A. 2$^{st}$ step PCR using pre-mixed, index specific primers—more cycles than previous step. (27)
   B. PCR clean up (PureLink™ PCR Micro clean up) (OK to freeze after, in sealed PCR plate)
5. Ampure™ Bead size selection
6. Bioanalyzer/Qubit analysis
7. Pool samples, sequence Material Requirements:
1. A. RNA (100 ng-1 ug*) (100 uL rxn)
   B. EtOH ppt/G25 or 50 column/RNEasy™ Kit
2. A. Reverse transcription (3 hours, no Mg$^{2+}$) (1-500 ng) (~20 uL)
   B. G25/50 spin column (50 uL output)
1. SHAPE Modification:

The following table outlines the modification process, compared to traditional SHAPE modification if a 100 uL volume after reaction is convenient for a purification plan. Only add water, ethanol and salt if ethanol precipitating is planned (not recommended). If the RNA is too small to use an RNeasy™ kit on (~200 bps) a spin column is much more efficient and provides a higher yield of RNA:

| | Normal SHAPE | SHAPE MP, +SHAPE | SHAPE MP, DMSO | SHAPE MP, DC Cntrl |
|---|---|---|---|---|
| Reagent | | | | |
| RNA | 1 uL | 1 uL | 1 uL | 1 uL |
| Folding Buffer | 3 uL | x uL | x uL | 89 uL of 50 mM HEPES, 4 mM EDTA, 50% formamide |
| H$_2$O | 5 uL | X uL | X uL | X uL |
| Total: | 9 uL | 90 uL | 90 uL | 90 uL |
| Step: | | | | |
| 1. Folding/Incubation | 37 deg, etc | 37 deg, etc | 37 deg, etc | 95 deg for 1 minute |
| 2. SHAPE Modification | 1 uL 10 mM | 10 uL 100 mM | 10 uL DMSO | 10 uL 100 mM |
| 3. Incubation | 5 half lives | 5 half lives | 5 half lives | 5 half lives |

-continued

|  | Normal SHAPE | SHAPE MP, +SHAPE | SHAPE MP, DMSO | SHAPE MP, DC Cntrl |
|---|---|---|---|---|
| 4. H$_2$O | 90 uL | — | — | — |
| 5. 4M NaCl | — | — | — | — |
| 6. EtOH | 400 uL | — | — | — |

If RNA is >200 bp, use RNeasy™ column to remove SHAPE reagent and small fragments, if smaller split into 2 50 uL aliquots and pass through G50 spin column. If necessary, combine and ethanol ppt. Re-suspend in an appropriate volume of water or Tris (pH 8.0).

2. Reverse Transcription, GSP (3 Hours, No Mg$^{2+}$):

This RT reaction is carried out for 3 hours at 42° C. in a buffer that contains no MgCl$_2$ but instead uses MnCl$_2$ as the activating divalent. For example, make 2× 421 buffer w/no Mg$^{2+}$, denoting this as 421$^-$, 2×.

First, make 10× First Strand Buffer:

| 5 mL | 1M Tris, pH 8 | (500 mM final) |
|---|---|---|
| 3.75 mL | 2M KCl | (750 mM final) |
| 1.25 mL | H$_2$O | |
| 10 mL | Total | |

DTT: Dilute a 1 M stock of DTT to 0.2 M
dNTPs: Make a mixture that is 20 mM in each
421$^-$, 2×:
 800 uL FSB; 10×
 400 uL 0.2 M DTT
 200 uL 20 mM dNTP mix
RT:
1-500 ng RNA; for example 150-500 ng
1 uL GSP Primer=2 pmol (RT primer)
Water to 11 uL
→65° C. for 5 minutes, then ice
3.5 uL 421$^-$, 2×
0.24 uL 500 mM Mn$^{2+}$
5.26 uL H$_2$O
→42° C. for 2 minutes
1 uL SSII
Incubate at 42° C. for 180 minutes
Incubate at 70° C. for 15 minutes
→Hold at 4° C.
Adjust to 50 uL, pass through a G50 column.
Elution is ~50 uL.
**Note: These volumes are meant to be flexible, if the RNA takes up a larger volume reduce the H$_2$O before or after the 421$^-$, 2× addition step. A master mix is usually made for consistency, avoiding the pipetting of 0.24 uL MnCl$_2$.

3. 1$^{St}$ Step PCR Using GSP Primers:

Reaction is carried out according to the directions for Phusion™ or Q5™ polymerase. Q5™ polymerase is better able to get through high GC content. Both are high-fidelity enzymes and will degrade single stranded primers if given enough time. As a result, it is suggested that the polymerase be added last then place reactions on a pre-heated thermocycler. Use an annealing temp calculated using the NEB primer calculator:
 http://www.neb.com/nebecomm/tech_reference/tmc-alc/#.UFYYxRgyHqs Since the final sample is the product of two PCR amplifications the total number of cycles desirably should not exceed 30 between the two. 15 cycles for have been used for each successfully. 2-3 uL of cDNA from the previous step have been used, but this can be varied. It is important to begin using ART tips at this point to avoid PCR contamination. Here is a typical 50 uL reaction:
Final Conc:
200 μM each dNTP
0.5 μM each primer
50-500 ng genomic template
1× Q5 Reaction Buffer
(1× High GC Enhancer—optional)
Denature at 98° C.
Extend 20 s/kb at 72° C.
1 unit Q5 High-Fidelity DNA Polymerase

| Reagent | Vol to Add (uL) | MM (___X) |
|---|---|---|
| Template | 15 | N/A |
| 5X Buffer | 10 | |
| 10 mM dNTPs | 1 | |
| 10 uM Primer A | 2.5 | N/A |
| 10 uM Primer B | 2.5 | N/A |
| GC Enhancer (Optional) | 10 | |
| H$_2$O | 8.5 | |
| Q5 Polymerase | 0.5 | |
| MM to each Rxn: | | N/A |

Reactions should be set up on ice. Following PCR, purify with a PureLink Micro PCR clean up kit. Elution is ~9-10 uL.

4. 2$^{st}$ Step PCR Using Pre-Mixed, Index Specific Primers:

This reaction adds the Illumina-specific sequences, including the index sequence, onto the ends of the DNA product. Use the pre-mixed 2$^{nd}$ step PCR primers. These primers are stored at a concentration of 10 uM, and are labeled by index number. Carry out the reaction exactly as above, using a 60 deg annealing temp.

| Reagent | Vol to Add (uL) | MM (___X) |
|---|---|---|
| Template | 10 | N/A |
| 5X Buffer | 10 | |
| 10 mM dNTPs | 1 | |
| 10 uM Primer A | 2.5 | N/A |
| 10 uM Primer B | 2.5 | N/A |
| GC Enhancer (Optional) | 10 | |
| H2O | 13.5 | |
| Q5 Polymerase | 0.5 | |
| MM to each Rxn: | N/A | 35 |

Purify with PureLink™ PCR clean up kit (non-micro). Elution is ~50 uL.

5. Ampure™ Bead Clean Up:

Allow Ampure™-XP beads to warm to room temperature. 1.8 mL aliquots of beads take about 15 minutes to reach this state. Make sure beads are well-mixed—vortex them. Transfer samples to a 96 well plate.

Prepare 80% ethanol fresh for this purification.
 1. Bead binding: Add 50 uL vortexed beads to 50 uL sample, pipette up and down 10 times to mix.
 2. Incubate on benchtop for 15 minutes at room temp.
 3. Place plate on 96 well magnetic stand. Leave for 5 minutes.
 4. Remove 95 uL of cleared supernatant from each sample, being careful to change tips. Leave the plate on the magnetic stand.
 5. Washing: Add 200 uL 80% ethanol without disturbing beads—pipette to the other side of the well.
 6. Allow to incubate for 30 seconds, then remove and discard all of the supernatant.

7. Repeat steps 5 and 6 so that the beads have been washed twice.
8. Leaving the plate on the magnetic stand, allow the beads to dry for 15 minutes. Place a large plastic lid over the plate to prevent dust and drafts from disturbing samples.
9. Elution of material: Remove plate from magnetic stand carefully, then resuspend beads in 32.5 uL of 10 mM Tris (pH 7.5-8.0).
10. Incubate at RT for 2 minutes. Place on the magnetic stand.
11. After 5 minutes remove 30 uL cleared supernatant and place in individual eppendorf tubes.

Example 2

SHAPE-MP Protocol

General Overview
1. A. SHAPE modification
   B. EtOH ppt/G25 or 50/RNEasy™
2. A. Fragment with 3×FSB
   B. G25/50 spin column
3. A. Reverse transcription (3 hours, no $Mg^{2+}$, 6 mM $Mn^{2+}$) (OK to leave overnight)
   B. G25/50 spin column
4. A. Second strand synthesis
   B. PCR clean up (PureLink™ PCR Micro clean up) (OK to freeze after, in sealed PCR plate)
5. A. End repair
   B. Ampure™ XP bead clean-up (OK to freeze after, in sealed PCR plate)
6. A. Addition of A overhang
   B. Ligation of forked adaptors
   C. Ampure™ XP bead clean up
   D. Ampure™ XP bead clean up
7. A. Emulsion PCR
   B. Ether extractions
   C. PCR clean up (PureLink™ PCR clean up)
8. Ampure™ Bead size selection
9. Bioanalyzer™/Qubit™ analysis
10. Pool samples, sequence Material Requirements:
1. A. SHAPE modification (100 ng-1 ug*) (100 uL rxn)
   B. G25 or 50 column/RNEasy™ Kit
2. A. Fragment with 3×FSB (50 uL rxn)
   B. G25/50 spin column (50 uL output)
3. A. Reverse transcription (3 hours, no $Mg^{2+}$) (1-500 ng) (~20 uL)
   B. G25/50 spin column (50 uL output)
4. A. Second strand synthesis (10-100 ng)
   B. PCR clean up (PureLink™ PCR Micro clean up) (10 uL out)
5. A. End repair (Output of previous)
   B. Ampure™ XP bead clean-up
6. A. Addition of A overhang (Output of previous)
   B. Ligation of forked adaptors
   C. Ampure™ XP bead clean up
   D. Ampure™ XP bead clean up (30 uL out)
7. A. Emulsion PCR (Varies, 7-30 uL of previous)
   B. Ether extractions
   C. PCR clean up (PureLink™ PCR clean up)
8. Ampure™ Bead size selection
9. Bioanalyzer™/Qubit™ analysis
10. Pool samples, sequence (Overall, 10 uL of 20 nM DNA)

*This amount has not been carefully probed to even lower limits, and it is expected that lower limits can be employed.

1. SHAPE Modification:

The RNA of interest is modified once using a 100 mM SHAPE reagent stock, 10 mM reagent final reaction conditions. For convenience 100 uL reaction volumes are used (10× normal SHAPE). Perform steps 4, 5 and 6 only if using ethanol ppt; if using G25/50 or RNEasy™ kits, adjust volume appropriately and use manufacturer's directions.

The denatured control is carried out in 50% formamide FINAL. Make a 3×DC control buffer that contains 150 mM HEPES and 12 mM EDTA, no formamide.

The following table outlines the modification process, compared to traditional SHAPE modification:

| Reagent | Normal SHAPE | SHAPE MaP, +SHAPE | SHAPE MaP, DMSO | SHAPE MaP, DC Cntrl |
|---|---|---|---|---|
| RNA | 1 uL | x uL | x uL | 1 uL |
| Folding Buffer | 3 uL | x uL | x uL | 50 mM HEPES 4 mM EDTA 50% formamide |
| $H_2O$ | 5 uL | X uL | X uL | X uL |
| Total: | 9 uL | 90 uL | 90 uL | 90 uL |

| Step: | Normal SHAPE | SHAPE MP, +SHAPE | SHAPE MP, DMSO | SHAPE MP, DC Cntrl |
|---|---|---|---|---|
| 1. Folding/Incubation | 37 deg, etc | 37 deg, etc | 37 deg, etc | 95 deg for 1 minute |
| 2. SHAPE Modification | 1 uL 100 mM | 10 uL of 100 mM SHAPE reagent | 10 uL of 100 mM SHAPE reagent | 10 uL of 100 mM SHAPE reagent |
| 3. Incubation | 5 half lives | 5 half lives | 5 half lives | 5 half lives |
| 4. $H_2O$ | 90 uL | — | — | — |
| 5. 4M NaCl | | — | — | — |
| 6. EtOH | 400 uL | — | — | — |

If RNA is >200 bp, use RNeasy™ column to remove SHAPE reagent, small fragments. If smaller, reduce rxn volume to 50 uL total and pass through G25 column. Ethanol ppt can be used, but takes longer and results in greater sample loss.

2. Fragment with 3×FSB:

Fragmentation is carried out with 9 mM $Mg^{2+}$ as the functional divalent; this is equivalent to 3×FSB supplied with the superscript enzymes. For example, use a 4-minute incubation at 94° C. This digestion is carried out in a PCR plate so all samples can be heated for exactly the same amount of time.

Protocol:

Create a PCR program with a heated lid to incubate for the selected time, placing a 94° C. hold step first, ending with a 4° C. hold. Try to be there when the digestion time is done to place plate on ice immediately.

x uL RNA

Y uL 5×FSB (FSB+$Mg^{2+}$)—supplied with SS enzymes

If needed, adjust volume to 50 uL total volume with water, pass through G25/50 spin column. Elution is ~50 uL.

3. Reverse Transcription (3 Hours, No $Mg^{2+}$):

This RT reaction is carried out for 3 hours at 42° C. in a buffer that contains no $MgCl_2$ but instead uses $MnCl_2$ as the activating divalent. For example, make 2×421 buffer w/no $Mg^{2+}$, optionally denoting this as 421⁻, 2×.

First, make 10× First Strand Buffer:

| 5 mL | 1M Tris, pH 8 | (500 mM final) |
|---|---|---|
| 3.75 mL | 2M KCl | (750 mM final) |
| 1.25 mL | H$_2$O | |
| 10 mL | Total | |

DTT: Dilute a 1 M stock of DTT to 0.2 M
dNTPs: Make a mixture that is 20 mM in each
421⁻, 2×:
  800 uL FSB, 10×
  400 uL 0.2 M DTT
  200 uL 20 mM dNTP mix
RT:
1-500 ng RNA; I've used 150-500 ng
1 uL Random nonamers (50-250 ng)—I use 200 ng
Water to 11 uL
→65° C. for 5 minutes, then ice
3.5 uL 421⁻, 2×
0.24 uL 500 mM Mn$^{2+}$
5.26 uL H$_2$O
→25° C. for 2 minutes
1 uL SSII
→25° C. for 10 minutes
Incubate at 42° C. for 180 minutes
Incubate at 70° C. for 15 minutes
→Hold at 4° C.
Adjust to 50 uL, pass through a G25 column.
Elution is ~50 uL.
**Note: These volumes are meant to be flexible, if the RNA takes up a larger volume reduce the H$_2$O before or after the 421⁻, 2× addition step. A master mix is usually made for consistency, avoiding the pipetting of 0.24 uL MnCl$_2$.

4. Second Strand Synthesis:

Using the RNA/DNA hybrid from the previous step, a second strand of DNA is created and nicks in the DNA are repaired, for example, using a kit from NEB—#E6111S/L. Input DNA is 10-100 ng of first strand DNA in 20 uL volume. The protocol's next step adds 48 uL H$_2$O, believed to be for diluting buffer remaining from the RT reaction. Since there is none, input is 10-100 ng in 68 uL H$_2$O.
Add:
68 uL DNA/RNA
8 uL 10× Second Strand Synth. Buffer
4 uL Enzyme mix
80 uL total volume
Mix and incubate at 16° C. for 2.5 hours. Purify with a PureLink™ Micro PCR clean up kit. Elution is ~9-10 uL.

5. End Repair:

From this point forward use a 96-well PCR plate, for example one row at a time; carry out reactions in one, bead purify, then move to the next row. Seal up the previously used wells to avoid cross-contamination. Plates are expensive, but allow for the treatment of all samples most similarly and are the most amenable to fast bead separation. This step removes overhanging edges, fixes cyclic phosphates and prepares the dsDNA for subsequent ligation steps. The resulting dsDNA has blunt ends.

The NEBNext End Repair Module (E6050 S or L) suggests using a 100 uL reaction (total vol) for 1 to 5 ug of fragmented DNA. For example, use a 50 uL reaction for 0.5 to 2.5 ug of theoretical input fragmented DNA. Take out Ampure™ XP beads and allow them to reach room temp for 30 minutes. Mix the following:

X uL dsDNA
5 uL NEBNext™ End Repair Buffer (10×)
2.5 uL NEBNext™ Enzyme Mix
x uL H$_2$O
50 uL total volume
Incubate at 20° C. for 30 minutes. Adjust to 100 uL by adding 50 uL of Tris (pH 8.0).
  1. Add 160 uL of Ampure XP beads, adjust pipette to 200 uL, mix up and down 10×. Incubate at RT for 15 minutes.
  2. Place plate on magnetic stand, wait 5 minutes then remove and discard 127.5 uL cleared supernatant.
  3. Repeat step 2 once, leave plate on magnetic stand.
  4. Add 200 uL freshly made 80% EtOH to each well, do not wash over beads.
  5. Wait 30 seconds, remove all supernatant, repeat once for 2 washes.
  6. Leave plate on magnetic stand for 15 minutes to dry beads.
  7. Remove plate from magnetic stand, add 17.5 uL 10 mM Tris, pH 8.0 and resuspend beads. Incubate resuspended beads for 2 minutes at RT.
  8. Place plate on magnetic stand, wait 5 minutes, remove 15 uL and place in new wells.

6. End Tailing:

NEBNext dA-tailing module E6053 S/L, 1-5 ug of end repaired, blunt DNA (100-1000 bp). Mix:
15 uL DNA
2.0 uL 10× dA Tailing buffer
1.2 uL Klenow Fragment
1.8 uL Water
20.0 uL Total volume
Incubate for 30 minutes at 37° C. in a thermocycler. Proceed to ligation OR carry out bead purification (adding 1.8 volume beads). Elute in 23 uL water or 10 mM Tris (pH 8.0). Run 1 uL on a Agilent™ bioanalyzer chip (high sensitivity DNA) to determine relative concentration of adaptor to use in ligation. It is likely that a much smaller amount of adaptor could be used in the following step as compared to that suggested by the manufacturer Illumina.

7. Adaptor Ligation:

Mix the following:
20.0 uL of DNA from the previous step
7.5 uL of NEBNext Quick Ligation Rxn Buffer (5×) (NOT 2×)
2.5 uL of DNA adaptor
3.75 uL of Quick T4 DNA Ligase
3.75 uL of H$_2$O
37.5 uL Total Vol
Incubate for 15 minutes at 20° C. Add 5 uL H$_2$O to bring volume to 42.5 uL total. Proceed to Ampure™ XP bead clean-up.

First Clean-Up:
1. Add 42 uL of beads to each sample
2. Adjust pipette to 85 uL and mix each sample 10 times
3. Incubate for 15 minutes at room temp
4. Place plate on magnetic stand and allow to settle for 5 minutes
5. Remove 79.5 uL of supernatant and discard
6. Add 200 uL of freshly made 80% ethanol to each well
7. Allow beads to incubate for 30 seconds
8. Remove all supernatant and discard
9. Repeat steps 6-8 one more time (two washes)
10. Allow the beads to dry for 15 minutes on the magnetic stand
11. Remove from stand, resuspend in 52.5 uL of water or 10 mM Tris
12. Incubate for 2 minutes at room temp 13. Place on magnetic stand for 5 minutes
14. Remove 50 uL of supernatant from each sample and place in a new well in the 96-well plate.

Second Clean-Up:
1. Add 50 uL of beads to each sample
2. Adjust pipette to 100 uL and mix each sample 10 times
3. Incubate for 15 minutes at room temp
4. Place plate on magnetic stand and allow to settle for 5 minutes
5. Remove 95 uL of supernatant and discard
6. Add 200 uL of freshly made 80% ethanol to each well
7. Allow beads to incubate for 30 seconds
8. Remove all supernatant and discard
9. Repeat steps 6-8 one more time (two washes)
10. Allow the beads to dry for 15 minutes on the magnetic stand
11. Remove from stand, resuspend in 22.5 uL of water or 10 mM Tris
12. Incubate for 2 minutes at room temp
13. Place on magnetic stand for 5 minutes
14. Remove 20 uL of supernatant from each sample and place in small eppendorf tubes.

8. Emulsion PCR:

This step amplifies the cDNA libraries in a manner that largely prevents recombination events. Creating an emulsion of aqueous PCR reaction in a oil-detergent mixture creates millions of little bubbles that act as small reaction chambers. As a result few recombinations occur. Protocol is carried out according to Williams et al (Nature Methods vol. 3 no. 7, 2006 pg 545), prepare oil mixture as described.

Changes to this protocol:
1. Use Q5™ polymerase, not Pfu. Accordingly, use Q5™ primer and dNTP concentrations as well as Q5™ cycling conditions.
2. Unless using hot start Q5™ add the enzyme immediately prior to dripping your aqueous phase into your emulsion mix. This will prevent polymerase-mediated degradation of your primers.
3. Use a 95° C. denaturation step during your cycles.
4. Prior to using the speed vac place tubes, open, in a ~65° C. heat block for ~5 minutes to drive off extra ether.

A 1×rnx using Q5 (in this case no GC enhancer was used):
10 uL DNA Template
52 uL Q5 Buffer
26 uL BSA
13 uL Primer 1
13 uL Primer 2
5.2 uL dNTPs (10 mM)
2.6 uL Q5 Polymerase
138.2 uL H$_2$O A master mix excluding DNA template and enzyme should be made. Purification of the broken, speed-vac'ed emulsions is done using a PureLink™ PCR clean up kit (non-micro). A final bead clean-up is carried out using a 1 to 1 volume of sample:beads (Illumina protocol) or the larger volume Iowa protocol.

Ampure Cleanup—Amplicons—Iowa Protocol
1. Bring Ampure™ XP beads to Room Temperature.
2. Prepare fresh 70% EtOH (Need ~3 ml per sample).
3. Bring DNA volume to 45 ul in TE/EB (~200 ng enough) in a 1.5 ml low-bind tube.
4. Mix Ampure™ XP beads well and add 72 ul beads to the 45 ul DNA (1.6:1.0 ratio).
5. Vortex, spin down and incubate at Room Temp for 5 minutes.
6. Place on magnetic stand (Suggested: Invitrogen Dynal™, Red-Silver).
7. Wait for pellet to form and remove supernatant.
8. Add 500 ul of 70% EtOH to the side opposite the magnet (do not disturb beads).
9. Wait 30 seconds and remove the EtOH.
10. Repeat steps 8-9 one more time.
11. Allow the beads to dry completely (can remove from the magnet and place on 37 C heat block for 3-4 minutes). Sometimes there will be visible cracks in the pellet when it is dry.
12. To elute add 45 ul TE (or Qiagen EB), vortex, spin down and place on the magnetic stand.
13. After the pellet is formed transfer the 45 ul with the eluted DNA into a new tube.
14. Repeat steps 4-13 one or two more times.
15. Run 1 ul on the Agilent™ Bioanalyzer (DNA High Sensitivity chip).

Example 3

RNA Secondary Structure Modeling at Consistent High Accuracy Using Differential SHAPE RNA is a central information carrier in biology (Sharp 2009). Information is encoded in RNA at two distinct levels: in its primary sequence and in its ability to fold into higher order structures (Leontis et al. 2006; Dethoff et al. 2012). The most fundamental level of higher order structure is the pattern of base-pairing or secondary structure. Defining the secondary structure of an RNA is also a important first step in tertiary structure modeling (Hajdin et al. 2010; Weeks 2010; Bailor et al. 2011). The structures of RNA molecules modulate the numerous functions of RNA and the interactions of RNAs with proteins, small molecules, and other RNAs in splicing, translation, and other regulatory machineries (Mauger et al. 2013). Accurate, de novo modeling of RNA secondary structure is challenging: In the absence of experimental restraints, current algorithms predict base-pairing patterns that contain, on average, 50%-70% of the canonical (G-C, A-U, and G-U) pairs in secondary structures established through phylogenetic analysis or high-resolution experimental methods (Mathews et al. 2004; Hajdin et al. 2013). The modeling challenge results from the fact that there are only four RNA nucleotides; and these nucleotides have the potential to arrange into many, often energetically similar, RNA secondary structures, although many RNAs adopt a few or only single structures (Tinoco and Bustamante 1999). Features that are difficult to extract solely from the sequence—such as kinetic pathways, protein facilitators, and ligand binding—also influence RNA folding.

Identification of the correct RNA secondary structure also becomes much more difficult as the length of the RNA increases. Selective 2'-hydroxyl acylation analyzed by primer extension (SHAPE) reagents can be used to interrogate the flexibility of nearly every nucleotide in an RNA (Merino et al. 2005; McGinnis et al. 2012). Reactivity at the 2'-hydroxyl toward the reagent 1-methyl-7-nitroisatoic anhydride (1M7) measures local nucleotide flexibility. Because base-paired nucleotides are also structurally constrained, SHAPE reactivity is roughly inversely proportional to the probability that a nucleotide is paired. Incorporation of SHAPE reactivity information into RNA folding algorithms results in accuracies >90% for most RNAs including those with single pseudoknots (Deigan et al. 2009; Hajdin et al. 2013). SHAPE has been used to create nucleotide-resolution models for the viral genomes of HIV-1 (Watts et al. 2009) and STMV (Archer et al. 2013) and to analyze conformational changes in HIV-1 (Wilkinson et al. 2008)

and the Moloney murine leukemia virus (Grohman et al. 2013). Although SHAPE-directed folding yields near-perfect models for many RNAs, there remain a few RNAs whose structures are difficult to recover using a single structure probing experiment (Cordero et al. 2012; Leonard et al. 2013). These "hard" RNAs are modeled with sensitivities in the 75%-85% range.

The usefulness of secondary structure models at different accuracies can be summarized as follows. Models with prediction sensitivities <60% contain large errors in gross structure and are not generally useful for generating biological hypotheses. Computational-only algorithms achieve median prediction accuracies of ~70%. An individual model that recovers 70% of the accepted base pairs will have some correct helices and also critical errors. Although approaches that recover 70% of the accepted base pairs include both correct and incorrect pairs, it is generally difficult to determine which helices are correct and which are not. Using SHAPE-directed modeling, the predicted structures for the most challenging RNAs contain 80%-85% of accepted base pairs. In some cases, the incorrectly predicted base pairs are scattered throughout the RNA such that the overall model is quite good. In other cases, errors are located in structural elements that are known to be functionally important.

On average, SHAPE-directed modeling currently recovers ~93% of accepted base pairs in challenging sets of RNA molecules. This level of sensitivity is sufficient for generation of robust biological hypotheses and for three-dimensional structure modeling. Many of the models generated at this level of accuracy differ from the accepted models by a few base pairs and should be considered nearly perfect. Improving accuracies to the >90% level for all RNAs is the current challenge in experimentally directed secondary structure modeling. Inclusion of additional comprehensive and information-rich biochemical information could further inform and potentially solve the RNA secondary structure modeling problem.

An approach referred to herein as "differential" SHAPE reveals local noncanonical and tertiary structure interactions based on simple biochemical probing experiments. In this strategy, the position-specific reactivities of two reagents, N-methylisatoic anhydride (NMIA) and 1-methyl-6-nitroisatoic anhydride (1M6), are compared. The first reagent, NMIA, has a relatively long half-life in solution and reacts preferentially with nucleotides that experience slow dynamics. Often these nucleotides are in the rare C2'-endo ribose conformation and have been implicated as molecular timers capable of governing folding in large RNAs (Gherghe et al. 2008; Mortimer and Weeks 2009). For the second reagent, the nitro group of 1M6 makes the two-ring system electron poor, and this reagent is able to stack with RNA nucleobases that are not protected by interactions with other nucleotides in an RNA structure (Steen et al. 2012). This conformation is unusual since most nucleobases stack with other bases on both faces (Leontis et al. 2006). By taking the difference in reactivity profiles for these two 2'-hydroxyl selective reagents, nucleotides involved in structurally distinctive interactions within an RNA structure can be identified. Because the differential SHAPE analysis is specifically sensitive to noncanonical and tertiary interactions in RNA (Steen et al. 2012), this approach can help to identify nucleotides that are constrained (and thus unreactive to 1M7-SHAPE) but do not participate in canonical base-pairing.

Provided herein in accordance with aspects of the presently disclosed subject matter is a pseudo-free energy term that includes information from the slow and stacking differential SHAPE reactivities to yield nearly perfect secondary structure models in a concise experiment that scales to RNAs of any size.

Results

Selection of a Challenging Test Set.

To evaluate the utility of incorporating differential SHAPE data into a modeling algorithm, a set of diverse RNAs with well-established secondary structures for which single-reagent SHAPE-directed secondary structure prediction remains challenging (Table 1) were chosen. These included six riboswitch aptamer domains that require ligand binding to fold into their accepted structures (the TPP, adenine, glycine, cyclic-di-GMP, M-Box, and lysine riboswitches); four RNAs longer than 300 nucleotides (nt), including several domains of the Escherichia coli 16S and 23S ribosomal RNAs; four pseudoknot-containing RNAs; and every other RNA of which we are aware that contains up to one pseudoknot for which the single-reagent 1M7 modeling accuracy is <90% (Cordero et al. 2012; Hajdin et al. 2013; Leonard et al. 2013; Table 1).

Incorporation of Differential SHAPE into Secondary Structure Modeling.

SHAPE experiments were performed with 1M7, NMIA, and 1M6 on RNAs preincubated in the presence of cognate ligand if appropriate but without protein. Based on pilot work on three short RNAs, SHAPE reactivity signals from NMIA and 1M6 correlate strongly at most positions (Steen et al. 2012). A windowed scaling algorithm was employed to locally normalize NMIA and 1M6 SHAPE profiles to each other (see Materials and Methods, herein below) and then subtracted the normalized profiles to generate differential SHAPE reactivity traces.

We used a statistical potential approach (Rohl et al. 2004; Cordero et al. 2012) to evaluate the differential SHAPE signals. This approach infers a free energy from the difference in the distributions of paired and non-paired nucleotides. The energy function was linear and proved robust when subjected to a leave-one-out jackknife analysis. During fitting, negative differential signals from NMIA and 1M6 were evaluated. The negative-amplitude signal from 1M6 was not as highly correlated with single-stranded character at the sites of differential reactivity as was the positive-amplitude signal. Normalized SHAPE reactivities from reactions with NMIA and 1M6 were evaluated and differential SHAPE reactivities (Steen et al. 2012) were calculated by first scaling 1M6 to NMIA reactivities over a moving window and then subtracting 1M6 from NMIA reactivities. Strong differential reactivity enhancements (>|0.3| SHAPE units) were observed for NMIA and for 1M6. These sites correspond to nucleotides with slow dynamics and those with a face available for stacking, respectively. Nucleotide positions showing strong positive-amplitude (favoring NMIA) differential reactivities included positions 53, 58, 62, 66, 69 and 108.

The differential reactivity pseudo-free energy change term for each nucleotide was taken as:

$$\Delta G_{Diff} = d \times (\text{positive amplitude differential signal}), \quad (1)$$

where d is 2.11 kcal/mol. This energy penalty was added to the standard 1M7-based pseudo-free energy as implemented in ShapeKnots (Low and Weeks 2010; Hajdin et al. 2013); inclusion of this penalty improved predictions for many RNAs. For each RNA model, the accuracy of a secondary structure prediction in terms of its sensitivity (sens; fraction of base pairs in the accepted structure predicted correctly)

and positive predictive value (ppv; the fraction of predicted pairs that occur in the accepted structure) is reported in Table 1.

Impact of $\Delta G_{Diff}$ on Structure Modeling.

In the absence of experimental restraints, the mfold algorithm predicts only 10 of the 35 base pairs (29%) in the accepted structure of the E. coli 5S rRNA (SEQ ID NO:1; FIG. 1, left). Addition of 1M7-SHAPE constraints yielded a substantial improvement: 86% of the accepted base pairs were present in the SHAPE-directed model. As is common for predictions at this level of accuracy, most of the structure is modeled correctly. The exceptions are base pairs in one element, a helix at a three-way junction (FIG. 1, middle structure, positions 102-107). When differential SHAPE data were added as constraints, a substantially improved structural model was obtained (FIG. 1, right). The errors in the differential SHAPE based model are minor and involve the addition of a few base pairs in the second helix of the structure near nucleotide 30. These base pairs may in fact form under the probing conditions, given that this RNA was probed in the absence of ribosomal subunits and proteins.

Addition of differential SHAPE information also improved the accuracy of prediction of the glycine riboswitch structure (SEQ ID NO:2). With data from 1M7 only, the predicted model for the glycine riboswitch had 55% sens and 49% ppv. The major error in the model is the prediction of a false pseudo knot that then propagates other errors. Inclusion of the differential SHAPE penalty resulted in sens and ppv of 95%. In this case, use of the differential reactivity penalty corrected major errors (for example, the differential reactivities at positions 12-13 and 112) and eliminated the false positive pseudoknot. In addition, lower magnitude differential reactivities shifted the folding landscape of nucleotides 39-49 to result in agreement of the predicted and accepted structures.

The predicted structure of the M-Box riboswitch, at 83% sensitivity (Table 1), was formally the lowest quality model in the test set. Differential reactivity constraints improved the prediction by a single base pair relative to the structure predicted using 1M7 data only (SEQ ID NO:3). The overall topology of the M-Box RNA is largely correct regardless of the inclusion of differential SHAPE information: The three-helix junction and all major helices are predicted correctly. The largest difference between the modeled and accepted structures occurs at the P1 helix connecting the 5' and 3' ends of the RNA. Nucleotides in this helix are moderately reactive toward SHAPE reagents, suggesting that the P1 helix is not especially stable under the conditions used for structure probing. In the crystal structure that is the basis for the accepted model, the P1 helix is stabilized by three G-C base pairs (Dann et al. 2007) that were not present in the transcript analyzed by SHAPE. SHAPE data suggest that the native sequence P1 helix is conformationally dynamic. For the sequence of RNA probed in this work, it is inferred that the SHAPE-constrained structure is essentially correct.

Responsive and Nonresponsive RNAs.

For the RNAs in the test set, predictions either significantly improved with the addition of differential SHAPE data or were only modestly affected. Structural improvement is defined as significant if the sensitivity or ppv or both increased by at least 3%. Seven RNAs in the data set showed significant improvement by this criterion (Table 1, top, responsive RNAs). The predicted structures for these RNAs increased in sensitivity from an average 84.5% to an average of 93.4%. Improvement in positive predictive value (ppv) was even more substantial: from 78.1% to 91.2%. Of the RNAs in the less responsive category, four of the eight showed small improvements in sensitivity or ppv (Table 1, middle), and the changes in the lowest free-energy structure involved relatively minor adjustments in base-pairing relative to structures predicted using 1M7 data only. Notably, although predictions for multiple RNAs were improved by the addition of differential SHAPE restraints, none of the predictions became substantially worse with the exception of the Tetrahymena group I intron (Table 1).

The modeled structure for the Tetrahymena group I intron became less like the accepted structure upon inclusion of differential reactivity information: The sensitivity decreased from 93% to 85% (SEQ ID NO:4; Table 1). The P7 helix comprises a pseudoknot in the accepted RNA structure. One strand of the P7 helix is reactive by SHAPE and is not present in the SHAPE-directed model. These data suggest that the P7 helix is conformationally dynamic under the solution probing conditions used in this work.

Discussion

Developing accurate secondary structure models for long RNAs is a desirable prerequisite for understanding the role of RNA structure and RNA-ligand interactions in most phases of gene regulation (Mauger et al. 2013). Moreover, an accurate secondary structure model can facilitate tertiary structure modeling (Hajdin et al. 2010; Bailor et al. 2011). A desirable approach for RNA structure modeling should balance high accuracy with concise and scalable experimentation. The nearest-neighbor thermodynamic model developed by Turner and colleagues (Mathews and Turner 2006) provides a foundation for secondary structure modeling. However, there are features of RNA folding that are difficult to extract from sequence, including ligand and protein binding effects, non-canonical and long-range tertiary structure interactions, and the kinetic history of the RNA folding reaction. Inclusion of single-reagent experimental structure probing data provides a substantial improvement in modeling accuracy for many RNAs (Deigan et al. 2009; Hajdin et al. 2013), but this improvement was not enough to yield accurate secondary structure models for all RNAs in our test set (see, e.g., FIG. 1). It is demonstrated herein that inclusion of information from a differential SHAPE experiment substantially increases the sensitivity and positive predictive value of secondary structure models for an RNA test set designed to be as challenging as possible (Table 1).

The information content of three-reagent SHAPE-directed RNA structure modeling appears to exceed that of previously described chemical probing approaches. Addition of dimethyl sulfate (DMS) and CMCT reactivity information in the context of a data set of six small RNAs yielded improvement of roughly three base pairs in one RNA (Table 2; Kladwang et al. 2011b; Cordero et al. 2012). In contrast, the differential SHAPE experiment yielded large, structurally significant improvements in seven RNAs (Table 1, top) and less dramatic improvements in four other RNAs (Table 1, middle) over and above single-reagent 1M7-directed modeling. Large improvement was observed for the 5S rRNA, which was not improved with addition of DMS and CMCT data (Cordero et al. 2012). In addition, models developed using three-reagent SHAPE probing have prediction accuracies that equal or exceed that of approaches that involve probing comprehensive sets of mutants (Kladwang et al. 2011a). The differential SHAPE data thus have high information content that is obtained in a concise experiment that scales readily to large RNAs.

Using differential SHAPE for RNA secondary structure prediction represents a significant advance in RNA structure modeling. With differential SHAPE information, the structures of some of the RNA molecules that were previously viewed as the most challenging, including the 5S rRNA, the glycine riboswitch, and some ribosomal domains, were modeled in nearly perfect agreement with the accepted structures (Table 1). An intriguing trend was that the RNAs that were most responsive to the differential reactivity penalty were those with structures predicted most poorly in the absence of differential SHAPE information. RNAs in this class likely have non-canonical interactions that are incompletely described by the nearest-neighbor algorithm or single-reagent data. In several cases in which SHAPE-directed models disagree with the accepted structures—those of the MBox and lysine riboswitches and the *Tetrahymena* group I intron—"errors" appear to reflect differences between in-crystal and in-solution conformations for these RNAs.

Currently, only a small database of RNAs with well-defined accepted structures (Rivas et al. 2012; Leonard et al. 2013) is available. There are currently very few large RNAs with complex structures whose structures are well verified. Also, approaches for modeling pseudo knots have advanced significantly (Hajdin et al. 2013) but accurate modeling of more than a single pseudoknot in a complex RNA remains a challenge, both due to limitations in current energy models and due to the computational requirements for many algorithms. The present work can be used as part of efforts to address these issues.

While the present work focused on canonical base pairs and did not explicitly model noncanonical pairs, in many cases these can be inferred from their lack of reactivity toward 1M7. Also, SHAPE-directed folding algorithms currently include base-pairing partners to within 600 nt. In general, this is a good assumption and, for example, allows full-length ribosomal RNAs to be modeled at high accuracy (Deigan et al. 2009). But, there are important RNA-RNA interactions that occur over distances of 1000 nt or more (Alvarez et al. 2005; Jin et al. 2011). Finally, SHAPE reactivities reflect the structural ensemble present in solution at the time of probing. If an RNA is partially misfolded or samples multiple conformations, the resulting SHAPE profile will reflect these contributions.

The highly accurate RNA secondary structure modeling reported here involves straightforward experiments with three reagents 1M7, 1M6, and NMIA. This work examined complex RNA structures, including >3800 nt, and specifically focused on those RNAs thought to comprise the most difficult known modeling challenges. Three-reagent SHAPE structure probing is experimentally concise, yields consistently accurate RNA structural models, and can be applied to RNAs of any complexity and size, including complete viral genomes and the constituents of entire transcriptomes.

Materials and Methods

Chemical probing by differential SHAPE Differential SHAPE data for the aptamer domains of the *E. coli* thiamine pyrophosphate (TPP) riboswitch, *Vibrio vulnificus* adenine riboswitch, and *Thermotoga maritime* lysine riboswitch were reported previously (Steen et al. 2012). DNA templates (IDT) for *E. coli* 5S rRNA and the tRNA$^{Phe}$, *Fusobacterium nucleatum* glycine riboswitch, *Bacillus subtilis* M-Box riboswitch, *Tetrahymena thermophila* group I intron, and the *Oceanobacillus iheyensis* group II intron RNAs were encoded in the context of flanking 5' and 3' structure cassettes (Wilkinson et al. 2006), amplified by PCR, and transcribed into RNA using T7 RNA polymerase. RNAs were purified using denaturing polyacrylamide gel electrophoresis, excised from the gel, and passively eluted overnight at 4° C. 16S and 23S ribosomal RNAs were isolated from DH5α cells during mid-log phase using non-denaturing conditions (Deigan et al. 2009). RNAs were refolded in 100 mM HEPES, pH 8.0, 100 mM NaCl, and 10 mM MgCl2 (Steen et al. 2012). The glycine aptamer RNA was incubated with 5 µM final glycine during folding. After folding, all RNAs were modified in the presence of 8 mM SHAPE reagent and incubated for 3 min (1M6 and 1M7) or 22 min (NMIA) at 37° C. No-reagent controls, containing neat DMSO rather than SHAPE reagent, were performed in parallel.

Following modification and precipitation with ethanol, reagent and control RNAs were subjected to reverse transcription with SUPERSCRIPT III™ kit (Invitrogen) using fluorescently labeled primers (VIC dye, Invitrogen) that targeted the 3' structure cassette (Wilkinson et al. 2006). A second, internal primer was used for the group II intron to read through the end of the RNA. A reverse transcription sequencing reaction using ddC and a NED-labeled primer was also performed to allow sequence alignment. Reagent or no-reagent control reactions were combined with sequencing reactions and analyzed using an ABI 3500 capillary electrophoresis instrument. Resulting data were processed using QuShape (Karabiber et al. 2013).

The ribosomal RNAs were analyzed by a new approach, SHAPEMaP, described herein below. For all RNAs, 1M7 SHAPE reactivities were normalized using the boxplot approach (Hajdin et al. 2013). In this approach, reactivities were first sorted, and reactivities above either 1.5×interquartile range or the 90th percentile, whichever value was greater, were excluded as outliers. Next, a normalization factor was calculated by averaging the next 10% of SHAPE reactivities. The original data set was then divided by the newly calculated normalization factor to yield the final processed data.

Differential SHAPE Data Analysis.

NMIA and 1M6 SHAPE reactivities were normalized by excluding the top 2% of reactivities and dividing by the average of the next 8% of reactivities. 1M6 reactivities were then scaled more precisely to NMIA reactivities by minimizing the reactivity difference over a 51-nt sliding window. The scaled 1M6 reactivities were subtracted from NMIA reactivities to yield a differential SHAPE profile. This algorithm, implemented in a python program, is described elsewhere herein.

Differential SHAPE Pseudo-Free Energy Change Penalty.

RNAs with secondary structures derived from high-resolution methods (crystallography or NMR) were used to classify the conformation of nucleotides as either paired (G-C, A-U, or G-U) or non-paired. Next, a histogram of differential reactivities (NMIA reactivity minus 1M6 reactivity) for each category was created using a bin-width of 0.2 SHAPE units. Positive and negative differential SHAPE reactivities were treated separately. A $\Delta G_{Diff}$ statistical energy potential was then fit using an approach analogous to those used extensively for protein modeling (Rohl et al. 2004) and recently for RNA modeling (Cordero et al. 2012). Histograms of paired and nonpaired differential nucleotides from all RNAs were pooled and fit to a γ distribution. A free energy at a temperature (T) of 310 K was calculated using the Gibbs relationship:

$$\Delta G \text{Diff} = -k_b T \ln P(x) \text{paired } P(x) \text{nonpaired}.$$

P(x)paired and P(x)nonpaired are the probabilities that a nucleotide is paired or nonpaired at SHAPE reactivity x, respectively; $k_b$ is the Boltzmann constant; and $\Delta G_{Diff}$ is the resulting free change energy penalty that should be applied to a particular differential SHAPE reactivity, x. The resulting function was linear with an intercept near zero. To simplify the calculation and to make the energy function continuous for all differential reactivities, $\Delta G_{Diff}$ was fit to a linear equation with an intercept of zero. A standard error measurement of the fit was estimated by a leave-one-out jackknife approach; the resulting fit was a line with a slope of 2.11 kcal/mol and an intercept of zero.

Exploration of Simpler Differential SHAPE Energy Potentials.

We explored the possibility of omitting the 1M6 experiment and calculating differential SHAPE reactivities based only on 1M7 and NMIA experiments. Reactivity differences between NMIA and 1M7 were calculated for each nucleotide using the difference subtraction algorithm outlined above. The relationship was linear with a slope of 2.91 kcal/mol. Standard errors resulting from a leave-one out jackknife analysis were of similar magnitude to those of the relationship between NMIA and 1M6 reactivities. This two-reagent version of the differential SHAPE experiment yielded significant improvements to RNA secondary structure modeling (Table 3); however, the three-reagent analysis ultimately yielded more accurate structure models (cf. Table 1 and Table 3). Due to the higher information content of the NMIA-1M6 differential analysis, it is suggested to use three reagents (1M7, 1M6, and NMIA) to achieve desirably high accuracies in secondary structure modeling. During the course of fitting new differential SHAPE data the 1M7 free energy potential was also refit using a statistical potential and previously published RNA data set (Hajdin et al. 2013). Paired and nonpaired nucleotide distributions were fit to a mixture of two γ distributions, and a free energy change term was calculated using the Gibbs relationship. The resulting free energy change function was comparable in magnitude and x-intercept to the prior grid-search optimized log function. Thus, the original log-function for incorporating 1M7 data into SHAPE-directed structure modeling was chosen for use.

Implementation in RNAstructure Fold and ShapeKnots.

A modified SHAPE energy file was created for use in RNAstructure Fold (Reuter and Mathews 2010) and ShapeKnots (Hajdin et al. 2013) to incorporate the differential SHAPE information. Differential pseudo-free energy change values ($\Delta G_{Diff}$) for each nucleotide were calculated from the positive-amplitude differential reactivities (d):

$$\Delta G(d)_{Diff} = \begin{cases} 2.11d & \text{if } d > 0 \\ 0 & \text{if } d \leq 0 \end{cases}$$

SHAPE pseudo-free energy changes were calculated from 1M7 reactivities using the log-form SHAPE equation (Hajdin et al. 2013):

$$\Delta G_{SHAPE} = 1.8 \ln(\text{SHAPE}+1) - 0.6$$

These two free energies were summed, and a modified SHAPE reactivity file was calculated for use in Fold or ShapeKnots such that, when used with slope of 1.0 and an intercept of −1.0, the folding algorithm applies the appropriate pseudo-free energy change term:

$$\text{SHAPE} = e^{(\Delta G_{SHAPE} \Delta G_{DIFF}+1)} - 1$$

Future versions of ShapeKnots and Fold will simplify this procedure and allow the 1M7 and differential-SHAPE magnitudes to be entered directly from a data file. For ShapeKnots, the optimized pseudoknot parameters (P1=3.5, P2=6.5) (Hajdin et al. 2013) were used. The maxtracebacks option was set to 100 and the window option was set to 0 to maximize the number of potential identified structures.

The calculation for folding RNAs using 1M7 rather than 1M6 as the differential reagent was performed in the same way, except that the differential slope was 2.91. The resulting folds are summarized in Table 3. In general, the use of ShapeKnots is suggested for RNA secondary structure modeling because of its ability to predict pseudoknots (Hajdin et al. 2013); at a practical level, this program is limited to RNAs under ~700 nt in length.

Plots and Figures.

Secondary structure plots were constructed using VARNA (Darty et al. 2009), and circle plots were made using CircleCompare, a pad of RNAstructure (Reuter and Mathews 2010). Model sens was calculated as the number of correct base pairs divided by the total number of base pairs in the accepted structure; ppv was calculated as the number of correct base pairs divided by the total number of predicted base pairs. sens and ppv values for ribosomal domains were calculated after omitting regions (Deigan et al. 2009) in which SHAPE reactivities were clearly not consistent with the pattern of base-pairing in the accepted secondary structure model.

TABLE 1

RNA secondary structure modeling accuracies with 1M7 and differential SHAPE information. All well-folded RNAs containing up to one pseudoknot, of which we are aware, for which single-reagent 1M7-restrained secondary structure prediction results in less than 90% sensitivity are included in this table. RNAs are listed based on whether or not modeling is responsive to differential reactivity information: (top) predictions that improve and (bottom) predictions that show small or no changes. RNAs were judged to be responsive to differential SHAPE data if either the sens or ppv changed by at least 3%. Averages were calculated separately for each class and for all RNAs together.

| | | SHAPE | | | | | |
|---|---|---|---|---|---|---|---|
| | | − | | + differential | | + | |
| | length | | | − | | NMIA-1M6 | |
| | (nts) | sens | ppv | sens | ppv | sens | ppv |
| responsive | | | | | | | |
| TPP riboswitch, E. coli | 79 | 77.3 | 85.0 | 96.5 | 91.3 | 95.5 | 100.0 |
| cyclic-di-GMP riboswitch, V. cholerae | 97 | 75.0 | 77.8 | 89.2 | 86.2 | 96.4 | 93.1 |
| 5 S rRNA, E. coli | 120 | 28.6 | 25.0 | 85.7 | 76.9 | 94.3 | 91.7 |
| Glycine riboswitch, F. nuleatum | 158 | 70.0 | 60.9 | 55.0 | 48.9 | 95.0 | 95.0 |
| Domain III of 23 S rRNA, E. coil | 372 | 46.9 | 43.1 | 82.7 | 74.3 | 90.8 | 83.2 |

TABLE 1-continued

RNA secondary structure modeling accuracies with 1M7 and differential SHAPE information. All well-folded RNAs containing up to one pseudoknot, of which we are aware, for which single-reagent 1M7-restrained secondary structure prediction results in less than 90% sensitivity are included in this table. RNAs are listed based on whether or not modeling is responsive to differential reactivity information: (top) predictions that improve and (bottom) predictions that show small or no changes. RNAs were judged to be responsive to differential SHAPE data if either the sens or ppv changed by at least 3%. Averages were calculated separately for each class and for all RNAs together.

| | | SHAPE | | | | | |
|---|---|---|---|---|---|---|---|
| | | − | | + differential | | + | |
| | length | | | − | | NMIA-1M6 | |
| | (nts) | sens | ppv | sens | ppv | sens | ppv |
| Group I Intron, *T. thermophila* | 425 | 83.3 | 75.0 | 93.2 | 91.2 | 84.9 | 89.7 |
| 3' domain of 16 S rRNA, *E. coli* | 478 | 26.7 | 21.2 | 89.5 | 77.6 | 97.1 | 86.1 |
| Average | | 58.3 | 55.4 | 84.5 | 78.1 | 93.4 | 91.2 |
| | | non-responsive | | | | | |
| Adenine riboswitch, *V. vulnificus* | 71 | 100.0 | 100.0 | 100.0 | 100.0 | 100.0 | 100.0 |
| tRNA phe, *E. coil* | 76 | 100.0 | 91.3 | 100.0 | 75.0 | 100.0 | 77.8 |
| M-Box riboswitch, *B. subtilis* | 154 | 87.5 | 91.3 | 83.3 | 90.9 | 83.3 | 93.0 |
| Lysine riboswitch, *T. maritime* | 174 | 75.8 | 84.8 | 84.9 | 90.3 | 84.9 | 90.3 |
| Group II Intron, *O. iheyensis* | 412 | 88.0 | 97.5 | 93.2 | 96.9 | 92.5 | 98.4 |
| 5' domain of 16 S rRNA, *E. coli* | 530 | 61.3 | 57.9 | 97.8 | 91.8 | 97.8 | 91.8 |
| Domain II of 23 S rRNA, *E. coli* | 685 | 87.6 | 78.6 | 97.8 | 87.4 | 96.8 | 88.2 |
| Average | | 85.7 | 85.9 | 93.9 | 90.3 | 93.6 | 91.4 |
| Overall Average | | 72.0 | 70.7 | 89.2 | 84.2 | 93.5 | 91.3 |

TABLE 2

RNA secondary structure modeling accuracies comparing three-reagent differential SHAPE to related recent works. Approaches that allow pseudoknots are indicated with an asterisk. Methods that used parameters optimized using small datasets are indicated with a dagger.

| | | Source | | | | | | | |
|---|---|---|---|---|---|---|---|---|---|
| | | This work* | | Cordero et al. 2012 | | Cordero et al. 2012 | | Cordero et al. 2012 | Hajdin et al. 2013* |
| | | Method | | | | | | | |
| | length | Three reagent | | NMIA | | DMS | | NMIA + DMS | 1M7 |
| | (nts) | sens | ppv | sens | ppv | sens | ppv | sens | ppv | sens |
| Adenine riboswitch, *V. vulnificus* | 71 | 100.0 | 100.0 | 100.0 | 91.3 | 100.0 | 91.3 | 100.0 | 91.3 | 100.0 |
| tRNA phe, *E. coli* | 76 | 100.0 | 77.8 | 100.0 | 95.5 | 100.0 | 95.5 | 100.0 | 95.5 | 100.0 |
| TPP riboswitch, *E. coli* | 79 | 95.5 | 100.0 | — | — | — | — | — | — | 100.0 |
| cyclic-di-GMP riboswitch, *V. cholerae* | 97 | 96.4 | 93.1 | 96.2 | 92.5 | 80.7 | 91.3 | 96.2 | 92.5 | 89.3 |
| 5 S rRNA, *E. coli* | 120 | 94.3 | 91.7 | 85.5 | 76.3 | 85.3 | 76.3 | 85.3 | 76.3 | 85.3 |
| M-Box riboswitch, *B. subtilis* | 154 | 83.3 | 93.0 | — | — | — | — | — | — | 87.5 |
| Glycine riboswitch, *F. nuleatum* | 158 | 95.0 | 95.0 | 94.9 | 86.0 | 97.5 | 92.8 | 97.5 | 92.8 | — |
| Lysine riboswitch, *T. maritime* | 174 | 84.9 | 90.3 | — | — | — | — | — | — | 87.3 |
| Domain III of 23 S rRNA, *E. coli* | 372 | 90.8 | 83.2 | — | — | — | — | — | — | — |
| Group II Intron, *O. iheyensis* | 412 | 92.5 | 98.4 | — | — | — | — | — | — | 93.2 |
| Group I Intron, *T. thermophila* | 425 | 84.9 | 89.7 | — | — | — | — | — | — | 93.9 |
| 3' domain of 16 S rRNA, *E. coli* | 478 | 97.1 | 86.1 | — | — | — | — | — | — | — |
| 5' domain of 16 S rRNA, *E. coli* | 530 | 97.8 | 91.8 | — | — | — | — | — | — | — |
| Domain II of 23 S rRNA, *E. coli* | 685 | 96.8 | 88.2 | — | — | — | — | — | — | — |

TABLE 3

RNA secondary structure modeling accuracies for a two-reagent differential SHAPE experiment using 1M7 and NMIA.
RNAs are listed based on whether or not structure prediction was sensitive to the NMIA-1M7 differential reactivities.
The two-reagent experiment yielded significant modeling improvements relative to prediction with 1M7 data only, but
improvements were not as large as those with the recommended three-reagent experiment (Table 1).

| | | SHAPE | | | | | |
|---|---|---|---|---|---|---|---|
| | | − | | + differential | | + | |
| | length | − | | − | | NMIA-1M7 | |
| | (nts) | sens | ppv | sens | ppv | sens | ppv |
| responsive | | | | | | | |
| TPP riboswitch, *E. coli* | 79 | 77.3 | 85.0 | 96.5 | 91.3 | 95.5 | 100.0 |
| 5 S rRNA, *E. coli* | 120 | 28.6 | 25.0 | 85.7 | 76.9 | 94.3 | 91.7 |
| Glycine riboswitch, *F. nuleatum* | 158 | 70.0 | 60.9 | 55.0 | 48.9 | 97.5 | 95.1 |
| Group I Intron, *T. thermophila* | 425 | 83.3 | 75.0 | 93.2 | 91.2 | 82.6 | 68.7 |
| 3' domain of 16 S rRNA, *E. coil* | 478 | 26.7 | 21.2 | 89.5 | 77.6 | 97.1 | 86.8 |
| 5' domain of 16 S rRNA, *E. coli* | 530 | 61.3 | 57.9 | 97.8 | 91.8 | 88.3 | 83.4 |
| Average | | 57.9 | 54.2 | 86.3 | 79.6 | 92.5 | 91.0 |
| non-responsive | | | | | | | |
| Adenine riboswitch, *V. vulnificus* | 71 | 100.0 | 100.0 | 100.0 | 100.0 | 100.0 | 100.0 |
| tRNA phe, *E. coli* | 76 | 100.0 | 91.3 | 100.0 | 75.0 | 100.0 | 77.8 |
| cyclic-di-GMP riboswitch, *V. cholerae* | 97 | 75.0 | 77.8 | 89.2 | 86.2 | 89.2 | 86.2 |
| M-Box riboswitch, *B. subtilis* | 154 | 87.5 | 91.3 | 83.3 | 90.9 | 83.3 | 93.0 |
| Lysine riboswitch, *T. maritime* | 174 | 75.8 | 84.8 | 84.9 | 90.3 | 84.9 | 90.3 |
| Domain III of 23 S rRNA, *E. coil* | 372 | 46.9 | 43.1 | 82.7 | 74.3 | 82.7 | 74.3 |
| Group II Intron, *O. iheyensis* | 412 | 88.0 | 97.5 | 93.2 | 96.9 | 94.0 | 98.4 |
| Domain II of 23 S rRNA, *E. coli* | 685 | 87.6 | 78.6 | 97.8 | 87.4 | 97.8 | 87.9 |
| Average | | 82.6 | 83.0 | 91.4 | 87.6 | 91.5 | 88.5 |
| Overall Average | | 72.0 | 70.7 | 89.2 | 84.2 | 91.9 | 89.5 |

Example 4

Single-Molecule Correlated Chemical Probing of RNA

RNA molecules function as the central conduit of information transfer in biology. To do this, they encode information both in their sequences and in their higher-order structures. Understanding the higher-order structure of RNA remains challenging. In this Example provided is a simple, experimentally concise, and accurate approach for examining higher-order RNA structure by converting widely used massively parallel sequencing into an easily implemented single-molecule experiment for detecting through-space interactions and multiple conformations. This approach is then employed to analyze higher-order RNA structure, detect biologically important hidden states, and refine accurate three-dimensional structure models.

RNA functions are mediated by tiered levels of information: The simplest is the primary sequence, and the most complex is the higher-order structure that governs interactions with ligands, proteins, and other RNAs (Sharp P A (2009). *Cell* 136:577-5802; Leontis N B, et al. (2006) *Curr Opin Struct Biol* 16:279-287). Many RNAs can form more than one stable structure, and these distinct conformations often have different biological activities (Montange R K, Batey R T (2008) Riboswitches: emerging themes in RNA structure and function. *Annu Rev Biophys* 37:117-133; Dethoff E A, Chugh J, Mustoe A M, Al-Hashimi H M (2012) Functional complexity and regulation through RNA dynamics. *Nature* 482:322-330). Currently, the rate of describing new RNA sequences vastly exceeds abilities to examine their structures.

Figures 2A, 2B:
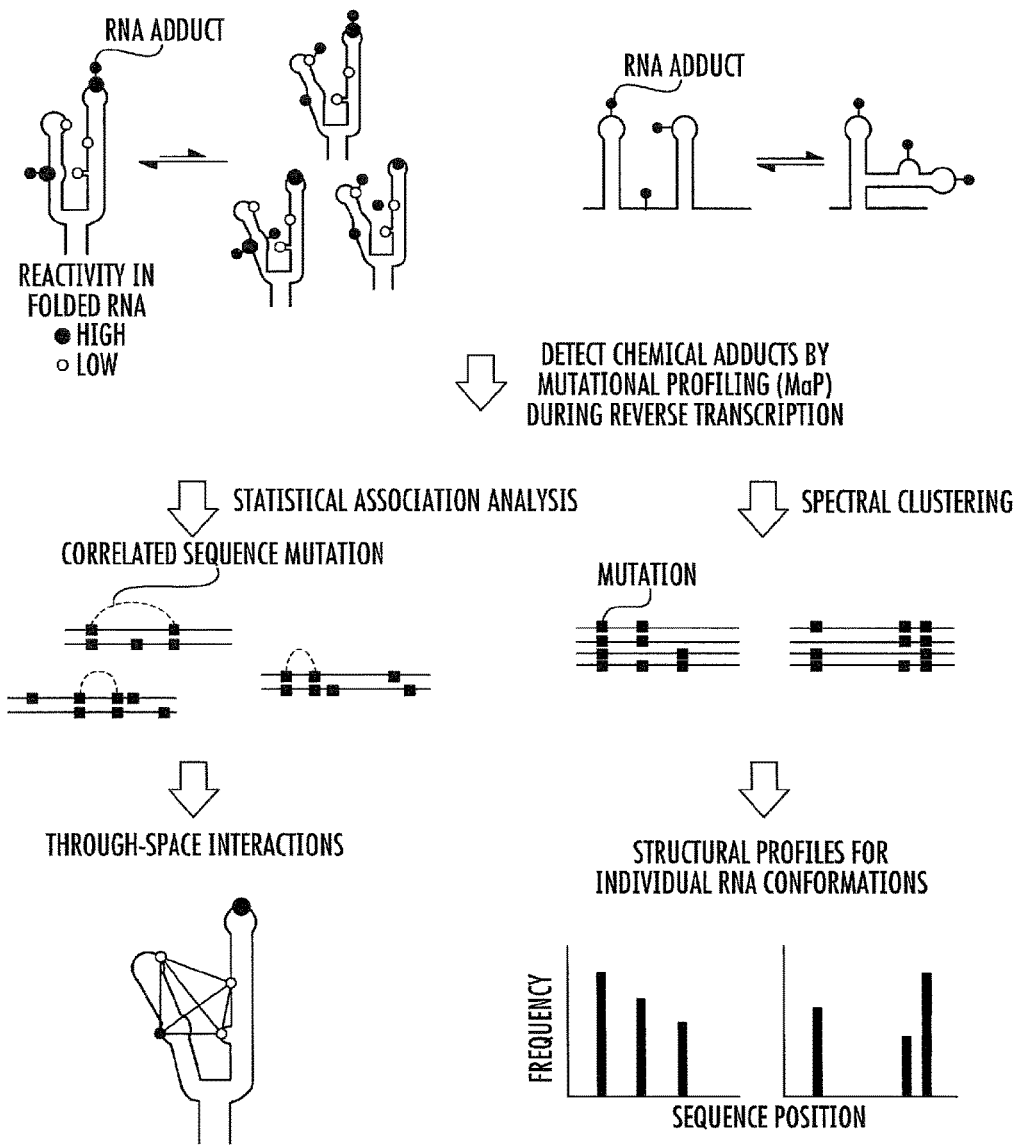
FIGS. 2A and 2B. Single-molecule RNA structure analysis by massively parallel sequencing.

Disclosed in this Example is the characterization of through-space interactions and multiple conformations in single RNAs by melding chemical probing and massively parallel sequencing. Because massively parallel sequencing reports the sequences of single templates, each read is fundamentally a single-molecule observation (Shendure J, Ji H (2008) Next-generation DNA sequencing. *Nat Biotechnol* 26:1135-1145). We first modified RNA with a reagent that is sensitive to the underlying RNA structure and then detected multiple adducts in individual RNA strands (FIGS. 2A and 2B). Chemical adducts were detected as sequence mutations based on their ability to induce efficient misreading of the template nucleotide by a reverse transcriptase enzyme, an approach called mutational profiling, or MaP (described elsewhere herein). Single molecule probing data were used in two distinct ways: to detect correlated RNA modifications reflecting higher-order through-space interactions (FIG. 2A) and to examine multiple conformations in single in-solution ensembles (FIG. 2B).

Results and Discussion

Multisite Dimethyl Sulfate Reactivity with RNA.

We used dimethyl sulfate (DMS) to probe the structures of three RNAs: the *Escherichia coli* thiamine pyrophosphate (TPP) riboswitch (79 nt) (Serganov A, et al. (2006). *Nature* 441:1167-1171), the *Tetrahymena* group I intron P546 domain (160 nt) (Cate J H et al. (1996). *Science* 273:1678-1685), and the *Bacillus stearothermophilus* RNase P catalytic domain (265 nt) (Kazantsev A V, et al. (2009). *RNA* 15:266-276). RNAs were selected to illustrate distinct RNA folding features and to emphasize increasingly difficult analysis challenges.

The TPP riboswitch binds the TPP ligand to function in gene regulation. The P546 domain has a U-shaped structure stabilized by a long-range tertiary interaction spanning roughly 45 base pairs. The RNase P domain is among the largest RNAs for which automated modeling has been pursued. DMS forms adducts at the N1 position of adenosine and N3 position of cytosine. We optimized conditions to yield multiple modifications in an RNA strand without disrupting native RNA folding. RNA samples were treated with 170 mM DMS in 10 mM Mg2+ and 300 mM cacodylate buffer at pH 7 for 6 min. The reactions were quenched by addition of excess 2-mercaptoethanol. Cytosine and adenosine nucleotides were methylated with equal efficiencies, and ~12% of nucleotides were modified under these conditions.

We detected sites of DMS methylation directly as adduct induced mutations in the full-length cDNAs generated during reverse transcription (FIGS. 2A and 2B). We visualized the overall reactivity patterns for each RNA in 2D mutation frequency profiles (FIG. 3B). Comparison with the high-resolution structures for these RNAs (Serganov A, et al., (2006) Nature 441(7097):1167-1171; Cate J H, et al., (1996) Science 273(5282):1678-1685; Kazantsev A V, Krivenko A A, Pace N R (2009) RNA 15(2):266-276) showed that nucleotides modified at high levels were those not involved in base pairing or tertiary interactions (FIG. 3C). As expected, nucleotide modification was dependent on reagent concentration, reaction time, and the stability of the RNA structure. The observed high mutation frequencies over background allowed DMS-induced mutations to be analyzed without the requirement for background correction (FIG. 3B).

Figure 3A:
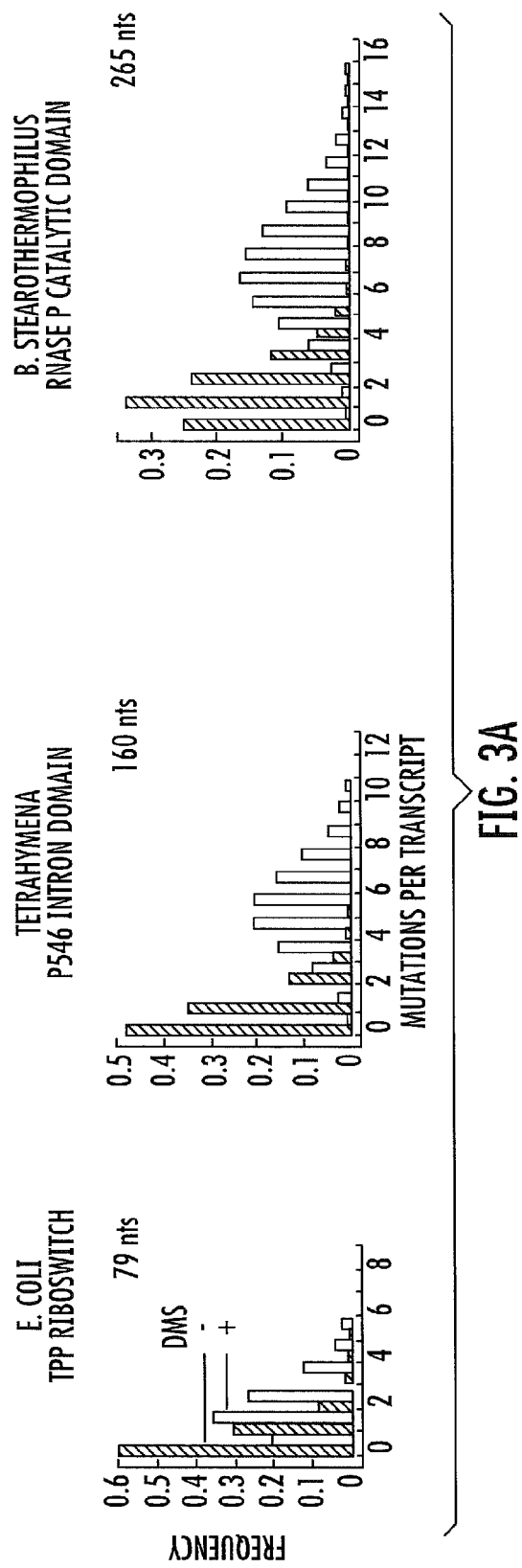
FIGS. 3A-3C. RING analysis of RNA structure. (A) Number of mutations per transcript detected by reverse transcription with (gray) and without (black) DMS modification. (B) DMS modification-induced mutation frequencies as a function of nucleotide position. Data from DMS-treated samples are shown in gray and no-reagent controls are black. (C) RINGs for the TPP riboswitch, P546 domain, and RNase P RNAs (SEQ ID NOs:5-7) showing strong and moderate correlations. Correlations occur between positions that are reactive in the native structure (filled circles) or become reactive during 'breathing' motions (open circles), reflecting the structural breathing component of reactivity interdependencies. Correlation coefficients of 0.025 and 0.035 correspond to median 2.5- and 2.8-fold increases, respectively, in the probability of mutation at one nucleotide due to mutation of a second nucleotide. Secondary structures are drawn to approximate relative helical orientations in three-dimensional space, based on known structures.
Figures 1, 3B:
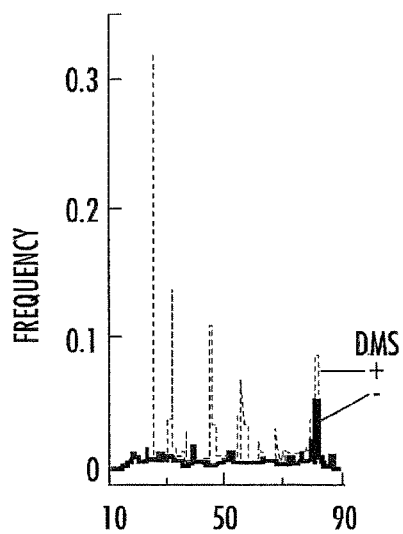
Figures 2, 3B:
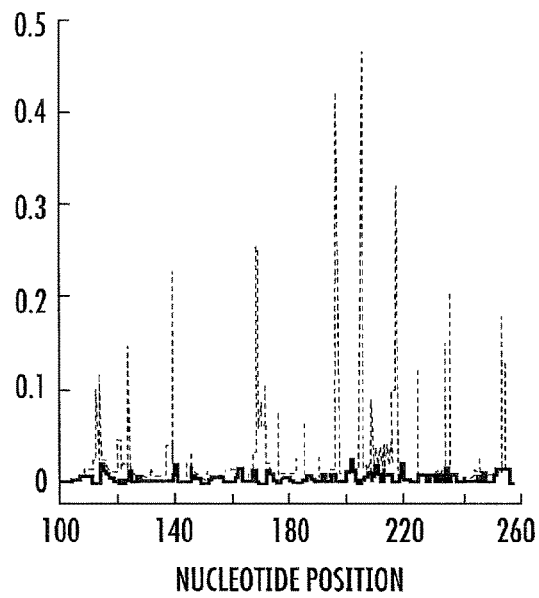
Figures 3, 3B:
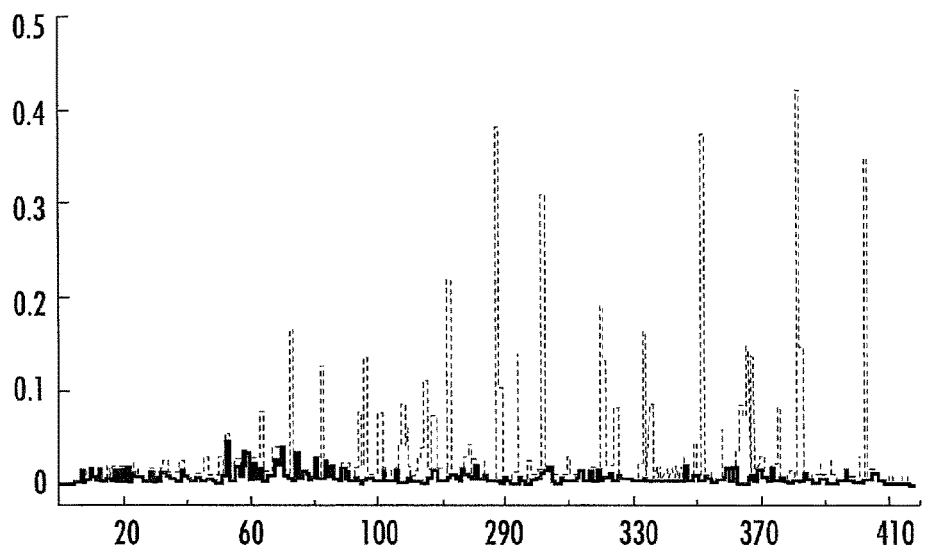
Figures 1, 3C:
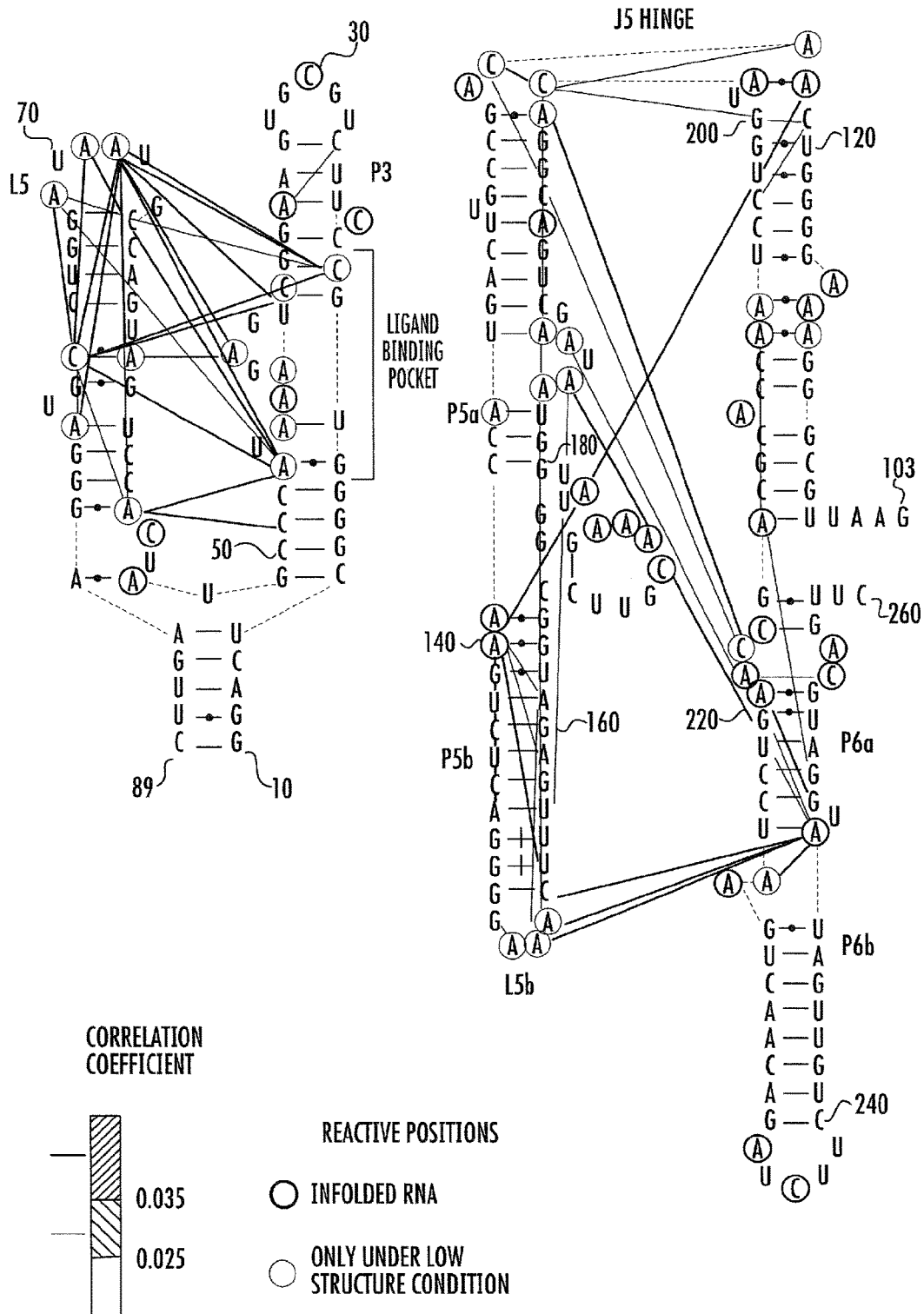
Figures 2, 3C:
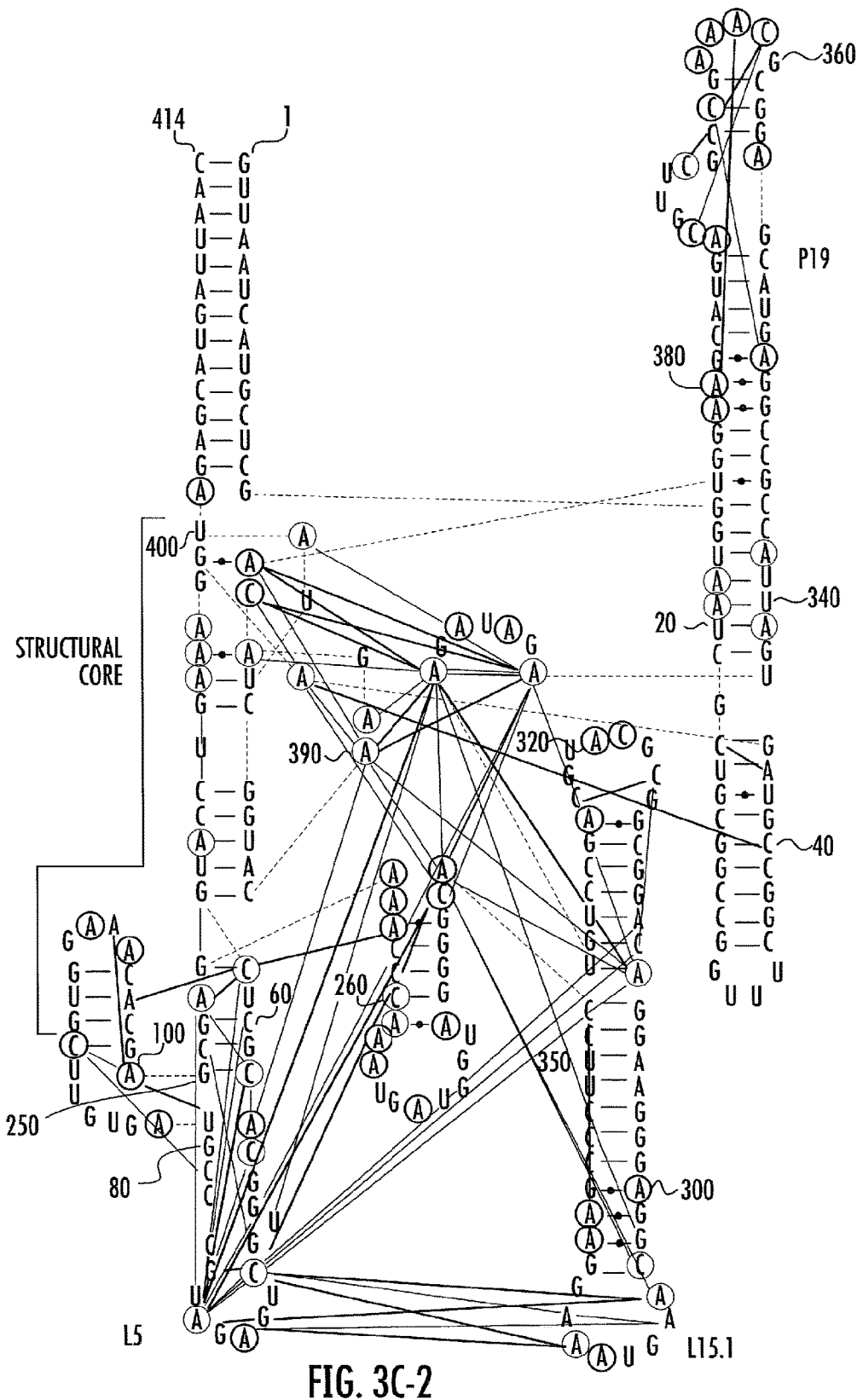

For the TPP ribo switch, the P546 domain, and the RNase P domain, averages of two, five, and seven adducts were detected in each sequencing read, respectively (FIG. 3A). Approximately 15% of the single-stranded A and C nucleotides in each RNA were modified by DMS, comparable to the level of modification of free nucleotides under these conditions. Because multiple chemical modification events were detected in sequencing reads of single RNA strands, we could quantify correlated interdependencies in reactivity. Nucleotides modified in a correlated fashion comprise RNA interaction groups, or RINGs. The correlated reactivities were measured by mutational profiling (MaP) (described elsewhere herein), yielding a RING-MaP experiment.

Through-Space RNA Interactions Detected by Statistical Association Analysis.

Nucleotides involved in through-space interactions will show correlated chemical reactivities, reflective of a "breathing" mechanism in which an RNA nucleotide becomes transiently accessible for modification. This breathing mechanism suggests that correlated probing will be selective for transient, dynamic interactions rather than static structural differences (FIG. 2A).

We used a two-part strategy to identify reactive nucleotide pairs with statistically significant correlations and to quantify the strengths of these correlations. The interdependencies for DMS reactivities for any two positions in a single RNA strand were first evaluated using a $\chi2$ test. The strength of the interaction between each pair of correlated nucleotides was then quantified using Pearson's phi metric.

RINGs for the TPP riboswitch, P546 intron domain, and RNase P RNAs (FIG. 3C) include nucleotides known to interact based on high-resolution structures (Serganov A, et al., (2006) Nature 441(7097): 1167-1171; Cate J H, et al., (1996) Science 273(5282):1678-1685; Kazantsev A V, Krivenko A A, Pace N R (2009) RNA 15(2):266-276). For example, correlated positions in the TPP riboswitch correspond to nucleotides involved in a docking interaction between the L5 loop and P3 helix and in formation of the ligand-binding pocket. In the P546 domain, correlated modifications were observed at nucleotides in the L5b loop and P6a helix docking interaction, within the J5 hinge region, and throughout the lengths of the P5a and P5b helices. In the RNase P RNA, RINGs report tertiary interactions between the L5 and L15.1 loops and in the structural core. We also observed a second set of interactions in the RNase P P19 element.

RINGs Report Higher-Order and Tertiary RNA Interactions.

We evaluated differences in the tertiary interactions, as reported by RINGs, under different solution conditions or in mutant RNAs. In the presence of $Mg^{2+}$, the P546 domain forms a U-shaped structure in which a tetraloop-receptor interaction forms between L5b and P6a and the J5 region acts as a hinge (Murphy F L, Cech T R (1994) J Mol Biol 236(1):49-63; Szewczak A A, Cech T R (1997) RNA 3(8): 838-849). These interactions were correctly reported by multiple correlated chemical modifications in these structural elements. Disruption of this tertiary structure by folding the RNA in the absence of $Mg^{2+}$ eliminated the majority of observed interactions. The tertiary structure of the P546 domain can also be perturbed by mutations in the P6a helix and in the J5 hinge. Mutation of the C223-G250 base pair in the P6a helix to A-U disrupts the L5-P6a interaction (Murphy F L, Cech T R (1994) J Mol Biol 236(1):49-63). RING analysis of this mutant showed that the correlation between L5 and P6b was lost and that other parts of the RNA also underwent significant reconfiguration. Interactions involving the hinge seemed to be strengthened and more and stronger correlations were observed within the helical domains of P5a and P5b.

Mutations that result in base pairing of nucleotides in the J5 hinge likely yield a linear conformation for the P546 domain (Szewczak A A, Cech T R (1997) RNA 3(8):838-849.). RING analysis of the J5 mutant showed the expected loss in correlated nucleotides within the J5 region and consequently the loss of the L5b-P6a interaction. The correlations among nucleotides in the P5b helix were strengthened in this mutant relative to those in observed in the wild-type RNA, but no changes were observed in correlations among nucleotides in the P5a helix. This analysis of P546 domain demonstrated that RINGs accurately reflect structural interactions in a large RNA molecule at nucleotide resolution.

Detection of Multiple and Hidden RNA Conformations.

In the RINGMaP approach, each RNA strand is sequenced independently by massively parallel sequencing. RNA strands of different conformations will tend to exhibit distinct groups of coreactive nucleotides (FIG. 2B). Such groups can be detected by spectral clustering and will be reflective of distinct, relatively stable individual structures in solution. Spectral clustering produces an objective estimate of the number of clusters and therefore the number of conformations adopted by a particular RNA in solution.

Figure 4D:
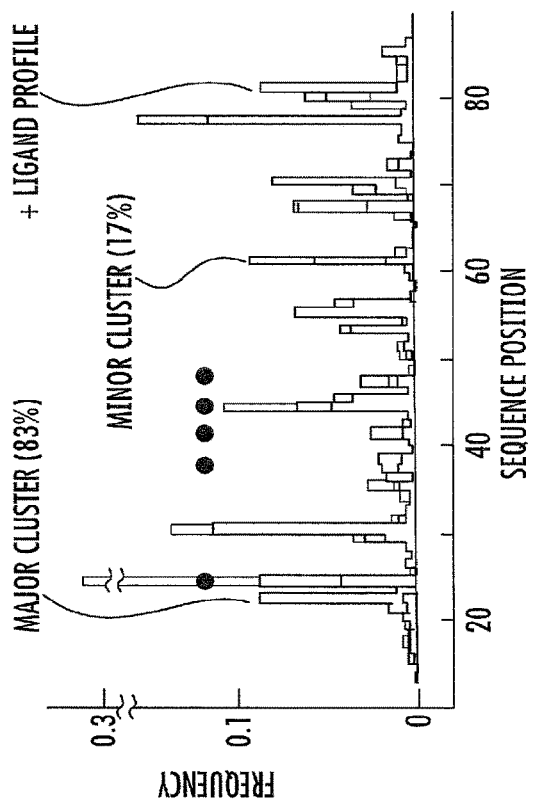
Figure 4C:
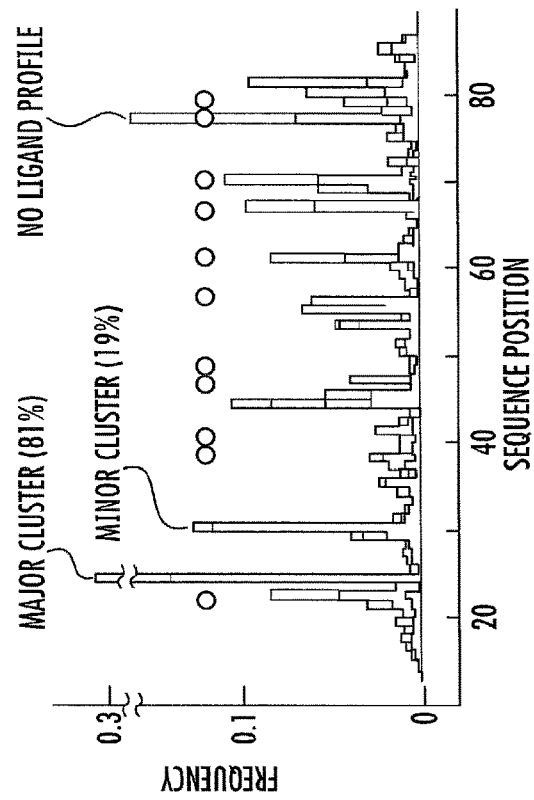
Figure 5A:
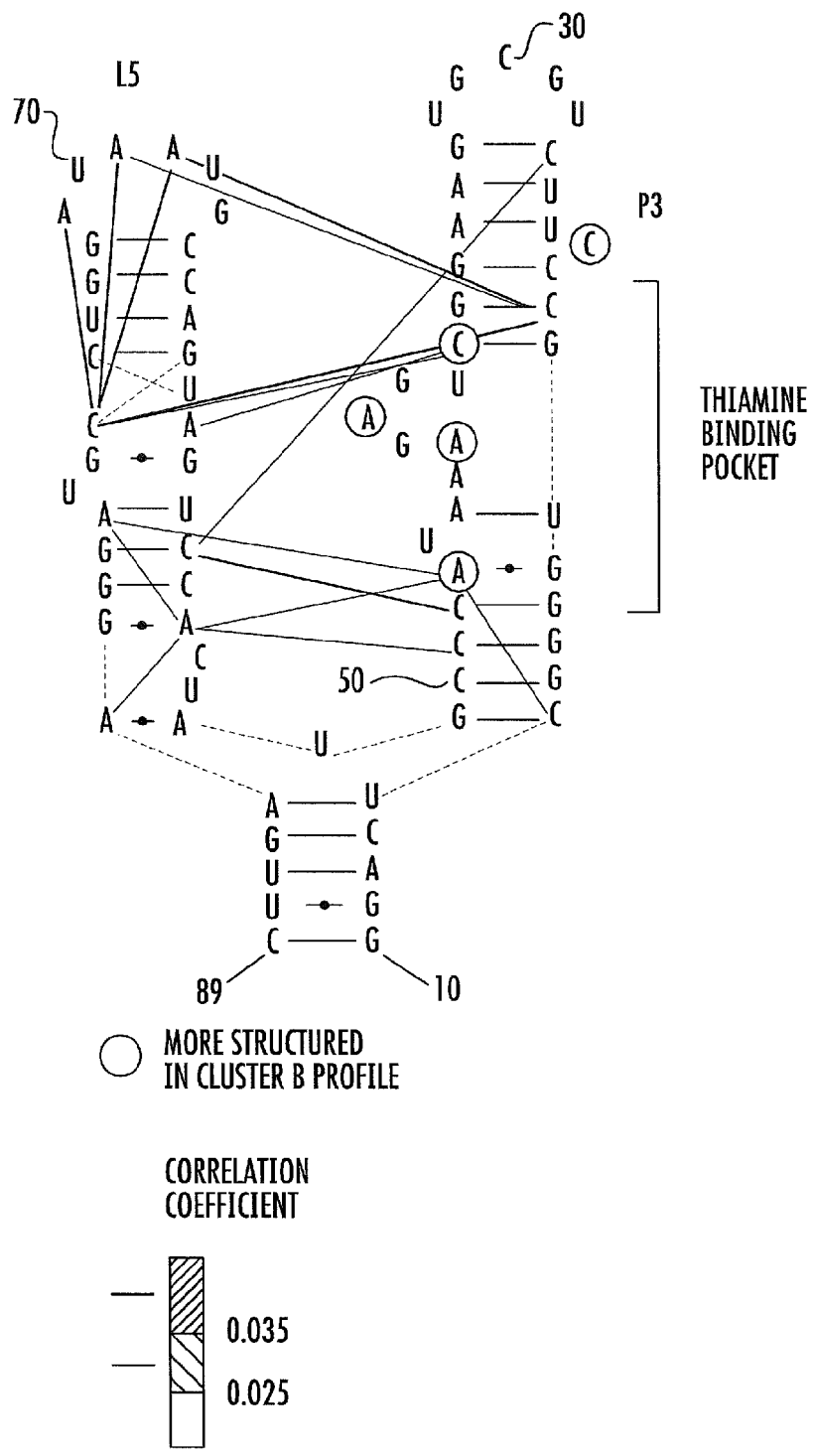
FIGS. 5A and 5B. Spectral clustering analysis of the TPP riboswitch (SEQ ID NO:5) at the sub-saturating ligand concentration of 200 nM ligand. (A) RING analysis of internucleotide association interactions. Interactions are fewer in number and weaker than those for the RNA under saturating ligand conditions (compare with FIG. 4A). (B) Three clusters were identified with population fractions of 32, 31, and 37%. Each of these clusters corresponds to a state identified in either saturating ligand concentration or in the absence of ligand with nucleotides corresponding to the ligand bound or no ligand structures.
Figure 5B:
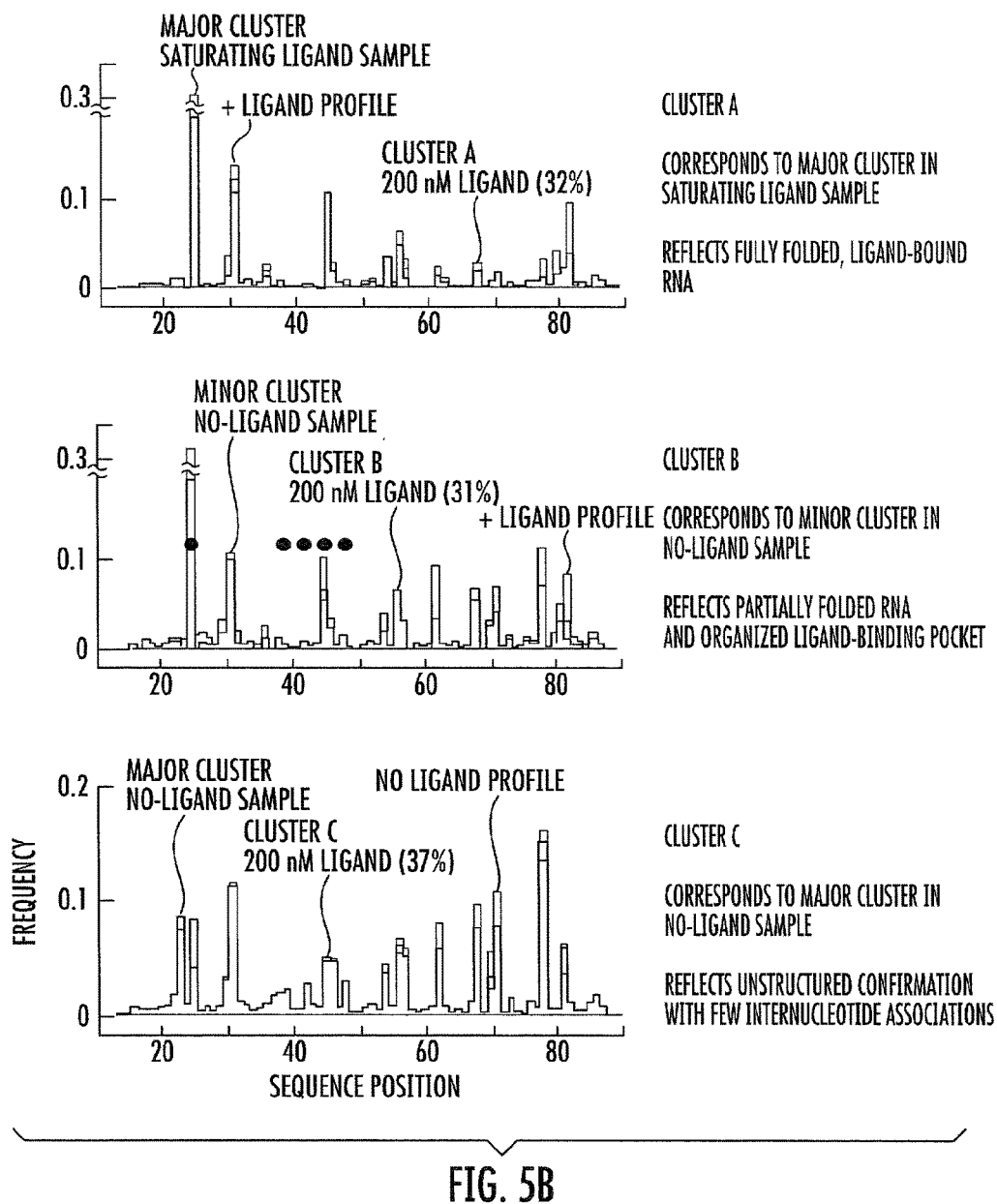

Spectral clustering analysis of the modification data obtained on the TPP riboswitch and RNase P RNAs indicated that each RNA formed multiple distinct conformations under the conditions used in our probing experiments. RINGs identified for the TPP riboswitch with saturating ligand revealed interactions in the L5-P3 docked structure and in the ligand-binding pocket (FIG. 4A). There were significantly fewer internucleotide tertiary interactions in the absence of TPP ligand than in its presence; however, specific interactions in J2-4 were still observed (FIG. 4B). Spectral clustering revealed that both the saturating-ligand and no-ligand RNAs are composite states with constituent major and minor conformations (FIGS. 4C and 4D). The minor cluster in the saturating-ligand RNA is characterized by increased DMS reactivities at precisely the positions that became reactive when no ligand was bound (FIGS. 4A and 4C, open circles). Therefore, even under saturating-ligand conditions, the TPP riboswitch RNA samples conformations characteristic of both ligand-bound and unbound states. In the absence of ligand, the major cluster has a DMS reactivity pattern similar to the less structured state in the presence of ligand. In contrast, the minor cluster detected in the absence of ligand has reduced DMS reactivities precisely in the thiamine-binding pocket, suggestive of a conformation that is more highly structured than that of the major cluster (FIGS. 4B and 4D). We infer that, in the absence of ligand, the riboswitch thiamine-binding pocket samples a "hidden" prefolded structure similar to that formed upon ligand binding. We then probed the TPP riboswitch RNA in the presence of subsaturating ligand concentrations [200 nM TTP; Kd~50-200 nM (Kulshina N, Edwards T E, Ferré-D'Amaré A R (2010) RNA 16(1):186-196)]. Clustering analysis of the chemical reactivity data produced three well-defined clusters in the ratio of 1:1:1.2 corresponding to (i) the fully folded, ligand-bound state, (ii) the state in which the ligand-binding pocket is structured but the rest of the RNA shows weak internucleotide interactions, and (iii) the relatively unstructured state with only a few interacting nucleotides (FIGS. 5A and 5B). Each of these clusters corresponds to states identified previously in either the saturating ligand or no-ligand RNAs. Spectral clustering analysis thus identified multiple distinct conformations from a single in-solution RNA ensemble, including a previously uncharacterized state in which the ligand-binding pocket is prefolded. This partially folded state is likely important for recognition of the TPP ligand. Finally, we examined the structure of the RNase P RNA as a function of $Mg^{2+}$. The networks of interactions were strikingly different in the presence and absence of $Mg^{2+}$. The strong networks of interactions between L5 and L15.1 and in the structural core disappeared in the absence of $Mg^{2+}$ and were replaced by interactions between P5.1 and P2 and within P7. Spectral clustering identified two clusters in the plus-$Mg^{2+}$ state. The minor cluster in the plus-$Mg^{2+}$ sample is distinct from both the fully folded RNA and from the no-$Mg^{2+}$ structure. Reactive nucleotides in the minor cluster comprise the L5-L15.1 and structural core interactions, indicating that these interactions are weakened in this state. Critically, single-molecule spectral clustering analysis shows that the TPP riboswitch and RNase P RNAs natively adopt multiple unique states, even under conditions generally assumed to promote formation of a single structure.

Principles of RNA Folding.

RNA structure formation can be usefully approximated by assuming that stable helices, formed locally and stabilized by Watson-Crick pairing, are subsequently organized into a 3D structure by longer-range tertiary interactions. RING analysis of the three RNAs studied here is consistent with this well-established structural hierarchy. For example, we observed RINGs that reflect noncanonical base pairs and loop-helix and loop-loop tertiary interactions that have been widely noted in prior structural studies (Butcher S E, Pyle A M (2011) Acc Chem Res 44(12):1302-1311; Brion P, Westhof E (1997) Annu Rev Biophys Biomol Struct 26:113-137.).

RING analysis also identified interactions whose prevalence was previously not fully appreciated. Approximately one-third of all correlated interactions involve single-stranded or loop nucleotides at the opposite ends of individual helices. These through-helix interactions mean that structural communication in RNA can extend over long distances. In some cases, through-helix structural coupling extends through multiple stacked helices. In addition, RING analysis indicates that tertiary interactions are not independent but instead are strongly dependent on other structural elements. We observed coupled interactions between well-defined individual tertiary structure motifs in both the TPP riboswitch and the P546 domain RNA. Disruption of any one tertiary interaction, by exclusion of ligand or by mutation, resulted in loss of the tertiary motif itself and also disrupted other interactions. RING data also support the importance of close helical packing. These interactions are especially obvious in the TPP riboswitch and in the structural core of the RNase P RNA.

Analyses of the TPP riboswitch, the P546 domain, and the RNase P domain indicate that mutations or absence of ligand (FIGS. 4 and 5) or divalent ions do not simply "subtract" an interaction from the structure but cause large-scale reorganization of RNA folding. None of the unfolded or less-folded states characterized was simply a less-structured version of a fully folded state. Instead, we find that less-structured states are stabilized by unique sets of interdependent interactions that, in general, have not been detected in prior ensemble or single-molecule studies.

Three-Dimensional RNA Structure Refinement.

Because RING analysis identifies dense arrays of nucleotide interdependencies reflective of RNA tertiary structure, we explored whether these interactions could be used as restraints to model 3D RNA folds. A small number of constraints, reflective of through-space RNA structure, are often sufficient to yield high-quality structure models (Gherghe C M, et al., (2009) J Am Chem Soc 131(7):2541-2546; Lavender C A, et al., (2010) Biochemistry 49(24):4931-4933.). We used a two-step interaction potential to introduce free-energy bonuses when constituent nucleotides come into proximity during discrete molecular dynamics simulation (Gherghe C M, et al., (2009) J Am Chem Soc 131(7):2541-2546; Lavender C A, et a., (2010) Biochemistry 49(24): 4931-4933; Ding F, et al. (2008) RNA 14(6):1164-1173). Introduction of RING constraints caused each RNA to preferentially sample collapsed states during the simulation. Following filtering by radius of gyration, representative structures were selected by hierarchical clustering. For each RNA characterized, we obtained high-quality and statistically significant (Hajdin C E, et al., (2010) RNA 16(7):1340-1349) models that correctly recapitulated the RNA architecture defined by high-resolution structures (Serganov A, et al., (2006) Nature 441(7097):1167-1171; Cate J H, et al. (1996) Science 273(5282):1678-1685; Kazantsev A V, Krivenko A A, Pace N R (2009) RNA 15(2):266-276). For the RNase P RNA, we observed overlapping RINGs spanning two/thirds of the molecule and a second non-overlapping set in P19 (FIG. 3C); this suggests that the P3-P2-P19 element is not structurally linked to the rest of the RNA architecture. The accuracy of the 3D model for the RNase P RNA is especially high in the structural core (excluding the P3-P2-P19 element) with a 14.4 Å rmsd (P<10-6) compared with the crystal structure. For the three RNAs studied here, the relative statistical significance of structure modeling actually increased with size, likely because a greater number of chemical modifications, and thus more nucleotide interactions, are detected with larger RNAs (FIG. 3A). RING-network interactions thus make possible both de novo identification of structural elements and modeling of folded domains for large RNAs.

Perspective.

Single-molecule structure analysis by correlated chemical probing, as detected by sequencing, represents a remarkably simple and generic approach for analysis of the global architectures of functionally important RNAs or DNAs. The fundamental insight that a single-molecule experiment can be created by simply recording multiple events in the same RNA or DNA strand is completely general and should inspire development of numerous new classes of experiments and biological discoveries. RING-MaP is unique in its simplicity and experimental concision and can be applied to virtually any biological RNA, without the requirement to introduce mutations, optimize for biophysical analysis, or introduce artificial structural probes. The single-molecule mutational profiling (MaP) approach described here using DMS can be readily extended to other RNA modification agents, to experiments that interrogate all four nucleotides simultaneously, to RNA-protein cross-linking, and to analysis of complex libraries of mutants. Single-molecule MaP experiments that explore protein-RNA, RNA-RNA, and DNA-mediated interactions simultaneously are clearly feasible.

Higher-order structure is tightly linked to biological function. Thus, analogous to de novo discovery based on secondary structure characterization (Example 5 herein), identifying clusters of through space RINGs in large RNAs and transcriptomes will enable widespread biological functional motif discovery.

Methods

Detailed descriptions of the RING-MaP approach, statistical association analysis, spectral clustering, and structure modeling are provided herein. Processed data and software are freely available at the corresponding author's website (chem.unc.edu/rna). Sequencing data are available at the National Center for Biotechnology Information Sequence Read Archive.

SI Methods Characterization of Reaction Between Dimethyl Sulfate and RNA Nucleobases.

Adduct formation between dimethyl sulfate (DMS) (Sigma-Aldrich) and [γ-32P]-labeled ATP, CTP, and UTP was performed by adding 10% (vol/vol) DMS (1 µL; 1.7 M in absolute ethanol) to [γ-32P]NTP in 1× reaction buffer [9 µL, 10 mM MgCl2 and 300 mM sodium cacodylate (pH 7.0)] at 37° C. Reactions were quenched with an equal volume of neat 2-mercaptoethanol (2ME) after 10, 30, 60, 120, 180, 360, and 900 s. For prequench control reactions, 1.3 M DMS solution [1:2:5 (vol/vol) DMS:ethanol:H2O] was first added to equal volume neat 2-mercaptoethanol. This mixture (2.8 µL, 625 mM DMS) was then immediately added to [γ-32P]NTP in 7.2 µL of 1.4× reaction buffer [7.2 µL; 14 mM MgCl2 and 417 mM sodium cacodylate (pH 7.0)], and the reaction was incubated at 37° C. for 15 min. Quenched reactions were resolved by gel electrophoresis (30% polyacrylamide; 29:1 acrylamide:bisacrylamide; 0.4-mm×28.5-cm×23-cm gel; 30 W, 45 min) and quantified by phosphorimaging. Data were consistent with a mechanism in which DMS forms adducts at the N1 position of adenosine and N3 position of cytosine and does not react with uridine. The change in pH during DMS adduct formation was followed in reactions without NTP at 37° C. using an Accument 25 pH meter. Direct measurements of DMS adduct formation with cytosine and adenosine suggest roughly equal reactivities with these two nucleotides. This observation differs from the widespread view that adenosine reacts more rapidly than does cytosine with DMS. We attribute this misconception to the relatively inefficient ability of N3-methyl cytosine to inhibit reverse transcriptase enzymes.

RNA Constructs.

DNA templates for the *Escherichia coli* thiamine pyrophosphate (TPP) riboswitch, *Tetrahymena* group I intron P546 domain, and *Bacillus stearothermophilus* RNase P catalytic domain RNAs, each imbedded within 5' and 3' structure cassette flanking sequences, were generated by PCR (Wilkinson, K A, et al., (2006) Nat Protoc 1(3):1610-1616). RNAs were transcribed in vitro [1 mL; 40 mM Tris (pH 8.0), 10 mM MgCl2, 10 mM DTT, 2 mM spermidine, 0.01% (vol/vol) Triton X-100, 4% (wt/vol) poly (ethylene) glycol 8000, 2 mM each NTP, 50 µL PCR-generated template, 0.1 mg/mL T7 RNA polymerase; 37° C.; 4 h] and purified by denaturing polyacrylamide gel electrophoresis (8% polyacrylamide, 7 M urea, 29:1 acrylamide:bisacrylamide, 0.4-mm×28.5-cm×23-cm gel; 32 W, 1.5 h). RNAs were excised from the gel, recovered by passive elution overnight at 4° C., and precipitated with ethanol. The purified RNAs were resuspended in 50 µL 10 mM Tris (pH 7.5), 1 mM EDTA (TE) and stored at −20° C.

RNA Folding and DMS Modification.

RNA structure probing experiments were performed in 10 mM MgCl2 and 300 mM cacodylate at pH 7.0. RNAs [5 pmol in 5 µL 5 mM Tris (pH 7.5), 0.5 mM EDTA (½×TE)] were denatured at 95° C. for 2 min, cooled on ice, treated with 4 µL 2.5× folding buffer [750 mM cacodylate (pH 7.0) and 25 mM MgCl2], and incubated at 37° C. for 30 min. After folding, the P546 domain and the RNase P catalytic domain RNAs were treated with DMS (1 µL; 1.7 M in absolute ethanol) and allowed to react at 37° C. for 6 min. No-reagent control reactions were performed with 1 µL absolute ethanol. Reactions were quenched by the addition of an equal volume of neat 2ME and immediately placed on ice. No-Mg2+ experiments were performed identically except that the 2.5× folding buffer omitted Mg2+. The TPP riboswitch RNA was incubated in folding buffer at 37° C. for 10 min, after which the TPP ligand was added at the desired concentration and samples were incubated at 37° C. for 20 min. (Note: DMS is a known carcinogen and neat 2ME has a very strong odor. Manipulations involving DMS and 2ME should be performed in a chemical fume hood. Solutions containing DMS should be neutralized with 5 N NaOH. Solutions containing DMS or 2ME should be disposed of as chemical waste.)

Reverse Transcription and Adduct Detection.

The reverse transcription and adduct detection strategy was adapted from the SHAPE mutational profiling (MaP) approach (Example 5 herein). After treatment with DMS, RNAs were purified using G-50 spin columns (GE Healthcare). Reverse transcription reactions were performed using SuperScript II reverse transcriptase (Invitrogen) for 3 h at 42° C. [0.5 mM premixed dNTPs, 50 mM Tris HCl (pH 8.0), 75 mM KCl, 6 mM MnCl2, and 10 mM DTT]. Reactions were desalted with G-50 spin columns (GE Healthcare). Under these conditions (long incubation time, in the presence of Mn2+), the reverse transcriptase reads through methyl adducts at the N1 and N3 positions of adenosine and cytosine, respectively, yielding a mutation at the site of the adduct. Double-stranded DNA libraries with adaptors and indices compatible with Illumina-based sequencing were generated by PCR. Resulting libraries were pooled and sequenced with an Illumina MiSeg™ instrument (500 cycle kit) so that the first sequencing read in paired-end mode covered the RNA sequence of interest. Resulting FASTQ data files were aligned to reference sequences and per-nucleotide mutation rates were calculated using an in-house pipeline (Example 5 herein). Phred scores used to count mutations were required to be ?_20.

Measurement of Internucleotide Interactions by Statistical Association Analysis.

To detect nucleotide reactivity interdependencies, all possible pairs of nucleotides were subjected to Yates' corrected version of Pearson's $\chi 2$ test of independence versus association (Yates F (1934) Supp J Roy Stat Soc 1:217-235). Yates' corrected chi-squared statistic was computed as:

$$\chi^2_{Yates} = \frac{N(|ad-bc|-0.5N)^2}{(a+b)(c+d)(a+c)(b+d)} \quad (1)$$

where $N=(a+b+c+d)$ is the total number of strands in the dataset, and a, b, c, and d are defined by the following 2×2 contingency table of the observed numbers of four possible co-occurrences:

|  | Nucleotide i | |
| --- | --- | --- |
| Nucleotide j | Not mutated 0 | Mutated 1 |
| Not mutated 0 | a | b |
| Mutated 1 | c | d |

A pair of nucleotides was taken to have a statistically significant association if $\chi_{Yates}^2 > 20$ (p<0.00001). With this high acceptance threshold for an individual nucleotide pair we expect to make no more than one false-positive determination for RNAs at least up to 500 nt long.

For pairs of nucleotides that passed the $\chi 2$ significance test, the sign and strength of the statistical association was determined by computing Pearson's correlation coefficient, $\rho$. In the case of two binary variables, $\rho$ is equal to Pearson's measure of association, the phi coefficient. The correlation coefficient and the chi-squared statistic are related:

$$\rho^2 = \chi^2/N \quad (2)$$

Although correlation coefficients were typically less than 0.05, coefficients were highly significant. Based on $\chi^2$ statistics, the probability that identified correlated nucleotides were independent was less than 0.00001.

The following guidelines were also imposed for nucleotide association analysis and clustering. The average number of modifications detected per read was required to be ~15% of the estimated number of single-stranded nucleotides, yielding an average equal to or greater than two mutations per read. Nucleotides with a mutation rate greater than 0.05 in the no-modification control were excluded from the $\chi 2$ calculation. Correlated nucleotide pairs with a SD of their correlation coefficient (estimated by bootstrapping) greater than 20% were not used as RNA interaction group (RING) constraints. Bootstrapping iterations were sufficiently large so that the absolute difference between bootstrapped and calculated correlation coefficients was less than 1%.

Spectral Clustering of Multiple Conformations in a Single RNA Ensemble.

Nucleotides making up an RNA define the dimensions of an abstract high-dimensional space, in which any single read of an RNA strand is represented by a point whose coordinates are defined by which of the nucleotides, if any, reacted with the chemical reagent (each coordinate is set to either 1 or 0, depending on whether the nucleotide that the coordinate represents was reactive or not). In this space, strands with similar structural conformations will tend to cluster, reflecting differences in frequency of modification profiles for each conformation. We used spectral clustering (Shi J, Malik J (2000) IEEE Trans Pattern Anal Mach Intell 22:888-905; Ng A Y, Jordan M I, Weiss Y (2002) Advances in Neural Information Processing Systems 14, eds Dietterich T G, Becker S, Ghahramani Z (MIT Press, Cambridge, Mass.), pp 849-856; Luxburg von U (2007) Stat Comput 17:395-416), which is particularly effective in finding arbitrarily shaped clusters, to define RNA structural clusters, without making any assumptions about the form of the data clusters.

To detect the presence of multiple structural conformations in an RNA pool using spectral clustering, we summarized the locations in the primary sequence (N nucleotides in length) of the nucleotides that were modified by the chemical reagent in M RNA strands, in a "hit" matrix, $H_{M \times N}$. This dataset was treated as a simple, complete, undirected, weighted graph, in which each nucleotide is represented by a vertex with all of the N vertices linked by edges. Each edge was assigned a weight corresponding to the similarity of the reactivity patterns of the two nucleotides, measured as the number of reads in the dataset in which both nucleotides were modified:

$$S = H^T H \quad (3)$$

This similarity matrix S was then used to construct normalized graph Laplacian matrix:

$$L_{NCut} = D^{-1/2} \cdot (D-S) \cdot D^{-1/2} \quad (4)$$

where D is a diagonal matrix, in which $D_{ii} = \Sigma_j S_{ij}$. The eigenvectors of matrix $L_{NCut}$ were used to perform a normalized cut partitioning of the dataset into clusters by cutting the edges between vertices in a way that minimized the sums of the weights of the cut edges and maximized the sum of weights of the preserved edges (Shi J, Malik J (2000) IEEE Trans Pattern Anal Mach Intell 22:888-905; Ng A Y, Jordan M I, Weiss Y (2002) Advances in Neural Information Processing Systems 14, eds Dietterich T G, Becker S, Ghahramani Z (MIT Press, Cambridge, Mass.), pp 849-856; Luxburg von U (2007) Stat Comput 17:395-416). In our application to RNA mutation data, the eigenvalues and eigenvectors of the normalized graph Laplacian matrix $L_{NCut}$ were used to (i) determine how many structural conformations are present in the studied RNA pool, (ii) estimate relative fractions of different conformations in the sample, and (iii) reconstruct mutation frequency profiles for the individual conformations. These procedures are described in detail in the following paragraphs. Spectral clustering was applied to adenosine and cytosine nucleotides that were modified with frequencies greater than 0.01. Strands with no modifications carry no information and were excluded from spectral clustering.

The eigenvalues were sorted in ascending order, from the smallest eigenvalue, $\lambda 1$, to the largest, $\lambda N$. The first eigenvalue, $\lambda 1$, is always zero. Eigenvalues express the effectiveness of each normalized cut partitioning of the vertices. The more effective a particular cut is in cutting edges between dissimilar vertices (such as those belonging to different clusters) while preserving edges between similar vertices (such as those belonging to the same cluster), the smaller its eigenvalue. Therefore, if a dataset has K distinct clusters, the first K eigenvalues will be distinctly smaller than the K+1 eigenvalue and the rest of the eigenvalues. Thus, to estimate the number of clusters, K, in a dataset, we chose K such that all eigenvalues $\lambda 2, \lambda 3 \ldots \lambda K$ were relatively small, and $\lambda K+1$ was relatively large. To make jumps between consecutive eigenvalues more apparent, "eigengaps" (defined as a difference $\Delta\lambda i = \lambda i+1 - \lambda i$, with the first eigengap, $\Delta\lambda 1$, set to zero) rather than eigenvalues were evaluated (Luxburg von U (2007) Stat Comput 17:395-416). In general, if a dataset has K clusters, the eigengap plot will have an outstanding eigengap in the K position (ΔλK) and also likely to the left of it, but not to the right of it.

Estimating Relative Fractions of Different Conformations in RNA Sample.

If a dataset has K clusters, eigenvectors ~x2 . . . ~xK can be used to assign individual RNA strands to clusters. Specifically, if a dataset of M strands is recognized to have K clusters, the strand scores are computed as:
as:

$$Y_{M\times(K-1)}=H\cdot[\vec{x}_2,\vec{x}_3,\ldots \vec{x}_K], \quad (5)$$

where $\vec{x}_2, \vec{x}_3 \ldots \vec{x}_K$ are the second to the K-th eigenvectors. The scores have K−1 dimensions, and the strands are partitioned into K clusters by performing K− means clustering of M data points in the K−1 dimensional score space.

Reconstructing Modification Frequency Profiles of Individual Conformations in an RNA Sample.

Once strands are assigned to clusters reflective of distinct conformations, the modification frequency profiles can be computed specifically for each conformation. The accuracy of such profile reconstruction was improved by computing the modification frequencies of each nucleotide separately using the following procedure. To compute the modification frequencies of nucleotide i, this nucleotide was first removed from the hit matrix H and then spectral clustering and strand partitioning by K-means clustering was performed on this reduced matrix (without the contribution of this nucleotide). Next, the modification frequency of nucleotide i was computed separately for each partitioned group of strands, yielding estimates for different conformations.

Three-Dimensional RNA Structure Modeling.

Three-dimensional RNA fold reconstruction was performed using a restrained molecular dynamics approach in which free energy bonuses were incorporated based on pairwise nucleotide correlations (Gherghe C M, et al., (2009) J Am Chem Soc 131(7):2541-2546; Lavender C A, et al., (2010) Biochemistry 49(24):4931-4933). Each nucleotide was modeled as three pseudoatoms corresponding to the phosphate, sugar, and base groups. Pairwise interactions including base pairing, base stacking, packing interactions, and electrostatic repulsion are approximated using square-well potentials (Ding F, et al. (2008) RNA 14(6):1164-1173). Accepted base-pairing arrangements (Serganov A, et al., (2006) Nature 441(7097): 1167-1171; Cate J H, et al. (1996) Science 273(5282):1678-1685; Kazantsev A V, Krivenko A A, Pace N R (2009) RNA 15(2):266-276) were used to constrain modeling.

To incorporate information from RING analysis, free energy potentials were applied during the discrete molecular dynamics (DMD) simulations between nucleotide pairs found to interact. A free energy bonus was included for interacting nucleotide pairs if the absolute correlation coefficient was above 0.025. Free energy potentials were not included if two nucleotides were implicated as being in contact by proximity in primary sequence or by participation in a common secondary structure element. For primary sequence neighbors, a free energy potential was not included between nucleotides within 11 positions in sequence. For secondary structure neighbors, potentials were not added for nucleotides in the same structural element. Structural elements were defined as nucleotides at positions $n_i$ and $n_j$ in a RING pair and nucleotides at positions $m_i$ and $m_j$ in any given base pair, if $|n_i-m_i|+|n_j-m_j|$ is less than or equal to 11 nucleotides. The 11-nt threshold was selected based on the number of base pairs in a single turn of an A-form RNA helix.

Free energy potentials were imposed between RING-correlated nucleotide pairs based on through-space distances between constituent nucleotides during simulations. For distances between correlated nucleotides within 36 Å and 23 Å, the applied bonuses were −0.3 and −0.6 kcal/mol, respectively. The maximum −0.6 kcal/mol bonus is equivalent to stabilization afforded by a single RNA stacking interaction in the molecular dynamics force field.

Molecular dynamics simulations were performed using the DMD engine with replica exchange (Ding F, et al., (2012) Nat Methods 9(6):603-608). Eight replicas were run in parallel for 1 million time units each with replica temperature factor values of 0.1000, 0.1375, 0.1750, 0.2125, 0.2500, 0.2875, 0.3250, and 0.3625. From each replica, models at every 100 time units were taken forward. This list of models was then filtered based on radius of gyration. Radii of gyration for these models were compared against a control simulation where no RING-based potentials were incorporated. For both RING-dependent and control models, radius of gyration histograms were constructed. The control histogram was scaled to minimize its difference from the experimental histogram, and the frequency of the control histogram was then subtracted from the experimental. For this difference histogram, a log-normal distribution was found by least-squares fitting that describes the distribution of radii of gyration for constraint-dependent collapsed structures. To be considered further, RING-dependent models had to be within a geometric SD of the geometric mean described by this fit distribution.

Following filtering by radius of gyration, the 250 models with the lowest energies were then analyzed by hierarchical clustering (Lavender C A, et al., (2010) Biochemistry 49(24):4931-4933). Clustering was performed considering rmsd values between analyzed models. Clustering was constrained such that maximum rmsd between any two constituent members of a cluster was less than the sum of the average and SD of the rmsd distribution predicted for the analyzed structure. The medoid of the most populated cluster was taken as the predicted structure.

Example 5

RNA Motif Discovery by SHAPE and Mutational Profiling (SHAPE-MaP)

Results

The MaP Strategy

Figure 6:
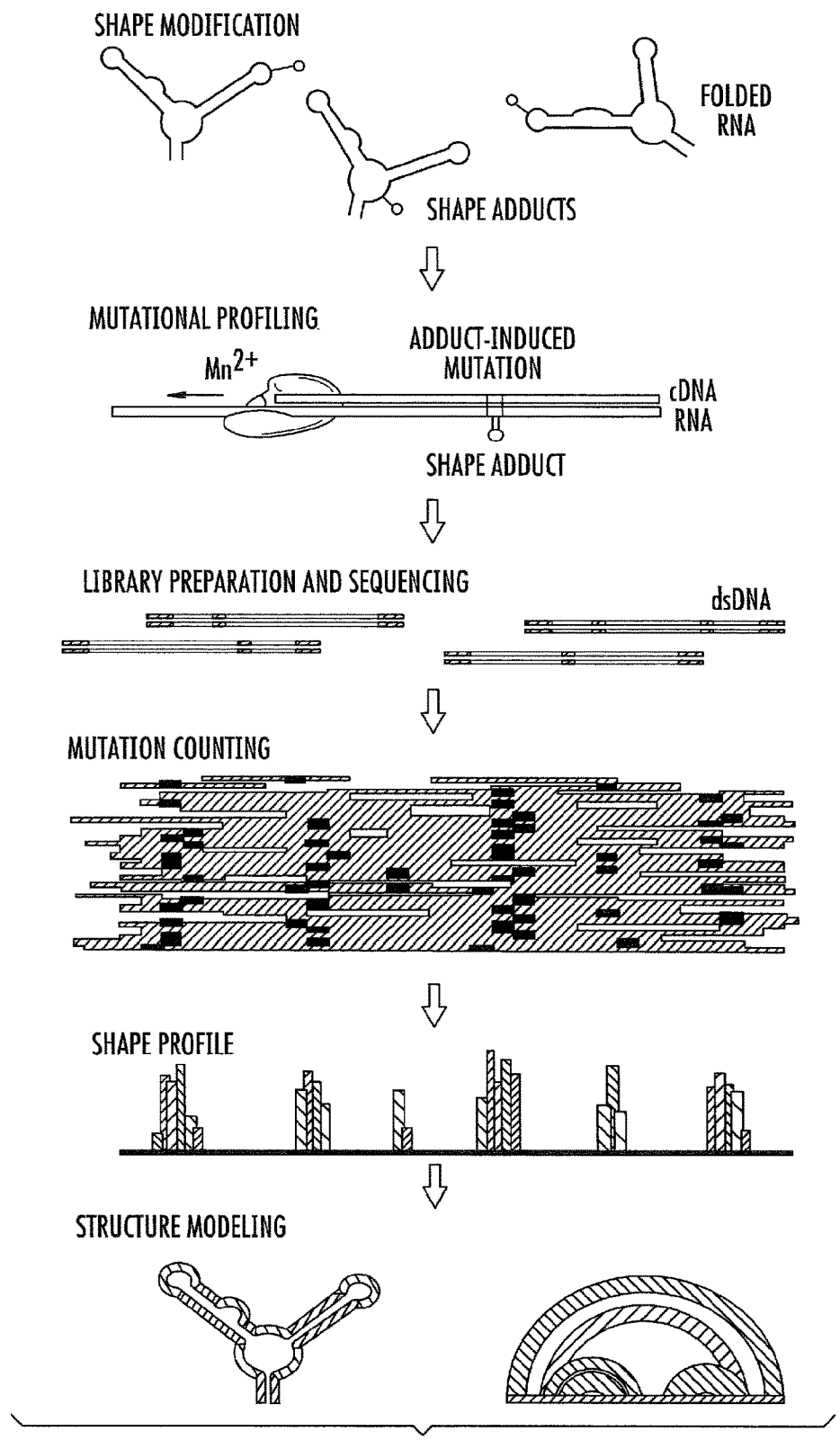
FIG. 6: SHAPE-MaP Overview. RNA is treated with a SHAPE reagent that reacts at conformationally dynamic nucleotides. During reverse transcription, the polymerase reads through chemical adducts in the RNA and incorporates a nucleotide non-complementary to the original sequence into the cDNA. The resulting cDNA is sequenced using any massively parallel approach to create mutational profiles (MaP). Sequencing reads are aligned to a reference sequence, and nucleotide-resolution mutation rates are calculated, corrected for background and normalized, producing a standard SHAPE reactivity profile. SHAPE reactivities can then be used to model secondary structures, visualize competing and alternative structures, or quantify any process or function that modulates local nucleotide RNA dynamics.

SHAPE experiments use 2'-hydroxyl-selective reagents that react to form covalent 2'-O-adducts at conformationally flexible RNA nucleotides, both under simplified solution conditions (Wilkinson, K. A. et al. *PLoS Biol.* 6, e96 (2008), Merino, E. J., et al., *J. Am. Chem. Soc.* 127, 4223-4231 (2005) and in cells (Tyrrell, J., et al., *Biochemistry* 52, 8777-8785 (2013); McGinnis, J. L. & Weeks, K. M. *Biochemistry* 53, 3237-3247 (2014); Spitale, R. C. et al. *Nat. Chem. Biol.* 9, 18-20 (2013)). SHAPE data can be employed as restraints in algorithms for prediction of RNA structure to provide highly accurate models of secondary structure for structurally complex RNAs (Example 3 herein above; Hajdin, C. E. et al. *Proc. Natl. Acad. Sci. USA* 110, 5498-5503 (2013). In this Example, SHAPE chemical modifications (Mortimer, S. A. & Weeks, K. M. *J. Am. Chem. Soc.* 129, 4144-4145 (2007); Example 3 herein above; Merino, E. J., et al. *J. Am. Chem. Soc.* 127, 4223-4231 (2005); Steen, K.-A., Rice, G. M. & Weeks, K. M. *J. Am. Chem. Soc.* 134, 13160-13163 (2012)) in RNA are quantified in a single direct step by massively parallel sequencing (FIG. 6). The approach exploits conditions that cause reverse transcriptase to misread SHAPE-modified nucleotides and incorporate a nucleotide noncomplementary to the original sequence in the newly synthesized cDNA.

Figure 9:
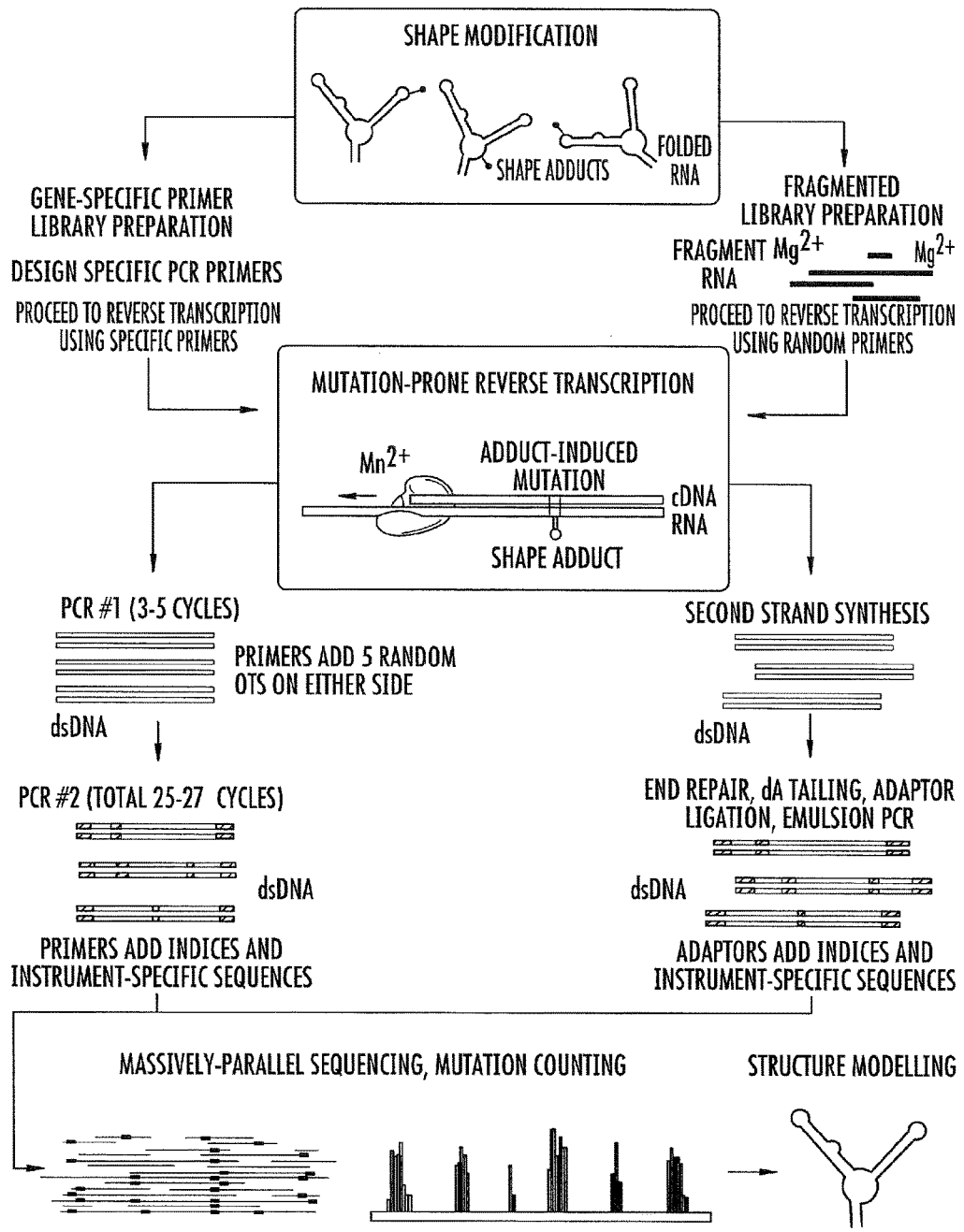
FIG. 9. Strategies for the SHAPE-MaP experiment using either gene-specific primers or random fragmentation for sample analysis and sequencing library preparation. SHAPE-MaP can be performed using gene-specific primers (for small RNAs or targeted areas in large RNAs and for analysis of scarce and low concentration RNAs) or random primers (for comprehensive analysis of large RNAs or complete transcriptomes) to create the initial cDNA pool. For both approaches, RNA is treated with a SHAPE reagent or with solvent under conditions of interest, and a sample of RNA is modified under denaturing conditions. For gene-specific samples, reverse transcription and PCR primers are designed based on the known target sequence. Large RNAs are randomly fragmented in a buffered $Mg^{2+}$ solution. Single-stranded cDNA was synthesized using mutation-prone reverse transcription; misincorporation events in the nascent cDNA mark the location of SHAPE adducts in the subject RNA. Double-stranded cDNAs were created either by PCR (gene-specific approach) or second-strand synthesis (randomly fragmented samples). Sequence platform-specific sequences (including multiplexing barcodes) were added to the dsDNA libraries, either directly through a second PCR (gene-specific approach) or by a DNA-DNA ligation of adaptor sequences (random fragmented samples). Libraries prepared by either method were then sequenced, producing data that were processed into SHAPE reactivity profiles used in structure modeling applications. SHAPE-MaP is fully independent of sequencing platform and library generation scheme (once the initial cDNA has been synthesized). Thus, any platform and any library generation scheme can be used.

The positions and relative frequencies of SHAPE adducts are thus immediately, directly and permanently recorded as mutations in the cDNA primary sequence, thereby creating a SHAPE-MaP. In a SHAPE-MaP experiment, the RNA is treated with a SHAPE reagent or treated with solvent only, and the RNA is modified under denaturing conditions to control for sequence-specific biases in detection of adduct-induced mutations. RNA from each experimental condition is reverse-transcribed, and the resulting cDNAs are then prepared for massively parallel sequencing. Reactive positions are identified by subtracting data for the treated sample from data obtained for the untreated sample and by normalizing to data for the denatured control (FIGS. 6 and 9).

Structure Modeling: Validation

The structure of the *Escherichia coli* thiamine pyrophosphate (TPP) riboswitch aptamer domain was initially examined in the presence and absence of saturating concentrations of the TPP ligand. SHAPE-MaP recapitulated the known reactivity pattern for the folded, ligand-bound RNA and accurately reported nucleotide-resolution reactivity differences that occur upon ligand binding. These results, and an analysis of the 1,542-nt *E. coli* 16S rRNA demonstrate the capacity of SHAPE-MaP to capture fine structural details for distinct RNA conformations at nucleotide resolution, accurately, reproducibly and independently of nucleotide type. Because SHAPE profiles are reconstructed from mutation frequencies derived from all sequencing reads, uncertainties in SHAPE reactivities can be estimated from the Poisson distribution of mutation events.

Figure 7A:
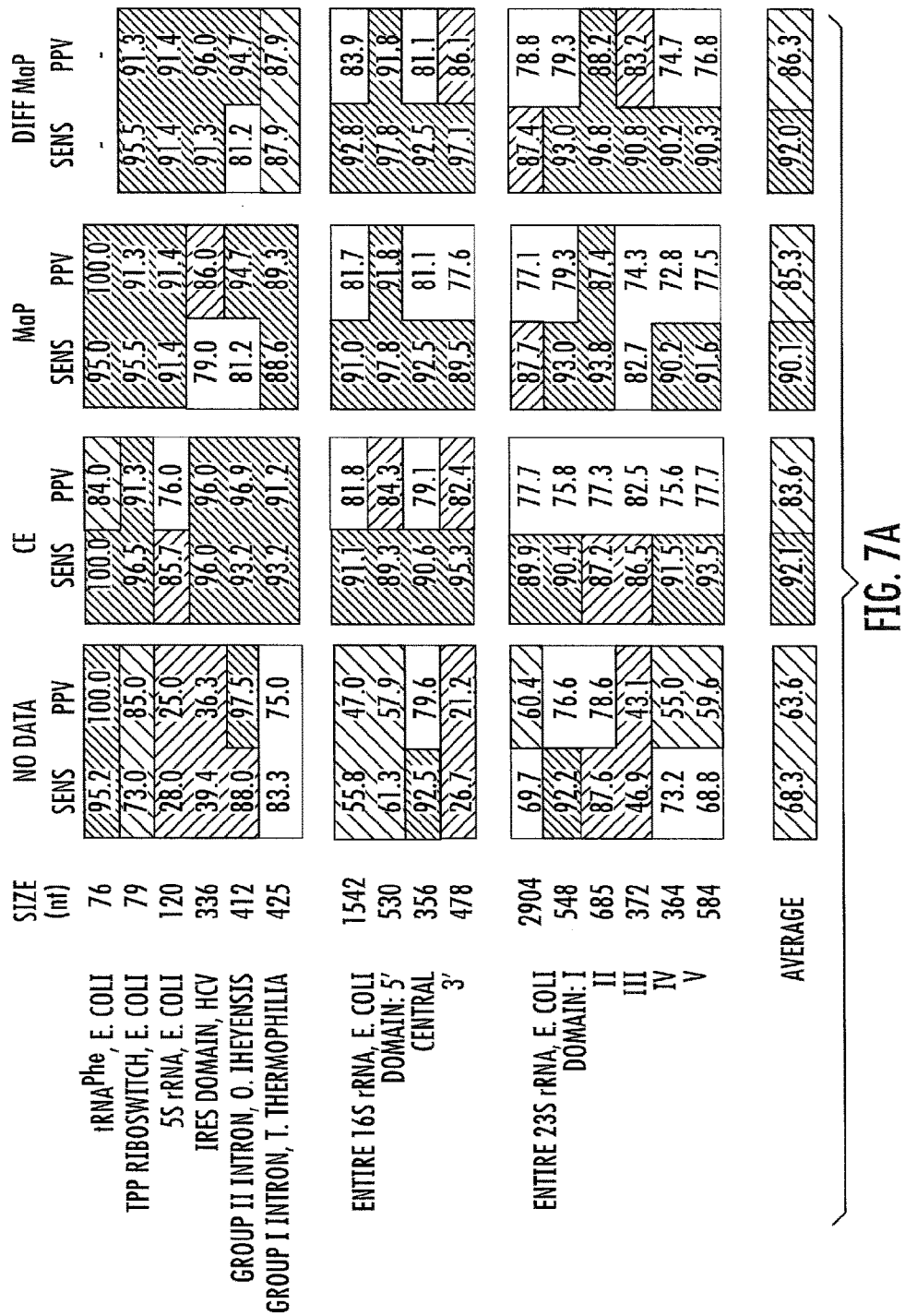
FIGS. 7A and 7B: Accuracy of SHAPE-MaP-directed secondary structure modeling.

Use of SHAPE data as pseudo-free energy change terms to constrain secondary-structure modeling has been extensively benchmarked using RNA test sets specifically chosen to be challenging to conventional secondary-structure modeling (Example 3 herein above; Hajdin, C. E. et al. *Proc. Natl. Acad. Sci. USA* 110, 5498-5503 (2013)). To assess the accuracy of SHAPE-MaP, a subset of these RNAs was probed, ranging in size from 78 nucleotides (nt) to 2,904 nt, with the well-validated 1M7 reagent. The 'differential' SHAPE experiment that uses two additional reagents, 1M6 and NMIA, was also evaluated to detect noncanonical and tertiary interactions and to yield RNA structural models with consistent high accuracy, even for especially challenging RNAs (Example 3 herein above; Steen, K.-A., Rice, G. M. & Weeks, K. M. Fingerprinting noncanonical and tertiary RNA structures by differential SHAPE reactivity. *J. Am. Chem. Soc.* 134, 13160-13163 (2012). The overall accuracy of SHAPE-MaP-directed modeling of RNA structure using differential reactivities, measured in terms of sensitivity and positive predictive value, was similar to and often superior to that of conventional SHAPE reactivities based on adduct-mediated termination of primer extension detected by capillary electrophoresis. The accuracy for recovery of accepted, canonical base pairs exceeded 90% (FIG. 7A).

Figure 7B:
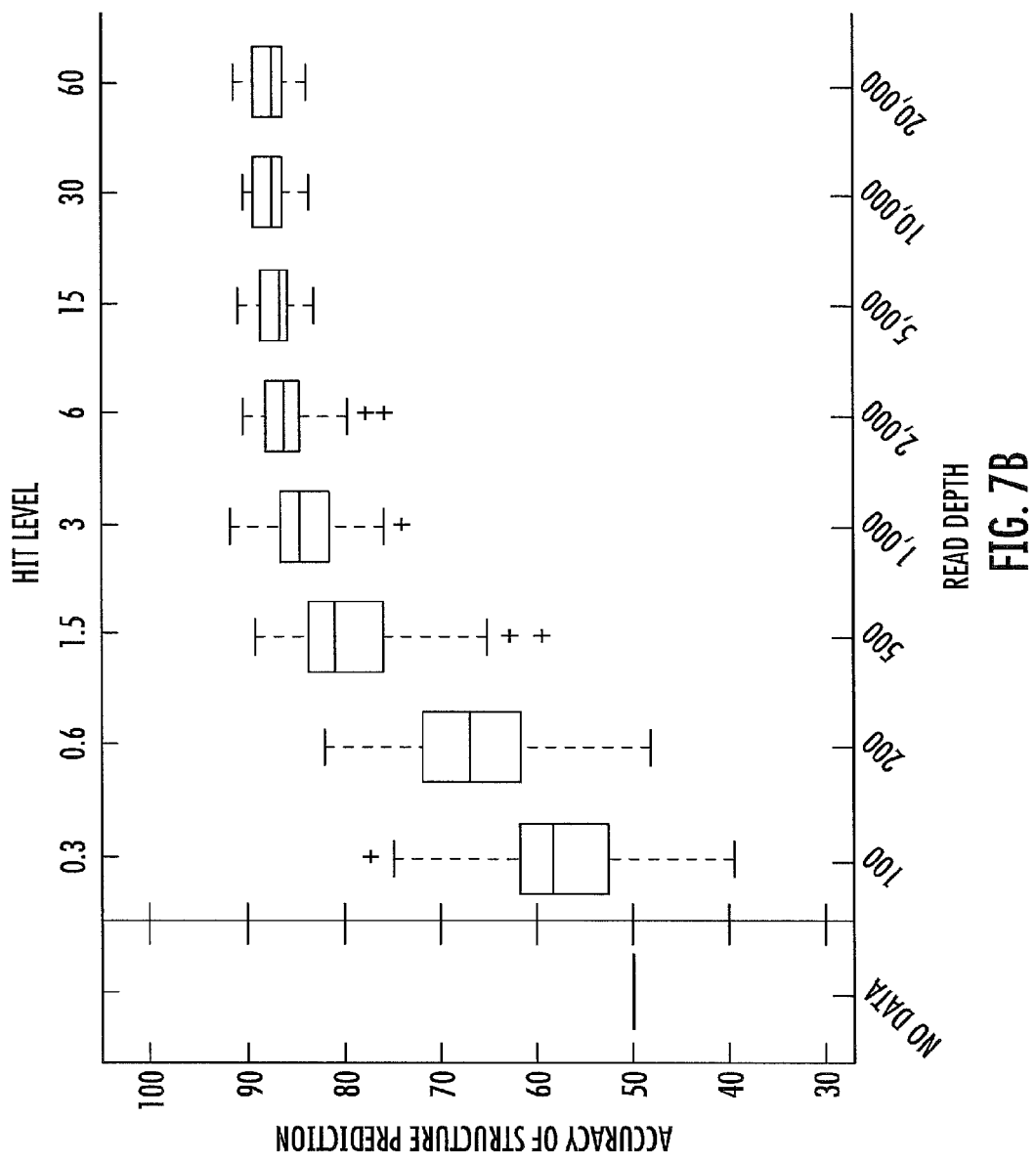

SHAPE reactivities obtained using the MaP strategy are measured as many individual events by massively parallel sequencing. Reliability depends on adequate measurement of mutation rates. Accurate modeling of the 16S rRNA structure using a per-nucleotide read depth of 2,000-5,000 was achieved. This corresponds to 6-15 modifications above background per ribosomal nucleotide on average (FIG. 7B). Although several prior studies (Kertesz, M. et al. *Nature* 467, 103-107 (2010); Ding, Y. et al. *Nature* 505, 696-700 (2014); Rouskin, S., et al. *Nature* 505, 701-705 (2014)) have been performed in which all of the RNAs in a given transcriptome were physically present during the probing phase of the experiment, this hit-level analysis indicates that only a few thousand nucleotides in each case were sampled at a depth that would allow full recovery of the underlying structural information. Accurate SHAPE-MaP-directed modeling was achieved using the same parameters originally defined for capillary electrophoresis-based experiments and comparable high accuracies using both RNA-specific and randomly primed experiments were achieved. Data were highly reproducible between full biological replicates performed months apart by different individuals, which emphasized the robustness of SHAPE-MaP.

An Updated, High-Resolution Model for an HIV-1 RNA Genome.

Single-nucleotide resolution structural information was obtained for an entire authentic HIV-1 genomic RNA (strain NL4-3, ~9,200 nt) in experiments and data analysis performed over roughly 2 weeks. 1M7 and differential SHAPE-MaP data were processed to yield profiles of SHAPE reactivity and models of secondary structure using efficient and fully automated algorithms (FIGS. 8 and 9). The MaP approach, implemented in this Example, yields nucleotide-resolution reactivity data for large RNAs that are equal or superior to the prior gold standard capillary electrophoresis data (FIG. 7A). Thus, the HIV-1 genome structure presented here constitutes a new, higher-resolution model for well-defined elements in this RNA.

De Novo Identification of Well-Determined Structures

Almost any long RNA sequence will form some secondary structures (Doty, P., et al. *Proc. Natl. Acad. Sci. USA* 45, 482-499 (1959)), but not all of these structures are biologically important or well-defined. Therefore, SHAPE-directed modeling, whose underlying energy function yields highly accurate models for RNAs with well-defined secondary structures (FIGS. 7A and 7B), was used to calculate a probability for each base pair across all possible structures in the Boltzmann ensemble of structures predicted for the HIV-1 RNA. These probabilities were used to calculate Shannon entropies (Huynen, M., Gutell, R. & Konings, D. *J. Mol. Biol.* 267, 1104-1112 (1997); Mathews, D. H. *RNA* 10, 1178-1190 (2004)) (FIG. 8). Regions with higher Shannon entropies are likely to form alternative structures, and those with low Shannon entropies correspond to regions with well-defined RNA structures or persistent single-strandedness, as determined by SHAPE reactivity. The plot of pairing probability across the entire HIV-1 genome reveals both well-determined and variable RNA structures in the HIV-1 genomic RNA (FIG. 8A). Previously characterized structured regions such as the 5' untranslated region (UTR), Rev response element (RRE), frameshift element and polypurine tract are well determined in the model. In contrast, there are also large regions (such as nucleotides 3,200-4,500 and 6, 100-6,800) that have high SHAPE reactivities and high Shannon entropy, and are therefore likely to sample many conformations. This visualization approach highlights regions with unique, likely stable structures and those regions in which multiple structures are likely to be in equilibrium.

Figure 8C:
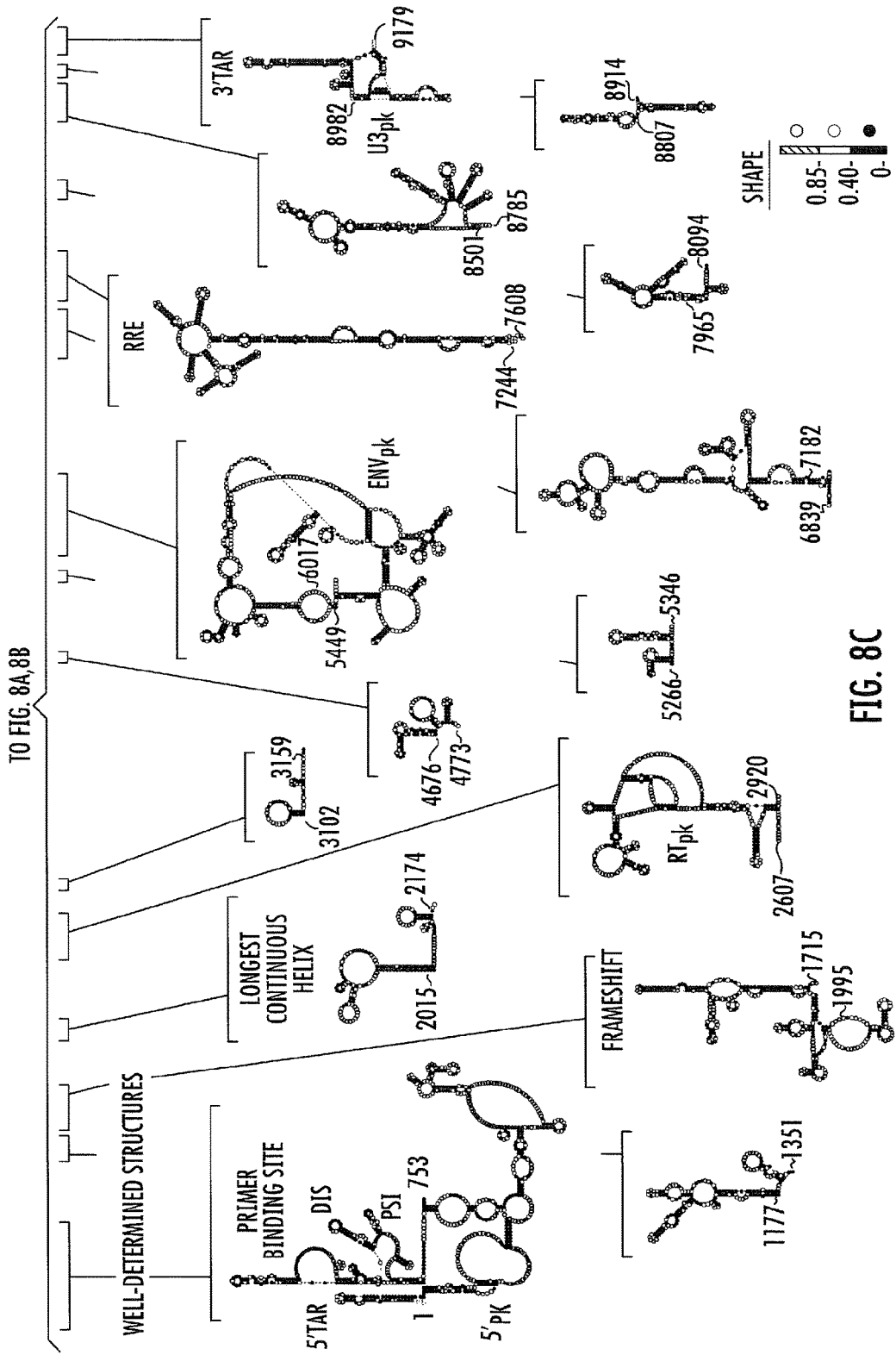

Analysis of Shannon entropies and SHAPE reactivities provides an approach for de novo discovery of regions with well-defined structure in long RNAs. Fifteen regions in the HIV-1 genomic RNA had both low SHAPE reactivity values (indicating a high degree of RNA structure) and low Shannon entropies (providing confidence in a single predominant secondary structure) (FIGS. 8A and 8B). Nucleotide-resolution structure models were created for each of these regions (FIG. 8C). The models of known, functionally important regulatory structures (RRE, 5' trans-acting responsive element (TAR), primer binding site, packaging element (Psi), dimerization initiation site, ribosomal frameshift element and 3' TAR) agreed closely with previously proposed models for these regions. In addition, the longest continuous helix, the hairpins flanking the polypurine tract and other features remain consistent between the prior (Watts, J. M. et al. *Nature* 460, 711-716 (2009)) and current model (Table 4).

Next, a list of all regulatory elements likely to function via an RNA motif (FIG. 8B and Table 5) was obtained. Then, the locations of these RNA structural elements were compared with the highly structured and low-entropy regions identified de novo by SHAPE-MaP. Functional RNA elements occur overwhelmingly in low-SHAPE, low-Shannon-entropy regions (P=0.002; FIG. 8), which indicates that most RNA-mediated functions operate in the context of an underlying RNA structure. Several low-SHAPE, low-Shannon-entropy regions in the HIV-1 genome occur in regions not previously associated with known RNA functional elements: these regions are high-value targets for discovery of new RNA motifs.

Motif Discovery and Deconvolution of Structural Polymorphism.

Pseudoknots appear to be rare in large RNAs and are difficult to identify, but these motifs appear to be overrepresented in functionally important regions of many RNAs (Staple, D. W. & Butcher, S. E. *PLoS Biol.* 3, e213 (2005); Brierley, I., Pennell, S. & Gilbert, R. J. C. *Nat. Rev. Microbiol.* 5, 598-610 (2007)). As a rigorous test of the current cumulative advances in SHAPE-directed structure modeling and of the high-throughput SHAPE-MaP data itself, a search (Hajdin, C. E. et al. *Proc. Natl. Acad. Sci. USA* 110, 5498-5503 (2013)) for new pseudoknots in the HIV-1 RNA genome was performed. In the model of this Example, there are four pseudoknots in regions of low SHAPE reactivity and low Shannon entropy (FIG. 8C). The pseudoknot adjacent to the 5' polyadenylation signal in the HIV-1 RNA ($5'_{PK}$) has been validated previously (Wilkinson, K. A. et al. *PLoS Biol.* 6, e96 (2008); Paillart, J.-C., et al. *J. Biol. Chem.* 277, 5995-6004 (2002)). The three additional new pseudoknots are predicted to form in the reverse transcriptase coding region ($RT_{PK}$), at the beginning of env ($ENV_{PK}$) and in the U3 region adjacent to the 3' polyadenylation signal ($U3_{PK}$). As a negative control, an additional pseudoknot predicted by the ShapeKnots algorithm that lies in a region of high SHAPE reactivity and high Shannon entropy ($CA_{PK}$, nucleotides 961-1,014) was analyzed.

Silent mutations designed to disrupt each pseudoknot were introduced into the full-length HIV-1 genome. Special features of the $U3_{PK}$ region illustrate the power of the MaP approach. U3 sequences occur at both the 5' and 3' ends of the viral genome in proviral HIV-1 DNA but only at the 3' end in the viral RNA. During transfection of the provirus-encoding plasmid, these sequences can undergo recombination. When mutations were introduced into the U3 sequence alone (at the 3' end) with the native-sequence U3 at the 5' end of the proviral DNA, SHAPE-MaP experiments revealed that both native and mutant sequences were present at the 3' ends of individual genomic RNAs in the sample containing mutant $U3_{PK}$. Because nucleotides are analyzed in the context of unfragmented RNA regions in the MaP approach, both alleles could be independently monitored in the same experiment, computationally separated, and individual SHAPE profiles for the native and mutant RNAs constructed. Notable differences in SHAPE reactivity were observed between native and mutant U3, produced by viruses in direct competition with each other and consistent with precise disruption of the $U3_{PK}$ structure. Mutations introduced in the 5' side of the $U3_{PK}$ pseudoknot helix induced changes in the predicted 3' pairing partner, located over 100 nucleotides away. SHAPE-MaP is thus particularly useful for structural analysis and motif discovery in systems that contain complex mixtures of RNAs, and for detecting and deconvoluting structural consequences of single-nucleotide and other allelic polymorphisms.

All mutant constructs were analyzed using SHAPE-MaP and in cell-based assays for viral fitness. Mutations in $U3_{PK}$ reduced viral spread in Jurkat cells by about tenfold relative to NL4-3 and reduced viral fitness in direct competition with NL4-3, with a mean relative fitness difference of –0.32 relative to NL4-3 31. This large effect on viral fitness by mutations in the U3PK is consistent with the general importance of 3' UTRs in regulating mRNA stability and translation (Matoulkova, E., et al. *RNA Biol.* 9, 563-576 (2012)) and, more particularly, with a role for specific higher-order spatial organization of the poly(A) signal and upstream sequence elements in assembly of the polyadenylation machinery (Gilmartin, G. M., et al. *EMBO J.* 11, 4419-4428 (1992); Klasens, B. I., et al. *Nucleic Acids Res.* 27, 446-454 (1999)). SHAPE changes in the $RT_{PK}$ mutant were also located directly in or immediately adjacent to the pseudoknotted helix. Mutations in $RT_{PK}$ showed a smaller, but reproducible, decrease in viral spread and viral fitness, with a mean relative fitness of –0.14, compared to NL4-3. Changes in SHAPE reactivities were also observed at both the 5' and 3' sequences for the 'long-distance' $ENV_{PK}$ mutant, including changes extending 5 from the pseudoknotted helix, which is suggestive of local refolding caused by disruption of this pseudoknot. Viral spread and viral fitness were not reduced for the $ENV_{PK}$ mutant, which might reflect the challenge of detecting some features of HIV-1 replication in cell culture. The mutations in $CA_{PK}$, which was analyzed as a negative control, did not support existence of a pseudoknotted structure at this location by SHAPE-MaP analysis, in agreement with the high Shannon entropy profile.

Discussion

With mutational profiling, nucleic acid structural information is directly and concisely recorded in the sequence of the complementary cDNA and rendered insensitive to biases in library preparation and massively parallel sequencing. MaP thus converts reverse transcription or DNA synthesis into a direct engine for nucleic acid structure discovery. MaP is fully independent of the sequencing strategy and can therefore be used in any sequencing approach with a sufficiently low base-call error rate to quantify chemical modifications in any low-abundance RNA detectable by reverse transcription. Detection of chemical adducts in both RNA and DNA via direct read through can be coupled with strategies for polymerase selection (Ghadessy, F. J. & Holliger, P. et al. *Methods Mol. Biol.* 352, 237-248 (2007); Chen, T. & Romesberg, F. E. *FEBS Lett.* 588, 219-229 (2014) to record, as mutational profiles or MaPs, a wide variety of post-transcriptional and epigenetic modifications.

SHAPE-MaP data contain error estimates and are readily integrated into fully automated, vetted algorithms for structure modeling and transcript-wide motif discovery. In large-scale and genome-scale studies of RNA structure, true functional elements can be identified in the background of the complex ensemble of structures that form in any large RNA. The combination of SHAPE-MaP analysis with analysis of pairing probabilities, calculated across large RNA regions, identified almost all known large-scale functional elements in the HIV-1 genome, with the exception of the central polypurine tract, which appears to have a conserved structure (Pollom, E. et al. PLoS Pathog. 9, e1003294 (2013)). Thus, the sensitivity of functional element detection by SHAPE-MaP is very high. Moreover, despite the fact that the HIV-1 genome is one of most intensively studied RNAs in scientific history, quantitative and high-resolution SHAPE-MaP analysis nonetheless allowed rapid, de novo discovery and direct validation of new functional motifs, specifically three pseudoknots, a motif that has traditionally been challenging to predict. The positive predictive value of the approaches developed here is thus also correspondingly high. SHAPE-MaP provides experimental simplicity and structural accuracy and can be scaled to RNA systems of any size and complexity.

Methods

SHAPE-MaP Experimental Overview.

SHAPE-MaP experiments use conditions for reverse transcription that promote incorporation of nucleotides non-complementary to the RNA into the nascent cDNA at the locations of SHAPE adducts. Sites of RNA adducts thus correspond to internal mutations or deletions in the cDNA, relative to comparison with cDNAs transcribed from RNA not treated with SHAPE reagent. Reverse transcription can be carried out using gene-specific or random primers (FIG. 9); both approaches are described below. Once cDNA synthesis is complete, RNA structural information is essentially permanently recorded in the sequence and is thus independent of biases introduced during any multistep library construction scheme. Library preparation is similar to that of an RNA sequencing (RNA-seq) experiment, can be readily tailored to any sequencing platform, and allows multiplexing using sequence barcodes. Single-stranded breaks and background degradation do not intrinsically interfere with SHAPE-MaP experiments (in contrast to conventional SHAPE and other reverse transcriptase stop-dependent assays), as these are not detected during read through sequencing. There is also no signal decay or drop-off in the MaP approach, which otherwise requires complex, partially heuristic, correction.

SHAPE-MaP Development and Efficiency.

Reverse transcriptase enzymes can, in some cases, read through unusual 2'-O-linkages and adducts, after enzyme pausing (Lorsch, J. R., Bartel, D. P. & Szostak, Nucleic Acids Res. 23, 2811-2814 (1995); Patterson, J. T., Nickens, D. G. & Burke, D. H. RNA Biol. 3, 163 (2006)). It is hypothesized that read-through causes, or results from, structural distortion in the reverse transcriptase active site, which results in a higher rate of nucleotide misincorporation at the location of a pause-inducing SHAPE adduct. Multiple reverse transcriptase enzymes were screened for use in SHAPE-MaP as a function of nucleotide concentration, reaction time, buffer conditions and divalent metal ion identity. Enzyme conditions were searched for that produced minimal adduct-induced reverse transcription stops and maximal full-length cDNA products. Of the divalent metal ions tested (including magnesium, manganese, copper, cobalt, nickel and lead), $Mn^{2+}$ most effectively promoted enzyme read-through at the sites of bulky 2'-O-adducts, particularly using a Moloney murine leukemia virus reverse transcriptase (SUPERSCRIPT™ II, Invitrogen). This observation is consistent with the high activity of the Moloney reverse transcriptase in $Mn^{2+}$ (Roth, M. J., Tanese, N. & Goff, S. P. J. Biol. Chem. 260, 9326-9335 (1985)) and the ability of this ion to promote mutagenic behavior in DNA polymerases (Beckman, R. A., Mildvan, A. S. & Loeb, L. A. Biochemistry 24, 5810-5817 (1985)). The precise classes of adduct-induced misincorporation events were determined by comparing substitution and deletion rates at nonpaired and paired nucleotide positions in the 16S rRNA.

Misincorporation trends were similar between all three SHAPE reagents (1M7 (Mortimer, S. A. & Weeks, K. M. J. Am. Chem. Soc. 129, 4144-4145 (2007))). and the 'differential' reagents NMIA and 1M6 (Example 3 herein above). Generally, the presence of a SHAPE adduct causes nucleotides to be misread as A or T, or as deletion events, although there is substantial information content in other misincorporation events. Flexible nucleotides in a dinucleotide model substrate with a single reactive position (AddC) (Mortimer, S. A. & Weeks, K. M. J. Am. Chem. Soc. 129, 4144-4145 (2007)) are modified with an efficiency of ~2% by NMIA or 1M7 under conditions similar to those used here. Mutation rates above background at flexible positions in the 16S rRNA are ≥0.5%, with many of the most reactive positions above 2%. Given these boundary values, it was estimated that the MaP strategy detects SHAPE adducts with an efficiency of ≥50%.

RNA Folding and SHAPE Probing of Model RNAs.

DNA templates (IDT) were synthesized for $tRNA^{Phe}$, TPP riboswitch, E. coli 5S, hepatitis C virus IRES domain, T. thermophila group I intron or O. iheyensis group II intron RNAs in the context of flanking 5' and 3' structure cassettes. Templates were amplified by PCR and transcribed into RNA using T7 RNA polymerase (Wilkinson, K. A., et al. Nat. Protoc. 1, 1610-1616 (2006)). RNAs were purified by denaturing PAGE, appropriate regions were excised, and RNAs were passively eluted from the gel overnight at 4° C. 16S and 23S rRNAs were isolated from DH5α cells during mid-log phase using nondenaturing conditions (Deigan, K. E., et al. Proc. Natl. Acad. Sci. USA 106, 97-102 (2009)). For each sample, 5 pmol of RNA was refolded in 100 mM HEPES, pH 8.0, 100 mM NaCl and 10 mM $MgCl_2$ in a final volume of 10 μl. After folding, RNAs were modified in the presence of 10 mM SHAPE reagent and incubated at 37° C. for 3 min (1M6 and 1M7) or 22 min (NMIA). No-reagent controls, containing neat DMSO rather than SHAPE reagent, were performed in parallel. To account for sequence-specific biases in adduct detection, RNAs were modified using NMIA, 1M7 or 1M6 under strongly denaturing conditions in 50 mM HEPES (pH 8.0), 4 mM EDTA and 50% formamide at 95° C. After modification, RNAs were isolated using either RNA affinity columns (RNeasy™ MinElute™; Qiagen) or G-50 spin columns (GE Healthcare).

RNA Folding and SHAPE Probing of the HIV-1 Genomic RNA.

For whole-genome SHAPE-MaP of HIV-1 (strain NL4-3; group M, subtype B), virus was produced and purified as described (Watts, J. M. et al. Nature 460, 711-716 (2009)). Viral RNA was gently extracted and purified from protein then precipitated with ethanol from a solution containing 300 mM NaCl. Approximately 30% of genomic RNA is full length when prepared in this manner (Watts, J. M. et al. Nature 460, 711-716 (2009)); the fragmented nature of native HIV-1 genome samples resulted in decreased sample recovery during column purifications (RNeasy™ MinElute™, Qiagen). Therefore, ~1 μg of HIV-1 RNA was used per sample, more RNA than the 250 ng required for SHAPE-MaP experiments of more intact RNAs. Mutant viruses were produced by transfection of 293T cells=using FuGene6™

(Promega) or XtremeGene™ HP (Roche). Viral supernatants were concentrated using centrifugal concentrators (Vivaspin™ 20, Sartorius), followed by precipitation (Lenti-X™ Concentrator, Clontech) to concentrate virions. Pelleted virions were resuspended in viral lysis buffer (50 mM HEPES (pH 8.0), 200 mM NaCl and 3 mM $MgCl_2$)(Watts, J. M. et al. *Nature* 460, 711-716 (2009)), and lysed with 1% (w/v) SDS and 100 µg/ml proteinase K (25° C., 30 min). RNA was extracted with phenol:chloroform:isoamyl alcohol at least three times, followed by two extractions with chloroform and precipitation with ethanol.

Approximately 1 µg of HIV-1 genomic RNA was suspended in modification buffer (50 mM HEPES (pH 8.0), 200 mM potassium acetate (pH 8.0) and 3 mM $MgCl_2$) and incubated at 37° C. for 15 min (for SHAPE modified and untreated samples) or in denaturing buffer (50 mM HEPES (pH 8.0), 4 mM EDTA and 50% formamide) and incubated at 95° C. for 2 min. Samples were then treated with SHAPE reagent (10 mM final) or neat solvent.

SHAPE-MaP Using Fragmented Samples.

After SHAPE modification and purification, HIV-1, group II intron, HCV IRES and rRNA samples were fragmented (yielding lengths of ~250-350 nt) by a 4-min incubation at 94° C. in a buffer containing 9 mM $MgCl_2$, 225 mM KCl and 150 mM Tris HCl (pH 8.3). RNA fragments were desalted using G-50 spin columns. Fragmented samples (250-500 ng total mass) were subjected to reverse transcription for 3 h at 42° C. (using SuperScript™ II, Invitrogen). Reactions were primed using 200 ng random nonamer primers (NEB) for the ribosome, group II intron and HCV IRES RNA or with custom LNA primers (FIG. 10) for HIV-1 RNA genomes. Reverse transcriptase buffer contained 0.7 mM premixed dNTPs, 50 mM Tris=HCl (pH 8.0), 75 mM KCl, 6 mM $MnCl_2$ and 14 mM DTT. After reverse transcription, reactions were desalted using G-50 spin columns (GE Healthcare). Under these conditions (long incubation times and using 6 mM $Mn^{2+}$ as the only divalent ion) the reverse transcriptase reads through sites of 2'-O-modification by a SHAPE reagent, incorporating a non-complementary nucleotide at the site of the adduct.

Double-stranded DNA libraries for massively parallel sequencing were generated using NEBNext™ sample preparation modules for Illumina. Second-strand synthesis (NEB E6111) of the cDNA library was performed using 100 ng input DNA, and the library was purified using a PureLink™ Micro PCR cleanup kit (Invitrogen=K310250). End repair of the double-stranded DNA libraries was performed using the NEBNext™ End Repair Module (NEB E6050). Reaction volumes were adjusted to 100 µl, subjected to a cleanup step (Agencourt AMPure™ XP beads A63880, 1.6:1 beads-to-sample ratio), d(A)-tailed (NEB E6053) and ligated with Illumina compatible forked adapters (TruSeq™) with a quick ligation module (NEB M2200). Emulsion PCR44 (30 cycles) using Q5 hot-start, high-fidelity polymerase (NEB M0493) was performed to maintain library sample diversity. Resulting libraries were quantified (Qubit™ fluorimeter; Life Technologies), verified using a Bioanalyzer™ (Agilent), pooled and subjected to sequencing using the Illumina MiSeq™ or HiSeq™ platform. A single replicate of the group II and HCV IRES RNAs were obtained, and SHAPE-MaP reactivities agreed well with previously generated reactivities derived from SHAPE-CE. For the HIV-1 RNA genome, two full biological replicates, at different reagent concentrations, were obtained. Analysis presented here is primarily based on one of these replicates (sequencing features are summarized in Table 5). Selected individual segments, including all pseudoknotted regions, were probed by both fragmented and directed (gene-specific) approaches and showed excellent agreement.

SHAPE-MaP Using Targeted Gene-Specific Primers.

The tRNAPhe, TPP riboswitch, 5S rRNA, group I intron and mutant HIV-1 construct RNAs were subjected to reverse transcription using a DNA primer specific to either the 3' structure cassette (5'-GAA CCG GAC CGA AGC CCG-3') (SEQ ID NO:8) for the small RNAs or to specific HIV-1 sequences flanking a pseudoknot using buffer and reaction conditions described above. Sequencing libraries were generated using a modular, targeted, two-step PCR approach that makes it possible to inexpensively and efficiently generate data for many different RNA targets. PCR reactions were performed using Q5 hot-start, high-fidelity DNA polymerase. The forward PCR primer (5'-GAC TGG AGT TCA GAC GTG TGC TCT TCC GATC NNNNN-gene-specific primer-3') (SEQ ID NO:9) includes an Illumina-specific region at the 5' end, followed by five random nucleotides to optimize cluster identification on the MiSeq™ instrument and ends with a sequence complementary to the 5' end of the target RNA. The reverse primer (5'-CCC TAC ACG ACG CTC TTC CGA TCT NNNNN-gene-specific primer-3') (SEQ ID NO:10) includes an Illumina-specific region followed by five random nucleotides and a sequence that is the reverse complement of the 3' end of the target RNA. The cDNA library was 'tagged' by limited, 5-cycle PCR for amplicons or a longer 25-cycle PCR reaction when very low RNA concentrations were used. Excess primer, not used in the first few cycles, was removed (PureLink™ Micro PCR cleanup kit; Invitrogen). The second round of PCR added the remaining Illumina-specific sequences needed for on-flow cell amplification and barcoded the samples for multiplexing. The forward primer (CAA GCA GAA GAC GGC ATA CGA GAT (Barcode) GT GAC TGG AGT TCA GAC) (SEQ ID NO:11) contains a barcode and targets sequence in the forward primer from PCR 1. The reverse primer (AAT GAT ACG GCG ACC ACC GAG ATC TAC ACT CTT T CCC TAC AC GAC GCT CTT CCG) (SEQ ID NO:12) contains an Illumina-specific sequence and targets the reverse primer from PCR 1. PCR 2 was performed for 25 or 5 cycles to generate the final library for sequencing (not exceeding 30 total cycles). Typical SHAPE-MaP experiments of mutant viruses used ~150 ng to 200 ng of RNA per experimental condition. However, when material is limiting, as little as 50 ng input RNA is sufficient.

SHAPE-MaP Data Analysis Pipeline.

A data-analysis pipeline, called ShapeMapper, was created, which can be executed on most Unix-based platforms and accepts as input sequencing read files in FASTQ format, reference sequences in FASTA format and a user-edited configuration file. Without additional user intervention, the software creates a SHAPE reactivity profile and standard error estimates for each reference sequence. Other useful outputs are provided including mutation counts, sequencing depths and predicted secondary structures. The analysis software incorporates several third-party programs. Python 2.7 is required (python.org/); Bowtie™ 2 software is used for read alignment (Langmead, B. & Salzberg, S. L. *Nat. Methods* 9, 357-359 (2012)); reactivity profiles are generated using the python library matplotlib (Hunter, J. D. *Comput. Sci. Eng.* 9, 90-95 (2007)); prediction of secondary structure used RNAstructure™ (Reuter, J. S. & Mathews, D. H. *BMC Bioinformatics* 11, 129 (2010)) software; and drawing of secondary structure uses the Pseudoviewer™ web service (Byun, Y. & Han, K. *Nucleic Acids Res.* 34, W416-W422 (2006)).

Configuration.

A configuration file is used to specify the reference sequences present in each sample and which samples should be combined to create reactivity profiles. The format is flexible, allowing the alignment of each sample to multiple sequence targets as well as the treatment of multiple samples in unified analyses. Parameters for each stage of analysis may also be customized.

Quality Trimming.

Input reads were separated into files by sequencing barcode (this step is integrated into most sequencing platforms). The first analysis stage trims reads by base-call quality. Each read was trimmed downstream of the first base-call with a phred quality score below 10, corresponding to 90% expected accuracy. Reads with 25 or more remaining nucleotides were copied to new FASTQ files for alignment.

Read Alignment.

Reads were locally aligned to reference sequences using Bowtie™ 2 (Langmead, B. & Salzberg, S. L. *Nat. Methods* 9, 357-359 (2012)); parameters were chosen to provide high sensitivity, to detect single nucleotide mismatches, and to allow deletions of up to about 200 nucleotides. Seed length (-L) was 15 nucleotides. One mismatch was allowed per seed (-N). Maximum seed attempts (-D) was set at 20. Maximum 're-seed' attempts (-R) was set at 3. Dynamic programming padding (-dpad) was set at 100 nucleotides. The match bonus (-ma) was 2. The maximum and minimum mismatch penalties (-mp) were 6 and 2, respectively. Gap open and extend parameters (-rdg, -rfg) were 5 and 1, respectively. The default minimum alignment score function was used. Soft-clipping was turned on. Paired-end alignment was used by default. Bowtie™ 2 outputs aligned reads as SAM files.

Alignment Parsing, Ambiguous Alignment Removal and Mutation Counting.

Paired-end reads in SAM files were combined, and higher-quality base-calls were selected where read pairs disagreed. Mismatches and deletions contribute to mutation counts; insertions were ignored. As error-prone reverse transcription generates most of the mutations in each read, we treated a sequence change covering multiple adjacent nucleotides as a single mutation event located at the 3'-most nucleotide. If random primers were used, a region one nucleotide longer than the length of the primer was excluded from the 3' end of each read. Reads with mapping qualities <30 were excluded. Deletions are an important part of the mutation signal, but deletions that are ambiguously aligned can blur this signal, preventing single-nucleotide resolution. To resolve this problem, a simple local realignment was performed to identify and remove ambiguously aligned deletions. The reference sequence surrounding a deletion was stored. The deletion was then slid upstream or downstream one nucleotide at a time to a maximum offset equal to the deletion length. At each offset, the surrounding reference sequence was compared to the stored sequence. If any offset sequence matched, this indicated a possible alternate alignment, and the deletion was excluded. This algorithm correctly identified ambiguous deletions in homopolymeric regions as well as repeated sequences.

Reactivity Profile Creation.

The mutation rate (mutr) at a given nucleotide is simply the mutation count (mismatches and unambiguously aligned deletions) divided by the read count at that location. Raw reactivities were generated for each nucleotide using the following expression, where S corresponds to a SHAPE-modified sample, U to untreated sample and D to reaction under denaturing conditions:

$$R = \frac{mutr_S - mutr_U}{mutr_D} \quad (1)$$

The standard error (stderr) associated with the mutation rate at a given nucleotide in the S, U, or D samples was calculated as:

$$stderr = \frac{\sqrt{mutr}}{\sqrt{reads}} \quad (2)$$

The final standard error of the reactivity at a given nucleotide is:=

$$= \sqrt{\left(\frac{stderr_S}{mutr_D}\right)^2 + \left(\frac{stderr_U}{mutr_D}\right)^2 + \left(stderr_D \times \frac{(mutr_S - mutr_U)}{mutr_D^2}\right)^2} \quad (3)$$

Reactivities were normalized to a standard scale that spanned zero (no reactivity) to ~2 (high SHAPE reactivity) as described (Hajdin, C. E. et al. *Proc. Natl. Acad. Sci. USA* 110, 5498-5503 (2013)). Nucleotides with mutation rates greater than 5% in no-reagent control samples were excluded from analysis, as were nucleotides with sequencing depths less than 10 in any sample. A much greater depth is required for high-quality data and structure modeling (see FIGS. 7A and 7B).

Final Data Output.

SHAPE reactivity profiles (.shape) were output as tab-delimited text files with the first column indicating nucleotide number and the second column indicating reactivity. A SHAPE-MaP reactivity file was also output (.map). This file is in the SHAPE file format with the addition of two columns: standard error and nucleotide sequence. Another file (.csv) containing mutation counts, read depths, mutation rates, raw reactivities, normalized reactivities and standard errors for SHAPE-modified, untreated and denatured samples was also created. Files containing figures showing mutation rate histograms, sequencing depths and reactivity profiles may be generated (.pdf). These are useful in diagnosing potential experimental problems (including insufficient sequencing depth or low efficiency of mutagenesis).

Automatic RNA Folding and Structure Drawing by the SHAPEMaP Pipeline.

For sequences shorter than ~4,000 nucleotides and with sufficient read depth, the automated pipeline allows secondary structures to be automatically modeled using RNAstructure™ software, although this capability was not used for the RNAs in this work. FASTA sequence files are converted to SEQ files required by RNAstructure™ software. SHAPE reactivities are incorporated into RNAstructure™ as pseudo-free energies using standard parameters for the 1M7 reagent (Hajdin, C. E. et al. *Proc. Natl. Acad. Sci. USA* 110, 5498-5503 (2013)) (slope (-sm) 1.8, intercept (-si) −0.6). Differential SHAPE reagents are supported by RNAstructure™ software and are incorporated into a version of the automated pipeline. Predicted structures are written to .ct files. The lowest-energy predicted secondary structures can be drawn and annotated by SHAPE reactivity. This stage queries the Pseudoviewer™ web service (Byun, Y. & Han, K. *Nucleic Acids Res.* 34, W416-W422 (2006)) over an active internet connection. A custom client (pvclient.py) submits server requests and retrieves responses. This client also handles coloring of nucleotides by reactivity. Colored structure drawings are vector .eps files. Structures are also automatically converted to .xrna files (ma.ucsc.edu/rnacenter/xrna/) for optional manual editing.

Filtering by Z Factor for Differential SHAPE Data.

SHAPE-MaP allows errors in SHAPE reactivity measurements to be estimated from a Poisson distribution describing the measured mutation rates at each nucleotide. The Poisson-estimated SHAPE reactivity error can be used to evaluate statistical significance when comparing two SHAPE signals. Significant differences between NMIA and 1M6 reactivity were identified using a Z-factor test (Zhang, J., Chung, T. & Oldenburg, K. *J. Biomol. Screen.* 4, 67-73 (1999)). This nucleotide-resolution test compares the absolute difference of the means with the associated measurement error:

$$Z_{factor} = 1 - \frac{3(\sigma_{NMIA} + \sigma_{1M6})}{|\mu_{NMIA} - \mu_{1M6}|} \quad (4)$$

Each nucleotide in a SHAPE-MaP experiment has a calculated reactivity $\mu$ and an associated standard error $\sigma$. The significance threshold for Z factors was set at Z>0, equivalent to a SHAPE reactivity difference for 1M6 and NMIA of at least 3 standard deviations (s.d.). Differential nucleotide reactivities that did not meet this significance criterion were set to 0.

Structure Modeling.

Secondary structure modeling for RNAs less than 700 nt in length was performed as described (Example 3 hereinabove; Hajdin, C. E. et al. *Proc. Natl. Acad. Sci. USA* 110, 5498-5503 (2013)); differential SHAPE data were incorporated after filtering by Z factor. For the HIV-1 RNA genome, we developed an automated windowed modeling approach, implemented in a SHAPE-MaP Folding Pipeline, in which structure calculations were broken into stages designed to increase computational efficiency, generate realistic RNA structures and reduce end-effects caused by selecting a false 5' or 3' end from an internal fold in a window. This approach facilitated pseudoknot discovery, identification of probable base pairs and generation of minimum free energy structures. Representative calculations for folding of ribosomal subunits, performed using both one-step and windowed folding showed comparable, high degrees of accuracy and substantial reductions in computation 'wall time' using a typical desktop workstation for the windowed folding approach. For shorter RNAs, such as the 16S rRNA, there is a modest performance penalty for breaking the RNA into smaller windows. However, for RNAs longer than ~2,000 nucleotides, computation time scales approximately linearly with length.

Nearly all known and well-validated functional RNA structures are modeled identically in the current study and the prior investigation (Watts, J. M. et al. *Nature* 460, 711-716 (2009) and Table 4). Substantial improvements in digital (MaP) data acquisition, improved SHAPE-based energy functions Example 3 hereinabove; Hajdin, C. E. et al. *Proc. Natl. Acad. Sci. USA* 110, 5498-5503 (2013) and automated data analysis (FIG. 9) favor the current HIV-1 structure models over previous models in regions of disagreement. This Example also reflects other innovations and analysis, notably that not all regions of an RNA are likely to form a single well-defined structure. As a result, an aspect of this Example is the identification of regions in the HIV-1 RNA genome that do not form single well-defined structures.

Pseudoknot Prediction.

During the first stage, the full-length HIV-1 RNA genome was folded in 600-nt sliding windows moved in 100-nt increments using ShapeKnots with slope, intercept, P1 and P2 parameters set to previously defined values (1.8, −0.6, 0.35, 0.65) using 1M7 SHAPE data (Example 3 hereinabove; Hajdin, C. E. et al. *Proc. Natl. Acad. Sci. USA* 110, 5498-5503 (2013)). Additional folds were computed at the ends of the genome to increase the number of windows that cover terminal sequences. Predicted pseudoknots were retained if the structure appeared in a majority of windows and had low SHAPE reactivity on both sides of the pseudoknotted helix. This list of pseudoknots was used for all later stages of modeling.

Partition Function Modeling.

The partition function was calculated using Partition™ (Mathews, D. H. *RNA* 10, 1178-1190 (2004); Reuter, J. S. & Mathews, D. H. *BMC Bioinformatics* 11, 129 (2010) software and included both 1M7 and differential SHAPE data in the free energy penalty. The max pairing distance was set to 500 nt. Partition was run in 1,600-nt windows with a step size of 375 nt. Two extra windows (lengths of 1,550 nt and 1,500 nt) were run on the 5' and 3' end sequences to increase sampling at the true ends and to reduce the effect of non-optimal cut-site selection. Six sequences (the primer binding site, dimerization sequence and four pseudoknots known to be involved in unusual or special interactions) were constrained as single-stranded during partition function calculations. From the individual partition function files, the Shannon entropy of base pairing was calculated as:

$$H_i = -\Sigma_{j=1}^{J} p_{i,j} \log_{10} p_{i,j} \quad (5)$$

Where $p_{i,j}$ is the probability of pairing for nucleotides i and j over all potential J partners (Huynen, M., et al. *J. Mol. Biol.* 267, 1104-1112 (1997)). Following this calculation, 300 nt were trimmed from the 5' and 3' ends of each window that did not flank the true 5' and 3' ends of the RNA. This calculation retained more consistent internal values and discarded values skewed by end effects. Shannon entropy windows were combined by averaging, creating a single entropy file.

Individual probable pairs from each window were then trimmed using the same approach outlined for the Shannon entropy. Base pairs that formed with a probability less than $10^{-4}$ were removed to decrease computation time. Windows were combined and all remaining pairs were averaged over all of the windows in which they could have appeared. A heuristic color scale was developed from the combined partition file to indicate relative likelihood of a pair appearing in the final structure. The resulting pairs were plotted as arcs (FIG. 8). Base pairs with a probability greater than 0.99 were used as double-stranded constraints in the next step.

Minimum Free-Energy Modeling.

A minimum free energy structure was generated using Fold™ (Reuter, J. S. & Mathews, D. H. *BMC Bioinformatics* 11, 129 (2010)), 1M7 SHAPE data and differential SHAPE data. A window size of 3,000 nt with a step size of 300 nt was used to generate potential structures over each window. Four folds (3,100 nt, 3,050 nt, 2,950 nt and 2,900 nt from the ends) were also generated to increase the number of structure models at the termini. These folds from overlapping windows were then combined into a complete structure by comparing base pairs common to each window and requiring that pairs in the final structure appear in a majority of potential windows. As a final step, pseudo-knotted helices were incorporated.

Analysis of Error and Determination of a Minimum Number of Reads Required for Accurate Modeling of RNA Structure.

The mutation rates for each of the contributing signals (SHAPE-modified, untreated, denatured) were modeled using a Poisson distribution because discrete events from individual reads contribute to the overall signal. The variance of a Poisson distribution is equal to the number of observations; thus, the standard error (SE) of a 'true' rate can be modeled as:

$$SE_{rate} = \frac{\sqrt{\lambda}}{reads} = \frac{\sqrt{rate}}{\sqrt{reads}} \quad (6)$$

where $\lambda$ is the number of events (mutations observed), reads is the read depth at the modeled nucleotide (both mutations and non-mutations), and rate is the number of events per read. As expected, bootstrapping of the standard error of SHAPE reactivity showed an $x^{-1/2}$ power relationship as a function the read depth.

Using a deeply sequenced RNA (greater than 50,000 reads for each nucleotide), the number of expected mutation events at much lower read depths is known with high precision. Mutation events can be sampled from a Poisson distribution across the entire RNA to create profiles of plausible SHAPE data. To determine a minimum threshold for number of reads necessary for accurate SHAPE-directed modeling of secondary structure, we examined the 16S rRNA because it is modeled poorly in the absence of experimental data (~50% sensitivity). For each simulated read depth, we created 100 SHAPE trajectories based on the expected Poisson variance at the simulated read depth and modeled it using RNAstructure Fold™ software (FIG. 7B). As expected, modeling accuracy improved as read depth increased. For accurate nucleotide-resolution structure modeling, at least 5,000 reads are suggested, but even at 500 reads, the measurement is useful for structure modeling (FIG. 7B).

Hit-Level Calculation and Comparison with Other Reports.

SHAPE-MaP structure analysis as read out by massively parallel sequencing presents a valuable tool for structural interrogation of RNA at a single nucleotide level. Several other approaches have been developed with similar goals. To compare the read depth requirement of SHAPE-MaP (and its mutational profiling readout) with other approaches, a 'hit level' was calculated. The hit level metric quantifies the total background-subtracted signal per nucleotide of transcript:

$$\text{hit level} = \frac{\text{total events}_S - \frac{\text{read depth}_S}{\text{read depth}_B} \times \text{total events}_B}{\text{transcript length}} \quad (7)$$

where the subscripts S and B indicate the experimental sample and background control, respectively; events are either ligation detected sequence stops or mutations, depending on readout method, and read depth corresponds to the median number of reads overlapping each nucleotide in the transcript. A hit level of 160 was obtained for the 16S rRNA. As mutation counts in SHAPE MaP are proportional to read depths, the relationship between sequencing read depth and hit level was estimated by dividing our observed hit level by the median read depth in an experimental condition. A hit level of ~15 is required to fully recover RNA structure information as interrogated by SHAPE, although highly useful structure models were consistently obtained at hit levels as low as 5 (FIG. 7B). Probing and modeling of high-resolution RNA structure requires that most or all of an RNA be interrogated at a high hit level. Individual regions probed at low hit levels, even if the overall average hit level is ≥5, are likely to contain notable errors. In parallel analysis of RNA structure (PARS) experiments, a minimum threshold of 1 average read stop per nucleotide of transcript was required (Kertesz, M. et. al. Nature 467, 103-107 (2010); Wan, Y. et al. Nature 505, 706-709 (2014)); corresponding to hit level of 1, assuming zero background for enzymatic cleavage data. Similarly, a report describing DMS chemical probing, structure-seq, used a similar threshold of ≥1 average stop per A or C nucleotide 10; this corresponds to an estimated hit level (as defined herein) of 0.2, assuming a signal: background ratio of 1.7 (estimated from Ding, Y. et al. Nature 505, 696-700 (2014); extended data FIG. 1d) and that half of all transcript nucleotides are A or C. A minimum of 15 reads per A or C on average was required by the creators of DMS-seq11. This corresponds to a hit level of 3.3, assuming a signal:background ratio of 1.8 (estimated from Rouskin, S., et al. Nature 505, 701-705 (2014) FIG. 1c). The benchmarking and bootstrapping analysis for modeling accuracy reported here (FIG. 7B) has not been implemented in prior massively parallel sequencing-based RNA structure analyses (Kertesz, M. et al. Nature 467, 103-107 (2010), Underwood, J. G. et al. Nat. Methods 7, 995-1001 (2010), Lucks, J. B. et al. Proc. Natl. Acad. Sci. USA 108, 11063-11068 (2011), Ding, Y. et al. Nature 505, 696-700 (2014), Rouskin, S., et al. Nature 505, 701-705 (2014), Wan, Y. et al. Nature 505, 706-709 (2014)). This hit level analysis emphasizes that, although several prior studies have been performed in which the full complement of RNAs in a given transcriptome were present during the probing phase of the experiment, only a few thousand nucleotides in each case were sampled at a depth consistent with recovery of the underlying structure information obtainable using DMS or enzyme probes. (Underwood, J. G. et al. Nat. Methods 7, 995-1001 (2010)).

Algorithmic Discovery of HIV-1 Regions with Low Shannon Entropy and Low SHAPE Reactivity.

Overlap of regions with both low SHAPE reactivity and low Shannon entropy were used to identify regions likely to have a single well-determined structure. First, local median SHAPE reactivity and Shannon entropy were calculated over centered sliding 55-nt windows. Next, regions were selected in which the local median fell below the global median for more than 40 nt in both Shannon entropy and SHAPE reactivity. Regions were combined if they were separated by fewer than 10 nt. Finally, regions were expanded to include nested secondary structures from the minimum predicted free-energy model.

To exclude the possibility that the algorithmically discovered structured regions overlapped known RNA elements merely by chance, a randomized pool of segments was generated and the expected distribution of overlapping nucleotides (Table 4) was calculated. The same number and length of segments were maintained but their locations in the 9,173-nt genome were randomized. Out of 105 trials, only 219 showed a larger overlap than was observed, corresponding to a P value of 0.002.

HIV-1 Mutagenesis.

Mutations were introduced into HIV-1 pNL4-3 subclones spanning the region of interest by site-directed mutagenesis (QuikChange™ XL, Agilent) and verified by sequencing. The mutated subclone fragment was reintroduced into the full-length pNL4-3 plasmid (Adachi, A. et al. *J. Virol.* 59, 284-291 (1986)). The full-length mutant genome sequence was verified by conventional automated sequencing using 16 or more overlapping primers. Viruses from mutant and wild-type N L4-3 plasmids were produced by transfection as outlined above (to yield ~12 ng viral RNA per ml viral supernatant). Virion production was measured by p24 assay (AlphaLISA™ HIV p24 kit, PerkinElmer AL207C). Viruses were measured for infectivity on TZM-bl indicator cells53 (using Glo Lysis™ buffer and the Luciferase Assay System; Promega).

Mutations were designed to disrupt the primary pseudoknot sequence but maintain amino acid identity in coding sequences. The primary pseudoknotted helix in $U3_{PK}$ partially overlaps a binding site for transcription factor SP1. A total of three consecutive SP1 binding sites exist in HIV-1. Two point mutations introduced into the $U3_{PK}$ construct overlap the third SP1 binding site. Previous work has demonstrated that only a single binding site is required for complete viral function (Harrich, D. et al. *J. Virol.* 63, 2585-2591 (1989). The SP1 protein tolerates variation at several places in the binding consensus sequence, and the mutations introduced here maintained a canonical SP1 binding site. To analyze effects on virus production resulting from the SP1 mutation, the same U3 mutations were introduced into the 5' U3 region of the pNL4-3 clone (with and without concomitant 3' mutations). The resulting viruses had either no phenotype (the 5' U3 mutations alone) or the same phenotype as the original $U3_{PK}$ mutant (those containing both 5' and 3' U3 mutations), which suggests that alteration of the SP1 binding site did not disrupt viral RNA production. The double-mutant species was used for viral spread and competition assays as described below.

Separation of Mutant $U3_{PK}$ and Wild-Type NL4-3 SHAPE-MaP Data.

Gene-specific primer SHAPE-MaP data for $U3_{PK}$ (for the construct in which the 3' U3 alone was mutated) revealed that the three nucleotides targeted for mutagenesis showed unusually high mutation rates when aligned to the mutant sequence, which suggested the presence of multiple sequence populations. Quantifying the relative abundance of each variant sequence showed that 61.8% of reads contained the native sequence, 36.0% contained the designed mutant sequence and a small fraction (2.2%) contained other sequences. These ratios suggest that recombination between the native sequence and mutant U3 regions occurred during transfection, producing fitter HIV-1 virus that grew more rapidly than the mutant virus during virus culture. This mutant virus was grown in H9 cells (ATCC, Manassas, Va., United States of America) for 3 weeks before RNA extraction and SHAPEMaP testing. Reactivity profiles for the designed mutant and the wild-type sequence were created by computationally separating the reads after alignment. In addition, SHAPE-MaP reactivity data for the three mutated nucleotides were obtained by selecting reads targeting two mutated nucleotides at a time to assign wild-type or mutant membership, allowing variation at the third nucleotide to determine the mutation rate. This approach is widely applicable to chemically probing populations of RNAs in which each sequence fraction is larger than the expected reverse transcription-induced per-nucleotide mutation rate (~1% in this work).

HIV replication assays.

Viruses were tested for cell-to-cell spread in Jurkat (ATCC) and H9 T cell lines. Cells were confirmed to be free of biological contaminants. Virus inocula were normalized by TZM-bl infectivity at a low multiplicity of infection (less than 0.01) before infection and used to infect 5×105 cells in 1 ml RPMI-1640 medium in 12-well plates; infections were carried out in duplicate. A full medium change was performed 3 d postinfection (d.p.i.), and the medium in each well was harvested and replaced at 4 d.p.i., 5 d.p.i. and 6 d.p.i. Viral concentrations were quantified by p24 assay (AlphaLISA™ HIV; PerkinElmer).

HIV Competition Assays.

Mutant and native sequence virus were mixed at a 10:1 ratio and used to infect $5 \times 10^5$ Jurkat cells in 1 ml total volume in 12-well plates. Infections were performed using half as much mutant and 20-fold less wild-type virus relative to the viral replication assays. Competition experiments were carried out in duplicate. Medium was initially harvested at 2 d.p.i. to represent the initial inoculum. The medium was harvested at 3 d.p.i., 4 d.p.i., 5 d.p.i. and 6 d.p.i., and p24 (capsid protein) was quantified in medium (AlphaLISA™ HIV p24 kit). We required that p24 levels increase exponentially through day 6 to ensure that uninfected cells were in excess through the infections. Viral RNA was purified from medium (QIAamp™ viral RNA mini kit, Qiagen) and reverse transcription using SuperScript™ III (Life Technologies) was carried out using Primer ID primers (Jabara, C. B., et al. *Proc. Natl. Acad. Sci. USA* 108, 20166-20171 (2011) to barcode each cDNA produced and eliminate population biases introduced during PCR. Subsequent sample preparation was performed as described above for SHAPE-MaP using targeted gene-specific primers. After sequencing, paired-end reads were merged into longer synthetic reads using fast length adjustment of short reads (FLASH)(Magoč, T. & Salzberg, S. L. *Bioinformatics* 27, 2957-2963 (2011)). Next, synthetic reads were aligned to the expected NL4-3 sequence for the targeted regions using Bowtie™ 2 (Langmead, B. & Salzberg, *Nat. Methods* 9, 357-359 (2012)) software (using default parameters). A consensus read was built for each PrimerID based on a Phred score voting metric. Identifiers (IDs) matching either native or mutant sequences were required to have the expected point mutations in all locations in order to be considered. The fraction of mutant IDs was expressed as the number of mutant IDs out of the sum of mutant and native IDs. Relative fitness of mutant viruses was determined from the rate of change of the ratio of mutant to NL4-3 measured over time (Resch, W., et al. *J. Virol.* 76, 8659-8666 (2002)).

Calculation of Differences in SHAPE Reactivities in Pseudoknot Mutants.

Standard error measurements of SHAPE reactivities, estimated from the Poisson distribution, are dependent on the number of reads obtained for each sample. The observation that standard error decreases with the inverse square of read depth was used to derive a scaling equation that normalizes to a common depth of 8000 reads to account for differences in sequencing depth between samples. The standard error scaling factor, $f_0$, was calculated for each sample based on the average read depth, $r_{ave}$, of the lowest sequenced component (SHAPE modified, untreated, and denaturing conditions) contributing to the SHAPE reactivity profile:

$$f_0 = \frac{(r_{ave})^{-\frac{1}{2}}}{(8000)^{-\frac{1}{2}}} \qquad (8)$$

After scaling standard errors to a common read depth, significance for each point was calculated using a modified z-factor test (Zhang, J., et al. *J. Biomol. Screen.* 4, 67-73 (1999)) requiring differences to be greater than 1.96 times the sum of the standard errors. $Z_{factor}$ scores greater than zero were considered significant:

$$Z_{factor} = 1 - \frac{1.96(\sigma_{PK} + \sigma_{WT})}{|\mu_{PK} - \mu_{WT}|} \quad (9)$$

Isolated reactivity changes can be viewed as noise in the context of a global structure shift resulting from disruption of a pseudoknot. Therefore, in addition to the z-factor test, differences were required to be consecutive.

TABLE 4

Structures in the HIV-1 RNA genome that are similar between the current and 2009 models (Watts, J.M. et al. *Nature* 460, 711-716 (2009))

| Participating nucleotides | Structural element(s) |
| --- | --- |
| 1-56 | 5' TAR |
| 58-104, 399-484 | 5' pseudoknot and surrounding helices |
| 105-344 | PBS, DIS, and Psi element (largely consistent) |
| 581-657 | branched hairpins |
| 1177-1198, 1294-1312 | helix |
| 1214-1247 | hairpin |
| 1418-1451 | stem-loop |
| 1531-1541 | very short hairpin |
| 1568-1707 | frameshift (largely consistent) |
| 2015-2171 | longest continuous helix and nearby hairpins |
| 2629-2654 | stem-loop |
| 2714-2745 | 2 short hairpins |
| 2781-2802 | hairpin |
| 3140-3149 | very short hairpin |
| 4754-4770 | short hairpin |
| 5267-5343 | short stem-loops |
| 5600-5639 | stem-loop |
| 5793-5878, 5985-6013 | 2 helices and 2 hairpins |
| 5943-5964 | hairpin |
| 6869-6926, 7037-7065 | helices and internal loops |
| 7244-7600 | RRE |
| 7991-8015 | hairpin |
| 8518-8641 | PPT and flanking stem-loops (largely consistent) |
| 8867-8906 | hairpin |
| 9042-9067 | 2 short hairpins upstream of 3' TAR |
| 9070-9138 | 3' TAR |

TABLE 5

RNA elements with verified functional structures, used to examine the significance of algorithmically discovered motifs in the HIV-1 genome. Sequence numbering is based on the NL4-3 reference with the 5' most RNA nucleotide defined as +1.

| RNA Element | Nucleotide position |
| --- | --- |
| 5' LTR R | 1-97 |
| 5' LTR U5 | 98-180 |
| PSI element | 227-353 |
| Ribosomal frameshift | 1559-1719 |
| Splice donors | 286-297, 5587-5598 |
| Central polypurine tract (CPPT) | 4331-4345 |
| Splice acceptors | 5303-5323, 5465-5522, 8700-8713 |
| Rev responsive element (RRE) | 7294-7550 |
| V1/V2 | 6097-6174 |
| V3 | 6644-6756 |

TABLE 5-continued

RNA elements with verified functional structures, used to examine the significance of algorithmically discovered motifs in the HIV-1 genome. Sequence numbering is based on the NL4-3 reference with the 5' most RNA nucleotide defined as +1.

| RNA Element | Nucleotide position |
| --- | --- |
| V4 | 6921-7020 |
| V5 | 7149-7179 |
| Polypurine tract (PPT) | 8605-8619 |
| 5' U5/R pseudoknot ($5'_{PK}$) | 79-86, 442-449 |
| $ENV_{PK}$ | 5666-5676, 5971-5981 |
| $RT_{PK}$ | 2682-2689, 2828-2835 |
| $U3_{PK}$ | 9027-9033 |
| 3' LTR R | 8622-9076 |
| 3' LTR U3 | 9077-9173 |

TABLE 6

Representative sequencing read counts for HIV-1 SHAPE-MaP analysis.

| Sample reads | Run type | Paired reads | Unpaired reads | Total |
| --- | --- | --- | --- | --- |
| 1M7 modified | Hi-Seq 2 × 100 | 4,141,728 | 188,353 | 4,330,081 |
| 1M6 modified | Hi-Seq 2 × 100 | 3,851,060 | 148,671 | 3,999,731 |
| NMIA modified | Hi-Seq 2 × 100 | 4,406,294 | 207,074 | 4,613,368 |
| 1M7 denatured | MiSeq 2 × 150 | 1,017,303 | 16,836 | 1,034,139 |
| 1M6 denatured | MiSeq 2 × 150 | 1,231,002 | 19,637 | 1,250,639 |
| NMIA denatured | MiSeq 2 × 150 | 1,245,518 | 20,934 | 1,266,452 |
| Untreated (DMSO) | Hi-Seq 2 × 100 | 6,687,508 | 281,251 | 6,968,759 |

REFERENCES

Adachi, A. et al. 1986. J. Virol. 59, 284-291.
Alvarez D E, et al. 2005. J Virol 79: 6631-6643.
Archer E J, et al. 2013. Biochemistry 52: 3182-3190.
Bailor M H, et al. 2011. Curr Opin Struct Biol 21: 296-305.
Beckman, R. A., et al. *Biochemistry* 24, 5810-5817 (1985).
Brierley, I., et al. 2007. Nat Rev Micro 5, 598-610.
Bustamante C. 1999. J Mol Biol 293: 271-281.
Byun, Y. & Han, K. *Nucleic Acids Res.* 34, W416-22 (2006).
Chen, T. & Romesberg. 2014. FEBS Lett. 588, 219-229.
Cordero P, et al. 2012. Biochemistry 51: 7037-7039.
Dann C E, et al. 2007. Bioinformatics 25: 1974-1975.
Deigan K E, et al. 2009. Proc Natl Acad Sci 106: 97-102.
Derdeyn, C. A. et al. 2000. J. Virol. 74, 8358-8367.
Dethoff E A, et al. 2012. Nature 482:322-330.
Ding Y et al. 2014. Nature 505:696-700.
Doty P et al. 1959. Proc. Natl. Acad. Sci. 45: 482-499
Ghadessy, F J & Holliger. 2007. Methods Mol. Biol. 352: 237-248.
Gherghe C M, et al. 2008. J Am Chem Soc 130: 8884-8885.
Gherghe C et al. Proc. Natl. Acad. Sci. 107, 19248-19253 (2010).
Gilmartin, G M, et al. 1992. EMBO J. 11: 4419-4428.
Grohman J K, et al. 2013. Science 340: 190-195.
Hajdin C E, et al. 2010. RNA 16: 1340-1349.
Hajdin C E, et al. 2013. Proc Natl Acad Sci 110:5498-5503.
Harrich, D. et al. J. Virol. 1989. 63, 2585-2591.
Hunter, J. D. Matplotlib: *Comput. Sci. Eng.* 90-95 (2007).
Huynen M, et al. 1997. J. Mol. Biol. 267: 1104-1112.
Jabara, C. B., et al. 2011. Proc. Natl. Acad. Sci. 108, 20166-20171.
Jin Y, Yang Y, Zhang P. 2011. RNA Biol 8: 450-457.
Karabiber F, et al. 2013. RNA 19: 63-73.
Kertesz, M. et al. 2010. Nature 467: 103-107.

Kladwang W, et al. 2011a. Nat Chem 3: 954-962.
Kladwang W, et al. 2011b. Biochemistry 50: 8049-8056.
Klasens, B I, et al. 1999. Nucleic Acids Res. 27: 446-454.
Leonard C W, et al. 2013. Biochemistry 52: 588-595.
Leontis N B, Lescoute A, Westhof E. 2006. Curr Opin Struct Biol 16: 279-287.
Low J T, Weeks K M. 2010. Methods 52: 150-158.
Lorsch, J. R, et al. 1995. Nucleic Acids Res. 23: 2811-2814.
Lucks, J. B. et al. 2011. Proc. Natl. Acad. Sci. 108: 11063-11068.
Magoč, T. & Salzberg. 2011. Bioinformatics 27, 2957-2963.
Matathias, A., Fox, D. & Crouse, J. 1999. SuperScript II RNase H⁻ reverse transcriptase. 18064-3, (Focus On, Life Technologies).
Mathews D H, Turner D H. 2006. Curr Opin Struct Biol 16: 270-278.
Mathews D H, et al. 2004. Proc Natl Acad Sci 101: 7287-7292.
Mathews D H. 2004. RNA 10: 1178-1190.
Matoulkova, E, et al. 2012. RNA Biol 9: 563-576 Mauger D M, Siegfried N A,
Weeks K M. 2013. FEBS Lett 587: 1180-1188.
Mauger, D M & Weeks, K M. 2010. Nat. Biotechnol 28: 1178-1179.
McGinnis J L, et al. 2012. J Am Chem Soc 134: 6617-6624.
McGinnis J L & Weeks, K. M. 2014. *Biochemistry.* 53: 3237-3247.
Merino E J, et al. 2005. J Am Chem Soc 127:4223-4231.
Mortimer S A, Weeks K M. 2007. J Am Chem Soc 129: 4144-4145.
Mortimer S A, Weeks K M. 2009. Proc Natl Acad Sci 106: 15622-15627.
Munroe R. 2012. Star Ratings. http://xkcd.com/1098/.
Paillart J C., et al. 2002. J. Biol. Chem. 277: 5995-6004.
Patterson, J T, et al. 2006. RNA Biol 3: 163.
Pollom, E. et al. 2013. PLoS Pathog. 9: e1003294.
Resch, W, et al. 2002. J. Virol. 76, 8659-8666.
Reuter J S, Mathews D H. 2010. BMC Bioinformatics 11: 129.
Rice G M, et al. 2014. RNA 20: 846-854.
Rivas E et al. 2012. RNA 18: 193-212.
Rohl C A, et al. 2004. Methods Enzymol/Numerical Computer Methods 383: 66-93.
Rouskin S, et al. 2014. Nature 505: 701-705.
Sharp P A. 2009. Cell 136: 577-580.
Spitale, R C et al. 2013. Nat. Chem. Biol. 9: 18-20.
Steen K A, Rice G M, Weeks K M. 2012. J Am Chem Soc 134: 13160-13163.
Staple D W & Butcher S E. 20015. PLoS Biol. 3: e213.
Staple, D W. et al. 2012. Nat. Meth. 9, 357-359 (2012).
Talkish, J, et al. *RNA* 20, 713-720 (2014).
Tyrrell, J, et al. 2013. Biochemistry 52, 8777-8785.
Underwood, J. G. et al. 2010. Nat. Meth. 7: 995-1001.
Wan, Y. et al. Nature. 2014. 505, 706-709.
Watts J M, et al. 2009. Nature 460: 711-716.
Weeks K M. 2010. Curr Opin Struct Biol 20: 295-304.
Weeks, K M, 2011. Proc. Natl. Acad. Sci. 108: 10933-10934.
Weeks, K M & Mauger, D M. 2011. Acc. Chem. Res. 44: 1280-1291.
Wilkinson K A, et al. 2006. Nat Protoc 1:1610-1616.
Wilkinson K A, et al. 2008. PLoS Biol 6: e96
Williams, R. et al. *Nat. Meth.* 3, 545-550 (2006).
Zhang, J., et al. 1999. J. Biomol. Screen. 4, 67-73.

It will be understood that various details of the presently claimed subject matter can be changed without departing from the scope of the presently claimed subject matter. Furthermore, the foregoing description is for the purpose of illustration only, and not for the purpose of limitation.

---

What is claimed is:

1. A method for detecting structural data in a ribonucleic acid (RNA), the method comprising:
   a. providing a RNA;
   b. exposing the RNA to a reagent that modifies nucleotides in the RNA to form a covalent ribose 2'-O-adduct or to form a methyl adduct at the N1 position of adenosine or the N3 position of cytosine, thereby providing a modified RNA;
   c. synthesizing a deoxyribonucleic acid (DNA) using a Moloney murine leukemia virus (MMLV) reverse transcriptase and the modified RNA provided in step (b) as a template, wherein the synthesizing occurs under conditions wherein the reverse transcriptase reads through the chemical modification in the modified RNA provided in step (b) to thereby produce a non-complementary deoxyribonucleotide or a deletion in the resulting DNA at the site of the chemical modification, wherein said conditions comprise contacting the modified RNA with the reverse transcriptase and $Mn^{2+}$ for at least one hour;

d. detecting the non-complementary deoxyribonucleotide or the deletion; and e. determining structural data for the RNA provided in step (a).

2. The method of claim 1, comprising detecting two or more chemical modifications.

3. The method of claim 2, wherein the reverse transcriptase reads through multiple chemical modifications to produce multiple non-complementary nucleotides or deletions and the detecting comprises detection of each non-complementary nucleotide or deletion.

4. The method of claim 1, wherein the reagent comprises an electrophile that selectively modifies unconstrained nucleotides in the RNA to form a covalent ribose 2'-O-adduct.

5. The method of claim 1, wherein the reagent is 1M7, 1M6, NMIA, DMS, or combinations thereof.

6. The method of claim 1, wherein the RNA provided in step (a) is present in or derived from a biological sample.

7. The method of claim 1, wherein the reverse transcriptase is a native reverse transcriptase or a mutant reverse transcriptase.

8. The method of claim 1, wherein detecting the non-complementary deoxyribonucleotide or the deletion comprises sequencing the DNA.

9. The method of claim 8, wherein the sequence information is aligned with the sequence of the RNA provided in step (a).

10. The method of claim 1, wherein detecting the non-complementary deoxyribonucleotide or the deletion comprises employing massively parallel sequencing on the DNA.

11. The method of claim 1, comprising amplifying the DNA.

12. The method of claim 1, further comprising normalizing, comparing, and/or joining different data sets containing nucleic acid structural information, optionally wherein the nucleic acid structural information comprises RNA structural information.

13. The method of claim 1, wherein the RNA of step (a) comprises a structure comprising a primer binding site, a protein binding site, a small molecule binding site, or a combination thereof.

14. The method of claim 1, comprising analyzing RNA acid structure in the presence and absence of a primer, a protein, a small molecule or a combination thereof to identify a primer binding site, a protein binding site, a small molecule binding site, or a combination thereof.

* * * * *

SEQUENCE LISTING

```
<160> NUMBER OF SEQ ID NOS: 12

<210> SEQ ID NO 1
<211> LENGTH: 120
<212> TYPE: RNA
<213> ORGANISM: Escherichia coli

<400> SEQUENCE: 1
ugccuggcgg ccguagcgcg gugguccacc cugaccccau gccgaacuca gaagugaaac      60
gccguagcgc cgaugguagu guggggucuc cccaugcgag aguagggaac ugccaggcau     120

<210> SEQ ID NO 2
<211> LENGTH: 158
<212> TYPE: RNA
<213> ORGANISM: Fusobacterium nucleatum

<400> SEQUENCE: 2
gauaugagga gagauuucau uuuaaugaaa caccgaagaa guaaaucuuu cagguaaaaa      60
ggacucauau uggacgaacc ucuggagagc uuaucuaaga gauaacaccg aaggagcaaa    120
gcuaauuuua gccuaaacuc ucagguaaaa ggacggag                            158

<210> SEQ ID NO 3
<211> LENGTH: 154
<212> TYPE: RNA
<213> ORGANISM: Bacillus subtilis

<400> SEQUENCE: 3
```

```
cuucguuagg ugaggcuccu guauggagau acgcugcugc ccaaaaaugu ccaaagacgc    60
caauggguca acagaaauca ucgacauaag gugauuuuua augcagcugg augcuugucc   120
uaugccauac agugcuaaag cucuacgauu gaag                               154
```

<210> SEQ ID NO 4
<211> LENGTH: 425
<212> TYPE: RNA
<213> ORGANISM: Tetrahymena thermophila

<400> SEQUENCE: 4

```
cucucuaaau agcaauauuu accuuuggag ggaaaaguua ucaggcaugc accugguagc    60
uagucuuuaa accaauagau ugcaucgguu uaaaaggcaa gaccgucaaa uugcgggaaa   120
ggggucaaca gccguucagu accaagucuc aggggaaacu uugagauggc cuugcaaagg   180
guaugguaau aagcugacgg acaugguccu aaccacgcag ccaagcccua agcaacaga    240 ucuucuguug auauggaugc aguuccagac uaaaugucgg ucggggaaga uguauucuuc   300
ucauaagaua uagucggacc ucccuuaau gggagcuagc ggaugaagug augcaacacu    360
ggagccgcug ggaacuaaau uguaugcgaa aguauauuga uuaguuuugg aguacucgua   420
aggua                                                               425
```

<210> SEQ ID NO 5
<211> LENGTH: 80
<212> TYPE: DNA
<213> ORGANISM: Escherichia coli

<400> SEQUENCE: 5

```
ggactcgggg tgcccttctg cgtgaaggct gagaaatacc cgtatcacct gatctggata    60
atgccagcgt agggaagttc                                                80
```

<210> SEQ ID NO 6
<211> LENGTH: 158
<212> TYPE: DNA
<213> ORGANISM: Tetrahymena thermophila

<400> SEQUENCE: 6

```
gaattgcggg aaaggggtca acagccgttc agtaccaagt ctcaggggaa actttgagat    60
ggccttgcaa agggtatggt aataagctga cggacatggt cctaaccacg cagccaagtc   120
ctaagtcaac agatcttctg ttgatatgga tgcagttc                           158
```

<210> SEQ ID NO 7
<211> LENGTH: 268
<212> TYPE: DNA
<213> ORGANISM: Bacillus stearothermophilus

<400> SEQUENCE: 7

```
gttaatcatg ctcgggtaat cgctgcggcc ggtttcggcc gtagaggaaa gtccatgctc    60
gcacggtgct gagatgcccg tagtgttcgt ggaaacacga gcgagaaacc caaatgatgg   120
taggggcacc ttcccgaagg aaatgaacgg agggaaggac aggcggcgca tgcagcctgt   180
agatagatga ttaccgccgg agtacgaggc gcaaagccgc ttgcagtacg aaggtacaga   240
acatggctta tagagcatga ttaacgtc                                     268
```

<210> SEQ ID NO 8
<211> LENGTH: 18
<212> TYPE: DNA

```
<213> ORGANISM: Artificial Sequence
<220> FEATURE:
<223> OTHER INFORMATION: Artificially synthesized oligonucleotide primer

<400> SEQUENCE: 8
gaaccggacc gaagcccg                                                    18

<210> SEQ ID NO 9
<211> LENGTH: 36
<212> TYPE: DNA
<213> ORGANISM: Artificial Sequence
<220> FEATURE:
<223> OTHER INFORMATION: Artificially synthesized oligonucleotide primer
<220> FEATURE:
<221> NAME/KEY: misc_feature
<222> LOCATION: (1)..(36)
<223> OTHER INFORMATION: The oligonucleotide primer can optionally have
      a gene-specific primer attached at its 3' end

<400> SEQUENCE: 9
gactggagtt cagacgtgtg ctcttccgat cnnnnn                                36

<210> SEQ ID NO 10
<211> LENGTH: 29
<212> TYPE: DNA
<213> ORGANISM: Artificial Sequence
<220> FEATURE:
<223> OTHER INFORMATION: Artificially synthesized oligonucleotide primer
<220> FEATURE:
<221> NAME/KEY: misc_feature
<222> LOCATION: (1)..(29)
<223> OTHER INFORMATION: The oligonucleotide primer can optionally have
      a gene-specific primer attached at its 3' end

<400> SEQUENCE: 10
ccctacacga cgctcttccg atctnnnnn                                        29

<210> SEQ ID NO 11
<211> LENGTH: 41
<212> TYPE: DNA
<213> ORGANISM: Artificial Sequence
<220> FEATURE:
<223> OTHER INFORMATION: Artificially synthesized oligonucleotide primer
<220> FEATURE:
<221> NAME/KEY: misc_feature
<222> LOCATION: (24)..(25)
<223> OTHER INFORMATION: The oligonucleotide primer can optionally
      include a barcode attached to the 24th and/or 25th nucleotide

<400> SEQUENCE: 11
caagcagaag acggcatacg agatgtgact ggagttcaga c                          41

<210> SEQ ID NO 12
<211> LENGTH: 54
<212> TYPE: DNA
<213> ORGANISM: Artificial Sequence
<220> FEATURE:
<223> OTHER INFORMATION: Artificially synthesized oligonucleotide primer

<400> SEQUENCE: 12
aatgatacgg cgaccaccga gatctacact ctttccctac acgacgctct tccg            54
```